US011849953B2

(12) United States Patent
Okamura et al.

(10) Patent No.: US 11,849,953 B2
(45) Date of Patent: Dec. 26, 2023

(54) HEMOSTATIC DEVICE

(71) Applicant: GOODMAN CO., LTD., Nagoya (JP)

(72) Inventors: Taku Okamura, Seto (JP); Satoki Hino, Seto (JP)

(73) Assignee: GOODMAN CO., LTD., Nagoya (JP)

(*) Notice: Subject to any disclaimer, the term of this patent is extended or adjusted under 35 U.S.C. 154(b) by 563 days.

(21) Appl. No.: 16/912,217

(22) Filed: Jun. 25, 2020

(65) Prior Publication Data

US 2020/0323533 A1 Oct. 15, 2020

Related U.S. Application Data

(63) Continuation of application No. PCT/JP2018/047454, filed on Dec. 25, 2018.

(30) Foreign Application Priority Data

Dec. 26, 2017 (JP) ................................ 2017-249174
Aug. 10, 2018 (JP) ................................ 2018-151066

(51) Int. Cl.
*A61B 17/12* (2006.01)
*A61B 17/00* (2006.01)

(52) U.S. Cl.
CPC ........ *A61B 17/12* (2013.01); *A61B 17/12136* (2013.01); *A61B 2017/00367* (2013.01);
(Continued)

(58) Field of Classification Search
CPC ........... A61B 2017/00367; A61B 2017/00676; A61B 2017/00623; A61B 2017/0065
See application file for complete search history.

(56) References Cited

U.S. PATENT DOCUMENTS

2002/0072768 A1* 6/2002 Ginn ................. A61B 17/0057
606/198
2003/0028201 A1 2/2003 Navarro et al.
(Continued)

FOREIGN PATENT DOCUMENTS

JP 2002-336264 A 11/2002
JP 2011-508626 A 3/2011
(Continued)

OTHER PUBLICATIONS

Jun. 25, 2021—(EP) Extended EP Search Report—App 18895843.
(Continued)

*Primary Examiner* — Alexander J Orkin
(74) *Attorney, Agent, or Firm* — Banner & Witcoff, Ltd.

(57) ABSTRACT

A hemostatic device is provided with: a first tubular member; a positioning member having a first engagement section and engageable with an opening of a blood vessel; a hemostatic agent arranged further to a proximal end side than the first engagement section of the first positioning member; a push-out member making it possible to push the hemostatic agent out from a distal end section of the first tubular member when the push-out member is moved; a first operation unit for executing a first distal end operation for causing the first tubular member and the push-out member to move in a relative manner to a distal end side, and a second distal end operation for causing the push-out member to move in a relative manner to the distal end side; and a switching mechanism for restricting the second distal end operation until the first distal end operation is completed.

10 Claims, 47 Drawing Sheets

(52) U.S. Cl.
CPC ............ *A61B 2017/00477* (2013.01); *A61B 2017/00676* (2013.01); *A61B 2017/00893* (2013.01); *A61B 2017/12004* (2013.01); *A61B 2017/1205* (2013.01)

(56) References Cited

U.S. PATENT DOCUMENTS

| | | |
|---|---|---|
| 2006/0034930 A1 | 2/2006 | Khosravi et al. |
| 2006/0099238 A1 | 5/2006 | Khosravi et al. |
| 2006/0229674 A1 | 10/2006 | Forsberg |
| 2008/0065121 A1* | 3/2008 | Kawaura ............ A61B 17/0057 606/213 |
| 2009/0171282 A1 | 7/2009 | Pipenhagen et al. |
| 2009/0254110 A1 | 10/2009 | Bagaoisan et al. |
| 2009/0270885 A1* | 10/2009 | Maruyama ......... A61B 17/0057 606/213 |
| 2010/0168789 A1 | 7/2010 | Bagaoisan et al. |
| 2012/0158044 A1 | 6/2012 | Jenson et al. |
| 2012/0283770 A1* | 11/2012 | Kramer ............. A61B 17/0057 606/213 |
| 2013/0253579 A1 | 9/2013 | Hundertmark et al. |
| 2014/0135823 A1* | 5/2014 | Tegels ............... A61B 17/0057 606/213 |
| 2014/0207183 A1 | 7/2014 | Shipp |

FOREIGN PATENT DOCUMENTS

| | | |
|---|---|---|
| JP | 2012-508618 A | 4/2012 |
| JP | 2015-512703 A | 4/2015 |
| JP | 2015-231542 A | 12/2015 |
| WO | 2010/056915 A1 | 5/2010 |
| WO | 2011/161752 A1 | 12/2011 |
| WO | 2013/142515 A1 | 9/2013 |
| WO | 2018/031539 A1 | 2/2018 |

OTHER PUBLICATIONS

Apr. 12, 2022—(KR) Notice of Preliminary Rejection—KR App 10-2020-7019427, Eng. Tran.
Jun. 30, 2020—(WO) International Preliminary Report on Patentability—App PCT/JP2018/047454, Eng Tran.
Jul. 5, 2021—(EP) Extended EP Search Report—App 21155049.6.
Mar. 26, 2019—International Search Report—Intl App PCT/JP2018/047454.
Feb. 20, 2023—(KR) Notice of Preliminary Rejection—KR App 10-2022-7023974, Eng Tran.
Jan. 19, 2023—(CN) First Office Action—CN App 201880070998.9, Eng Tran.
Jul. 20, 2023—(EP) Office Action—App 18895843.3.
Jul. 21, 2023—(EP) Office Action—App 21155049.6.

* cited by examiner

FIG. 21
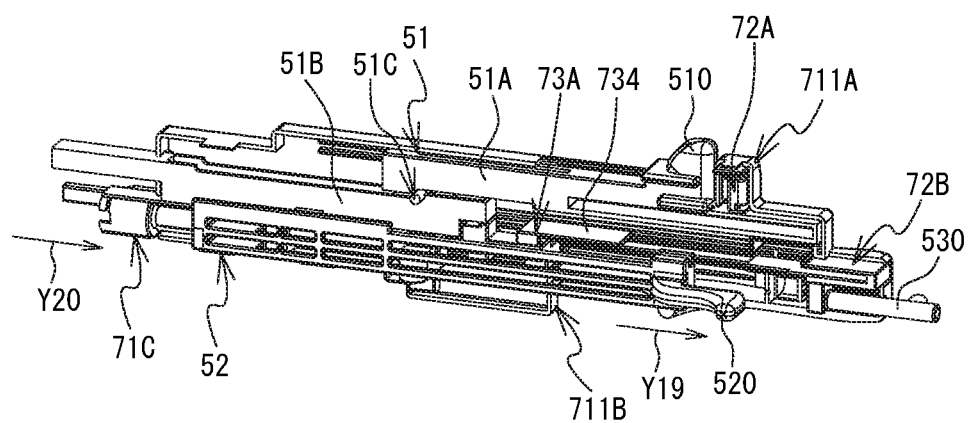
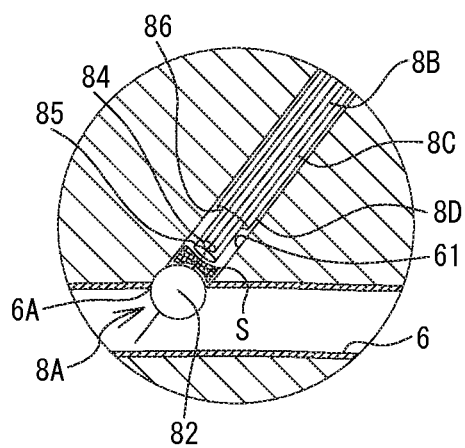

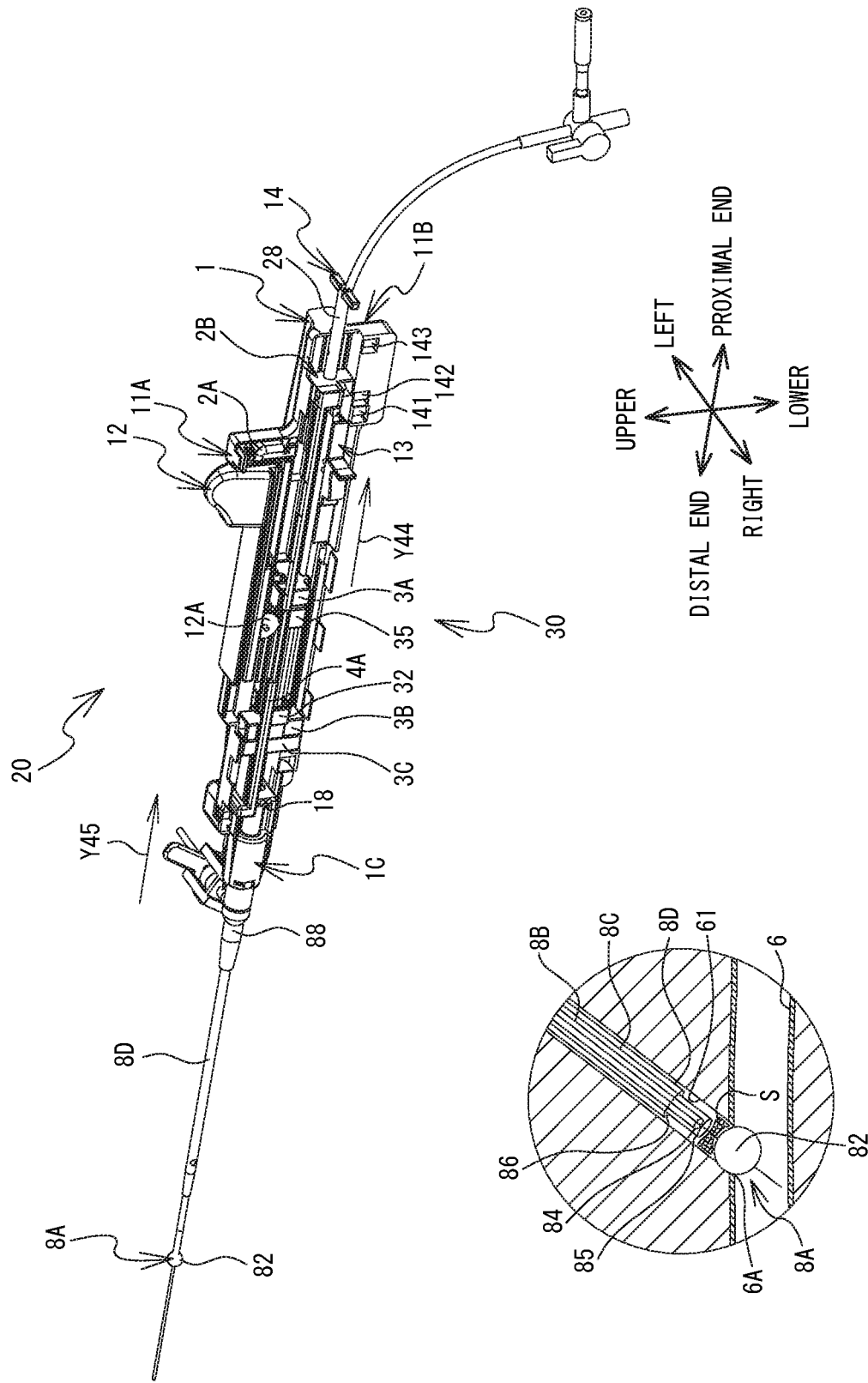

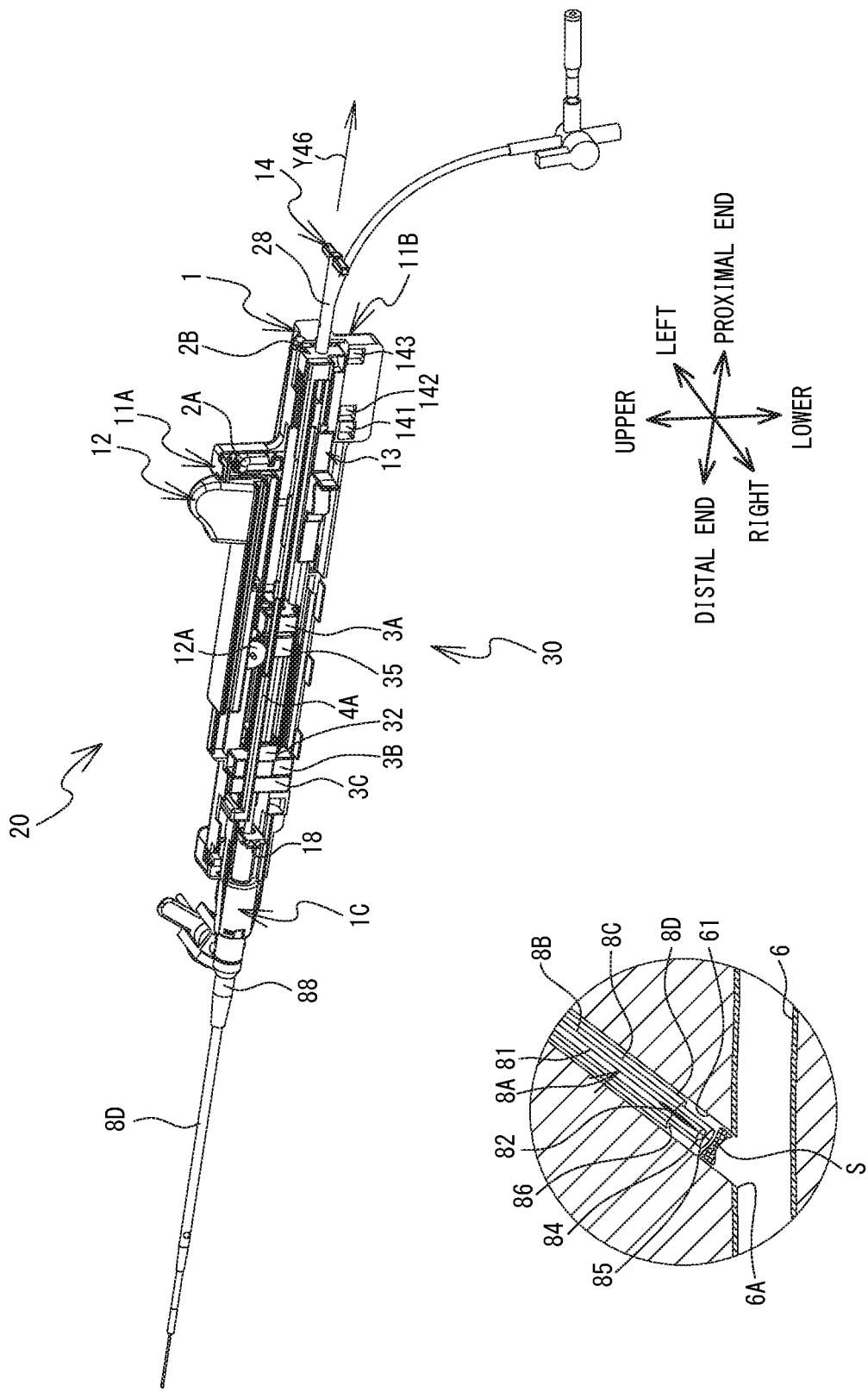

HEMOSTATIC DEVICE

CROSS-REFERENCE TO RELATED APPLICATION

This application is a Continuation Application of International Application No. PCT/JP2018/047454, filed Dec. 25, 2018, which claims priority from Japanese Patent Application No. 2017-249174, filed on Dec. 26, 2017, and Japanese Patent Application No. 2018-151066, filed on Aug. 10, 2018. This disclosure of the foregoing application is hereby incorporated by reference in its entirety.

BACKGROUND

The present disclosure relates to a hemostatic device that closes an opening formed in a blood vessel and stops bleeding.

A medical procedure is known that is performed by accessing a blood vessel via a puncture hole formed by puncture. As an example of this type of medical procedure, there is a procedure in which a constricted location of a blood vessel is expanded using a balloon catheter. After the medical procedure is complete, it is necessary to close the opening formed in the blood vessel by the puncture and stop bleeding.

A device that closes a vascular puncture site is provided with a positioning member including a positioning element, a pusher member, and a plug device (also referred to as a "hemostatic agent"). A method of using the device is as follows. First, the positioning member is inserted into a puncture hole formed in skin by puncture, with the positioning element in a folded state (a first step). Next, the positioning member is expanded while being disposed in a blood vessel (a second step). Next, the positioning member moves in a direction of being pulled out from the puncture hole, and the positioning member comes into contact with an inner wall of the blood vessel (a third step). Next, the pusher member, a delivery sheath, and the hemostatic agent are inserted into the puncture hole along the positioning element (a fourth step). Next, by moving the pusher member to a distal end side with respect to the delivery sheath, the hemostatic agent is pushed from a proximal end side with respect to the positioning element (a fifth step). The hemostatic agent is retained in the proximity of the blood vessel. In this way, the hemostatic agent can perform hemostasis by closing an opening in the blood vessel.

SUMMARY

In the above-described device, when each of the steps is not performed in order, there is a possibility that the opening of the blood vessel cannot be appropriately closed by the hemostatic agent. In particular, if the fifth step is performed before the fourth step is complete, the hemostatic agent is exposed from the delivery sheath before coming into proximity with the positioning element, and this is not desirable. Thus, in particular, there is a demand for a device with which even a user who is not familiar with using the device can easily and reliably perform an operation involving predetermined operations in order.

It is an object of the present disclosure to provide a hemostatic device with which a user is able to easily and appropriately perform an operation for closing an opening in a blood vessel using a hemostatic agent and stop bleeding.

Various embodiment herein provide a hemostatic device that closes a puncture hole extending to skin from an opening formed in a blood vessel. The hemostatic device is characterized by including: a first tubular member extending in an extending direction; a positioning member, a part of which is provided inside the first tubular member, including an extending section extending in the extending direction, and an engagement section provided at a distal end section of the extending section and engageable with the opening; a hemostatic agent disposed further to a proximal end side than the engagement section of the positioning member; a push-out member including a push-out distal end positioned further to the proximal end side than the hemostatic agent, and able to push out the hemostatic agent from a distal end section of the first tubular member, using the push-out distal end, when the push-out member moves relatively to a distal end side with respect to the first tubular member; a housing configured to house at least a part of each of the first tubular member, the positioning member, and the push-out member; a first operation unit that is operated in order to perform each of a first distal end operation that relatively moves the first tubular member and the push-out member to the distal end side with respect to the housing and the positioning member, and a second distal end operation that relatively moves the push-out member to the distal end side with respect to the housing and the positioning member; and a switching mechanism configured to restrict the second distal end operation at least until the first distal end operation is complete, and to release the restriction of the second distal end operation and cause the second distal end operation to be executable once the first distal end operation is complete.

Further, according to a mode of use of the above-described device of the related art, there is a possibility that the hemostatic agent is pressed against the positioning element by the fifth step, in a state in which the operation to move the positioning member in the direction of being pulled from the puncture hole in the third step is not sufficient. In this case, a gap is sometimes formed between the blood vessel and the positioning member. Thus, when the hemostatic agent is pressed against the positioning element in the fifth step, there is a possibility that the hemostatic agent may enter into the blood vessel via the gap between the blood vessel and the positioning element.

Another object of the present disclosure is to provide a hemostatic device capable of inhibiting a hemostatic device from entering into a blood vessel.

Various embodiment herein also provide a hemostatic device that closes a puncture hole extending to skin from an opening formed in a blood vessel. The hemostatic device is characterized by including: a positioning member including an extending section extending in an extending direction, and a first engagement section provided at a distal end section of the extending section in the extending direction and engageable with the opening, a hemostatic agent disposed further to a proximal end side than the first engagement section of the positioning member; a push-out member including a push-out distal end positioned further to the proximal end side than the hemostatic agent, and able to move the hemostatic agent to the distal end side, using the push-out distal end, when the push-out member moves relatively to the distal end side with respect to the positioning member; a restricting member able to restrict the relative movement of the push-out member to the distal end side with respect to the positioning member; a switching member able to switch a state of the restricting member between a restricting state that restricts the relative movement of the push-out member, and an enabling state that does not restrict the relative movement of the push-out member; and a housing configured to house at least a part of each of the positioning member, the push-out member, the restricting member, and the switching member. The switching member switches the restricting member to the enabling state when the positioning member moves relatively to the distal end side with respect to the housing when the restricting member is in the restricting state. After being switched from the restricting state to the enabling state, the restricting member is maintained in the enabling state, irrespective of the relative movement of the positioning member with respect to the housing.

BRIEF DESCRIPTION OF DRAWINGS

Embodiments will be described below in detail with reference to the accompanying drawings in which:

FIG. 21 is a perspective view showing a coupling proximal end operation;

FIG. 46 is a perspective view showing the coupling proximal end operation; and

FIG. 47 is a perspective view showing the positioning distal end operation.

DETAILED DESCRIPTION

A hemostatic device 10 (a first embodiment, with reference to FIG. 1 to FIG. 22), and a hemostatic device 20 (a second embodiment, with reference to FIG. 23 to FIG. 47) according to embodiments of the present disclosure will be explained with reference to the drawings. The hemostatic devices 10 and 20 close a puncture hole using a hemostatic agent S. The puncture hole is formed using a dedicated needle, in a wrist or a groin, for example, when performing a medical treatment using a known catheter. The puncture hole extends from a surface of the skin to an opening formed in a blood vessel. By closing the puncture hole using the hemostatic agent S, the hemostatic devices 10 and 20 suppress a flow of blood to the outside of the skin from the opening in the blood vessel, via the puncture hole.

In the following explanation, an upper side, a lower side, an upper left side, a lower right side, a lower left side, and an upper right side in FIG. 1 respectively define an upper side, a lower side, a left side, a right side, a distal end side, and a proximal end side of the hemostatic device 10. An upper side, a lower side, an upper left side, a lower right side, a lower left side, and an upper right side in FIG. 23 respectively define an upper side, a lower side, a left side, a right side, a distal end side, and a proximal end side of the hemostatic device 20. A direction extending between the distal end side and the proximal end side of each of the hemostatic devices 10 and 20 is an extending direction.

First Embodiment

Figure 2:
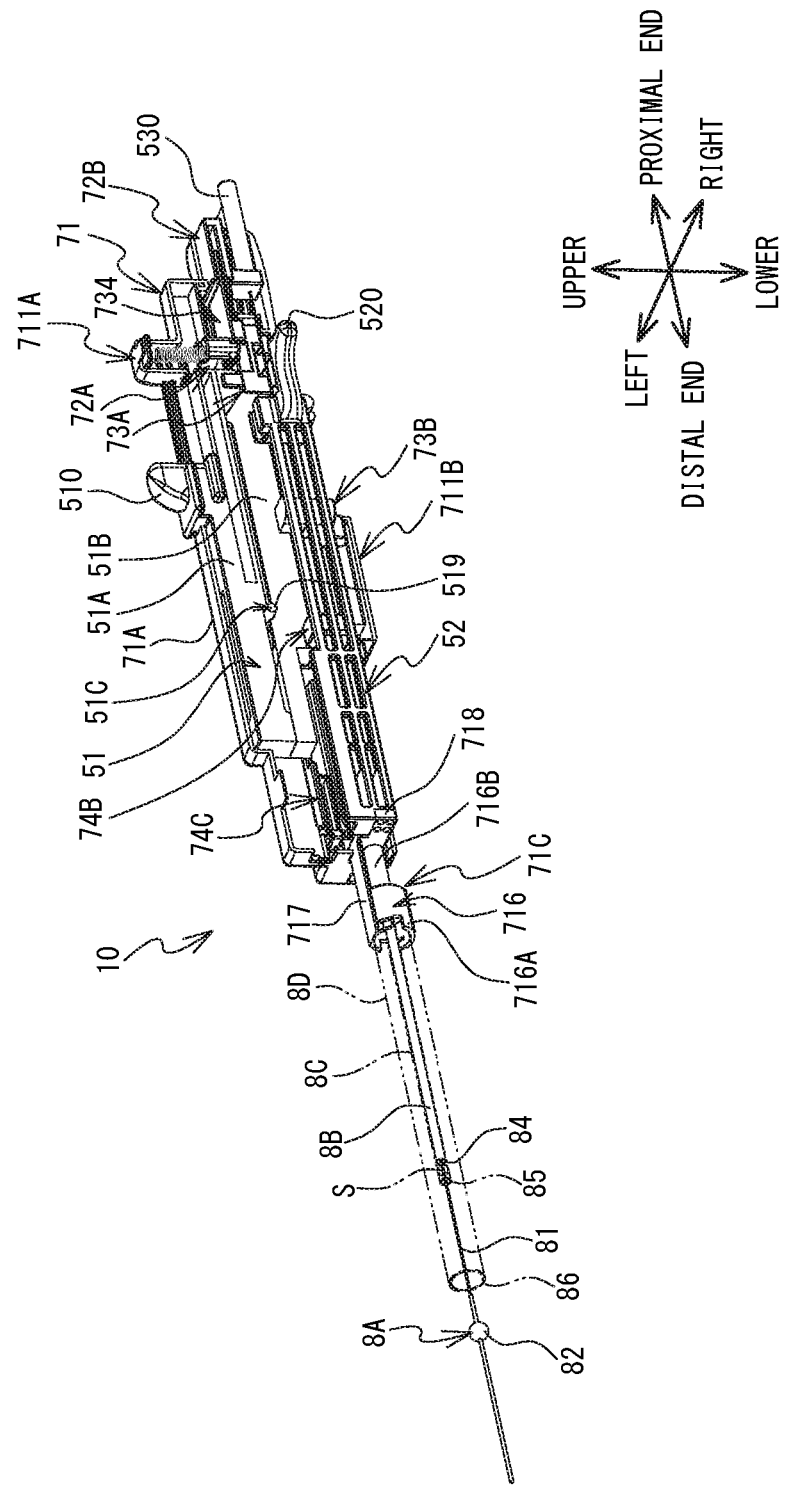
FIG. 2 is a perspective view showing an internal structure of the hemostatic device 10.

As shown in FIG. 2, the hemostatic device 10 includes a housing 71, a positioning member 8A, a push-out member 8B, a first tubular member 8C, a second tubular member 8D, the hemostatic agent S, a restricting member 72A, a switching member 72B, moving members 73A, 73B, and 74B, a coupling section 71C, a restricting mechanism 74C, a lever module 51, and the like. Where there is no specific limitation, a "movement in the extending direction," a "movement to the distal end side," and a "movement to the proximal end side" of each of the members respectively indicate a relative movement where the housing 71 is a point of reference.

Housing 71

Figure 1:
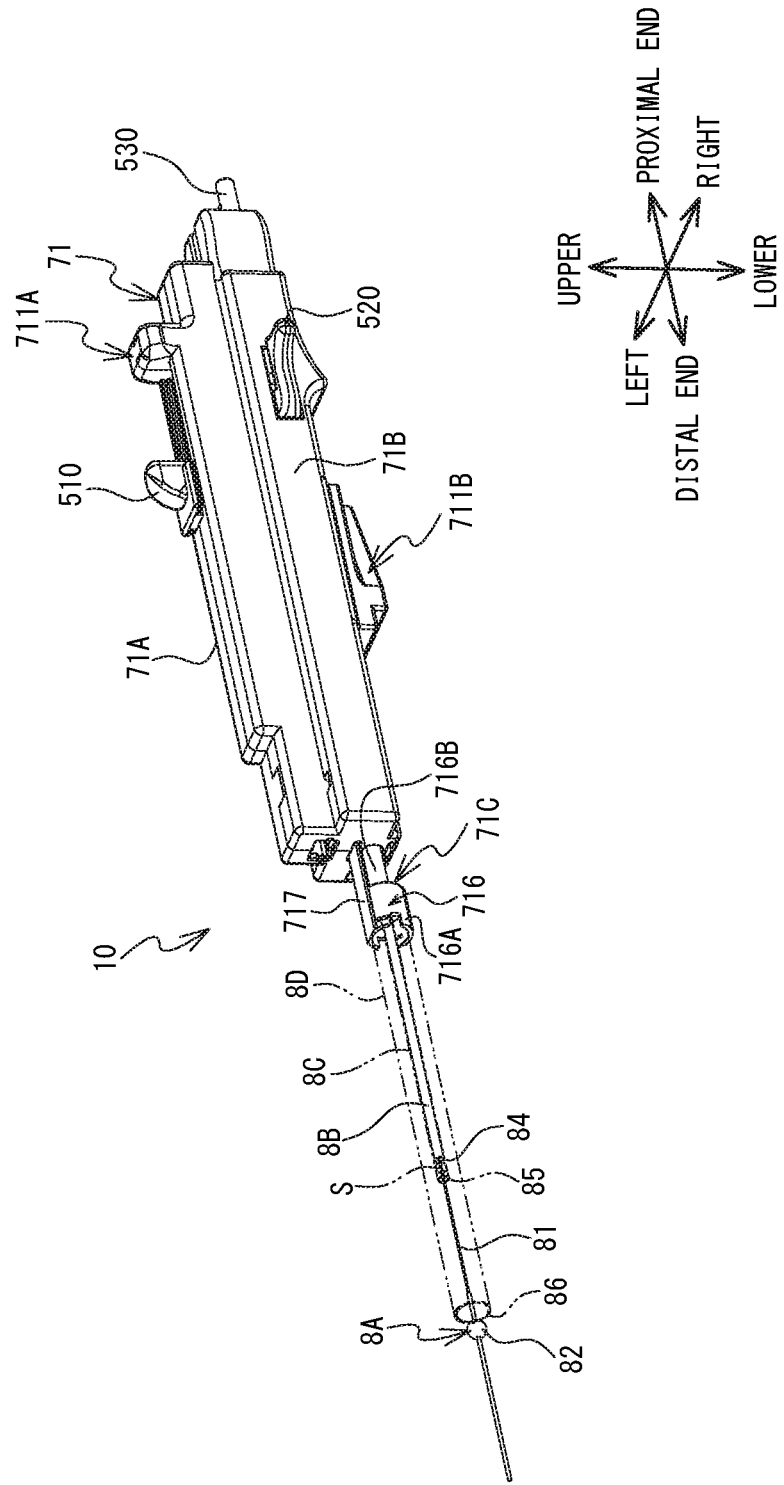
FIG. 1 is a perspective view of a hemostatic device 10.

As shown in FIG. 1, the housing 71 has a substantially cuboid shape that is long in the extending direction. The housing 71 is formed by combining a left housing 71A corresponding to a part that is the left side half of the housing 71, and a right housing 71B corresponding to a part that is the right side half of the housing 71. The housing 71 includes protruding sections 711A and 711B. The protruding section 711A protrudes upward from the upper side in the vicinity of the proximal end section of the housing 71. The protruding section 711B protrudes downward from the lower side in the center, in the extending direction, of the housing 71. As shown in FIG. 2, at least a part of each of the positioning member 8A, the push-out member 8B, the first tubular member 8C, the restricting member 72A, the switching member 72B, the moving members 73A, 73B, and 74B, the restricting mechanism 74C, and the lever module 51, all of which are to be described later, is housed inside the housing 71.

As shown in FIG. 1, on the upper surface of the housing 71, a first operation unit 510 is provided on the distal end side of the protruding section 711A. The first operation unit 510 is a slide lever that is operated by a user, using a finger. The first operation unit 510 can move in the extending direction in accordance with the operation by the user. The first operation unit 510 causes a moving member 51B, and the moving members 73A, 73B, and 74B, to be described later, to move in the extending direction. Further, the first operation unit 510 causes the push-out member 8B that is connected to the moving member 51B, and the first tubular member 8C that is connected to the moving member 73B, to move in the extending direction.

On the right surface of the housing 71, a second operation unit 520 is provided on the proximal end side of the first operation unit 510, in the extending direction. The second operation unit 520 is a slide lever that is operated by the user, using a finger. The second operation unit 520 can move in the extending direction in accordance with the operation by the user. The second operation unit 520 causes the coupling section 71C, and the second tubular member 8D that is connected to the coupling section 71C, to be described later, to move in the extending direction.

A third operation unit 530 is provided on the proximal end side of the housing 71. The third operation unit 530 is a handle that is grasped and operated by the user. The third operation unit 530 can move in the extending direction in accordance with the operation by the user. The third operation unit 530 causes the switching member 72B, and the positioning member 8A that is connected to the switching member 72B, to be described later, to move in the extending direction.

Positioning Member 8A

Figure 3:
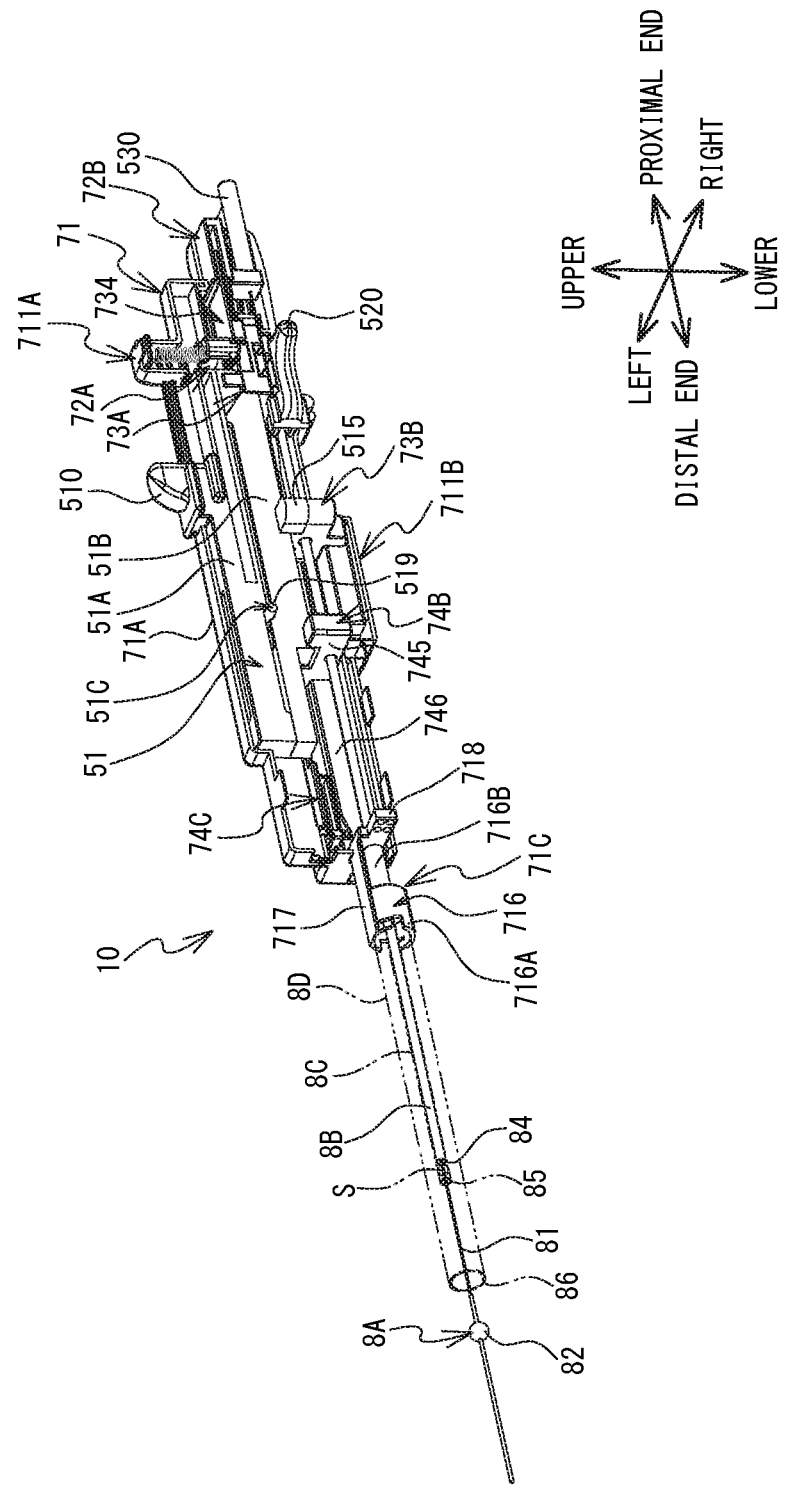
FIG. 3 is a perspective view showing the internal structure of the hemostatic device 10.

The positioning member 8A performs positioning of each of parts of the hemostatic device 10 with respect to the puncture hole. The positioning member 8A is a so-called balloon catheter. As shown in FIG. 1 to FIG. 3, the positioning member 8A includes an extending section 81 and a first engagement section 82. The extending section 81 is a tubular-shaped member extending along the extending direction, and corresponds to a catheter. The proximal end section of the extending section 81 is connected to the switching member 72B to be described later (refer to FIG. 4). The extending section 81 extends from the switching member 72B to the distal end side through the interior of the housing 71, and protrudes to the distal end side from the distal end section of the housing 71. The extending section 81 can move in the extending direction.

The first engagement section 82 is provided on a peripheral surface of the proximal end section of the extending section 81. The first engagement section 82 correspond to a balloon. When a compressed fluid is injected into a lumen of the extending section 81 from a hub (not shown in the drawings) connected to the switching member 72B, the first engagement section 82 switches from a contracted state to an expanded state. FIG. 1 to FIG. 3 show the first engagement section 82 in the expanded state.

Push-Out Member 8B

The push-out member 8B pushes out the hemostatic agent S to be described later from the first tubular member 8C and the second tubular member 8D to be described later, by moving the hemostatic agent S to the distal end side. As shown in FIG. 1 to FIG. 3, the push-out member 8B is a tubular member that extends along the extending direction. The inner diameter of the push-out member 8B is larger than the outer diameter of the extending section 81 of the positioning member 8A. The proximal end section of the push-out member 8B is connected to the moving member 51B to be described later (refer to FIG. 7). The push-out member 8B can move in the extending direction. The push-out member 8B extends from the moving member 51B to the distal end side through the interior of the housing 71, and protrudes to the distal end side from the distal end section of the housing 71. The extending section 81 (refer to FIG. 4) of the positioning member 8A is inserted through a lumen of the push-out member 8B.

The extending section 81 of the positioning member 8A protrudes to the distal end side from the distal end section (referred to as a "push-out distal end 84") of the push-out member 8B. The first engagement section 82 of the positioning member 8A is disposed further to the distal end side than the push-out distal end 84 of the push-out member 8B.

First Tubular Member 8C

The first tubular member 8C is a housing sheath that houses the hemostatic agent S to be described later. As shown in FIG. 1 to FIG. 3, the first tubular member 8C is a tubular member that extends along the extending direction. The inner diameter of the first tubular member 8C is slightly larger than the outer diameter of the push-out member 8B. The proximal end section of the first tubular member 8C is connected to the moving member 73B to be described later (refer to FIG. 11). The first tubular member 8C can move in the extending direction. The first tubular member 8C extends from the moving member 73B toward the distal end side through the interior of the housing 71, and protrudes to the distal end side from the distal end section of the housing 71. The extending section 81 of the positioning member 8A, and the push-out member 8B are inserted through a lumen of the first tubular member 8C. In other words, a part of each of the positioning member 8A and the push-out member 8B is disposed inside the first tubular member 8C. The extending section 81 of the positioning member 8A protrudes to the distal end side from the distal end section (referred to as a "first distal end 85") of the first tubular member 8C. The first engagement section 82 of the positioning member 8A is disposed further to the distal end side than the first distal end 85 of the first tubular member 8C.

A position of the push-out distal end 84 of the push-out member 8B with respect to the first distal end 85 of the first tubular member 8C switches between a state of being disposed on the proximal end side (refer to FIG. 1 to FIG. 3), and a state of being disposed on the distal end side, in accordance with a relative movement, in the extending direction, of the push-out member 8B with respect to the first tubular member 8C.

Second Tubular Member 8D

The second tubular member 8D is an insertion sheath used to insert the positioning member 8A, the push-out member 8B, and the first tubular member 8C into the puncture hole. The second tubular member 8D is a tubular member that extends along the extending direction. The inner diameter of the second tubular member 8D is larger than the outer diameter of the first tubular member 8C. The proximal end section of the second tubular member 8D is connected to the coupling section 71C to be described later. The second tubular member 8D can move in the extending direction.

The extending section 81 of the positioning member 8A, the push-out member 8B, and the first tubular member 8C are inserted through a lumen of the second tubular member 8D. In other words, at least a part of each of the extending section 81 of the positioning member 8A, the push-out member 8B, and the first tubular member 8C is disposed inside the second tubular member 8D. The push-out distal end 84 of the push-out member 8B, and the first distal end 85 of the first tubular member 8C are disposed further to the proximal end side than the proximal end section (referred to as a "second distal end 86") of the second tubular member 8D. The first engagement section 82 of the positioning member 8A is disposed further to the distal end side than the second distal end 86 of the second tubular member 8D.

Hemostatic Agent S

The hemostatic agent S is retained in the puncture hole and closes the opening in the blood vessel. A gel-form polyethylene glycol (PEG), ceratin, collagen, or the like can be used as a material of the hemostatic agent S. The hemostatic agent S is disposed inside the first tubular member 8C, in the state in which the push-out distal end 84 of the push-out member 8B is disposed on the proximal end side with respect to the first distal end 85 of the first tubular member 8C. In this case, the hemostatic agent S is disposed in a portion further to the proximal end side than the first engagement section 82 of the positioning member 8A, and further to the distal end side than the push-out distal end 84 of the push-out member 8B. The hemostatic agent S attaches to the outer peripheral surface of the extending section 81 of the positioning member 8A. When the push-out member 8B has moved relatively to the distal end side with respect to the first tubular member 8C, the hemostatic agent S moves to the distal end side due to the push-out distal end 84. In this way, the hemostatic agent S is pushed to the outside from the interior of the first tubular member 8C, via the first distal end 85.

Switching Member 72B

Figure 4:
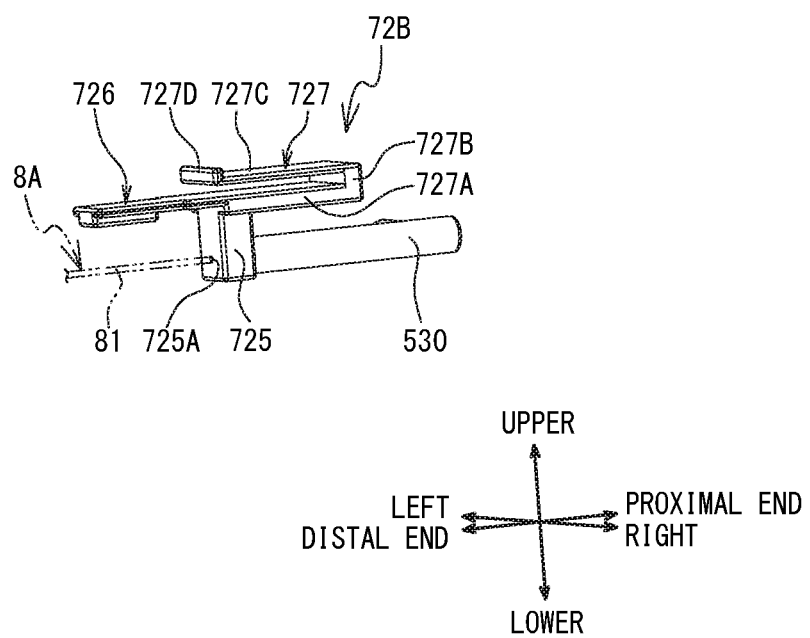
FIG. 4 is a perspective view of a switching member 72B.

As shown in FIG. 3, the switching member 72B is disposed in the vicinity of the proximal end section inside the housing 71. The switching member 72B switches a state of the restricting member 72A (refer to FIG. 10) to be described later. When a force acts on the positioning member 8A, the switching member 72B moves in the extending direction. Further, the switching member 72B moves in the extending direction in accordance with the operation of the third operation unit 530, and causes the positioning member 8A to move in the extending direction. As shown in FIG. 4, the switching member 72B includes a base section 725, and extension sections 726 and 727.

The base section 725 is a substantially cuboid shape. The base section 725 includes a through hole 725A that penetrates the base section 725 in the extending direction over a section between the distal end side and the proximal end side thereof. The proximal end section of the extending section 81 of the positioning member 8A is connected to a surface of the distal end side of the base section 725. The lumen of the extending section 81 is communicated with the through hole 725A of the base section 725.

Each of the extension sections 726 and 727 has a plate shape. The extension section 726 extends toward the distal end side from the upper end section of the base section 725. Hereinafter, the end section on the distal end side of the extension section 726 is referred to as the "distal end section of the extension section 726." The extension section 727 includes a first portion 727A, a second portion 727B, a third portion 727C, and a protruding portion 727D. The first portion 727A extends toward the proximal end side from the upper end section of the base section 725. The second portion 727B extends upward from the proximal end section of the first portion 727A. The third portion 727C extends toward the distal end side from the upper end section of the second portion 727B. The first portion 727A and the third portion 727C face each other with a gap therebetween in the up-down direction. The protruding portion 727D protrudes upward from the distal end section of the third portion 727C. The distal end section of the extension section 726 is inserted, from the proximal end side, through a second engagement section 730 (refer to FIG. 9) of the moving member 73A to be described later.

The third operation unit 530 is connected to the surface on the proximal end side of the base section 725. The third operation unit 530 has a circular tubular shape, and extends to the proximal end side from the surface on the proximal end side of the base section 725. A lumen of the third operation unit 530 is communicated with the through hole 725A of the base section 725. As shown in FIG. 1 to FIG. 3, the third operation unit 530 protrudes to the proximal end side from the proximal end section of the housing 71. The proximal end section of the third operation unit 530 is connected to a hub (not shown in the drawings), via a tube (not shown in the drawings). The hub injects the compressed fluid into the lumen of the extending section 81 of the positioning member 8A, via the lumen of the third operation unit 530 and the through hole 725A of the base section 725. The compressed fluid injected into the extending section 81 switches the first engagement section 82 from the contracted state to the expanded state, by causing the first engagement section 82 of the positioning member 8A to inflate.

Figure 5:
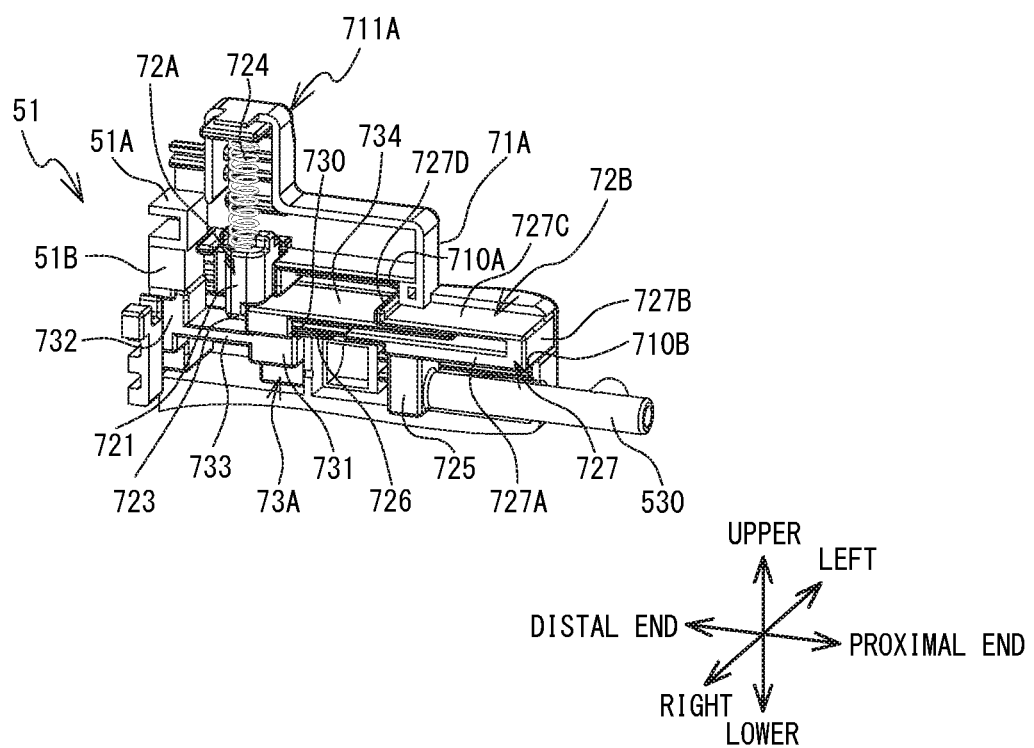
FIG. 5 is a perspective view showing a vicinity of a restricting member 72A in a restricting state.
Figure 6:
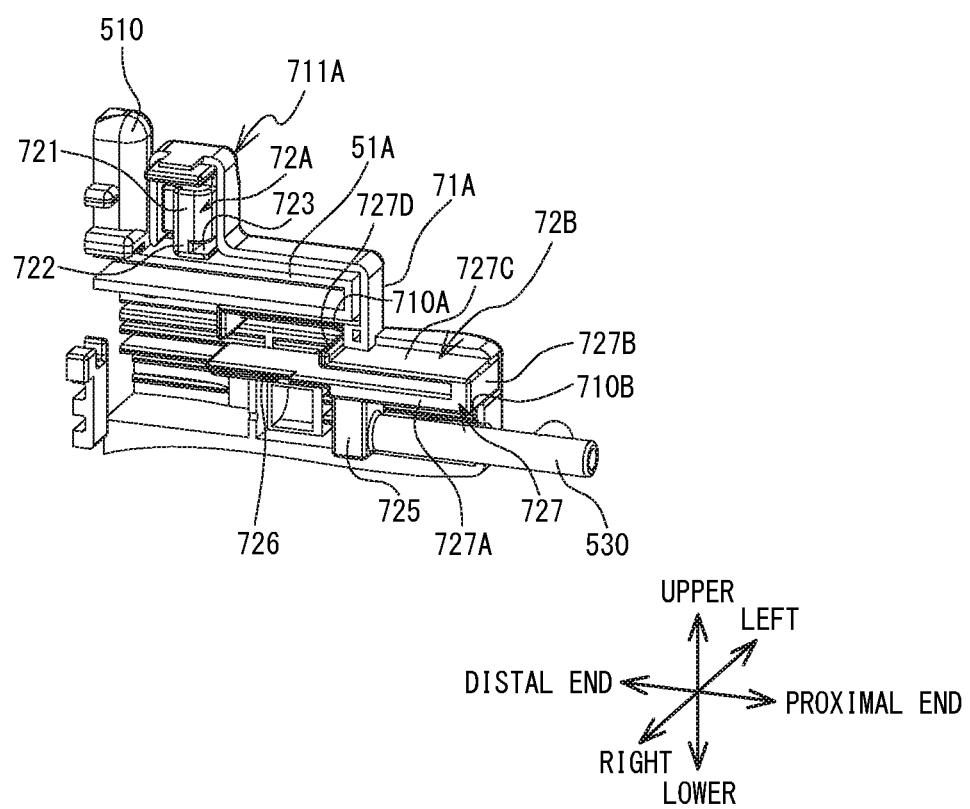
FIG. 6 is a perspective view showing the vicinity of the restricting member 72A in an enabling state.

The switching member 72B can move between a first proximal end position, a first distal end position, and a first intermediate position, which are respectively different positions in the extending direction. As shown in FIG. 5 and FIG. 6, when the switching member 72B is disposed in the first intermediate position, of inner walls of the housing 71, a restriction wall 710A that is formed further to the proximal end side than the protruding section 711A is in contact, from the proximal end side, with the protruding portion 727B of the switching member 72B. The first distal end position is a position further to the distal end side than the first intermediate position. When the switching member 72B is disposed in the first distal end position, the distal end of an extension section 734 of the moving member 73A to be described later is in contact, from the distal end side, with the second section 727B of the switching member 72B. The first proximal end position is a position further to the proximal end side than the first intermediate position. When the switching member 72B is disposed in the first proximal end position, a proximal end wall 710B corresponding to the proximal end section of the inner wall of the housing 71 is in contact, from the proximal end side, with the base section 725 of the switching member 72B. Note that, in an initial state in which the hemostatic device 10 is not being used, the switching member 72B is disposed in the first intermediate position.

Lever Module 51

As shown in FIG. 2 and FIG. 3, the lever module 51 is provided in the vicinity of the upper end section inside the housing 71. The lever module 51 includes moving members 51A and 51B, and a pinion gear 51C. The moving members 51A and 51B each have a substantially bar-like shape that is long in the extending direction, and are aligned in the up-down direction. The moving member 51B is disposed on the lower side of the moving member 51A. The moving members 51A and 51B each extend in parallel with the other. The pinion gear 51C is sandwiched from above and below by the moving members 51A and 51B. A rotation shaft of the pinion gear 51C extends in the left-right direction.

Figure 7:
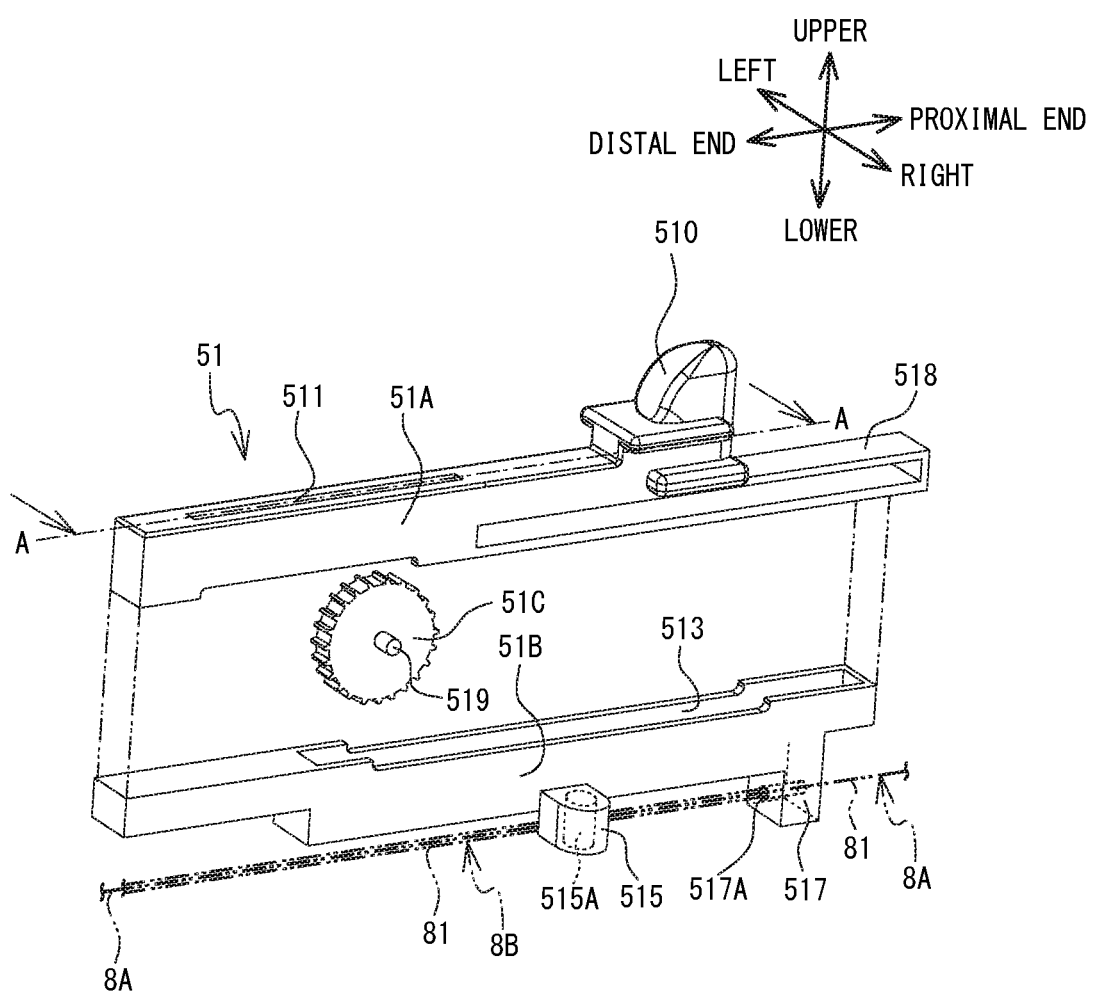
FIG. 7 is an exploded perspective view of a lever module 51.
Figure 8:
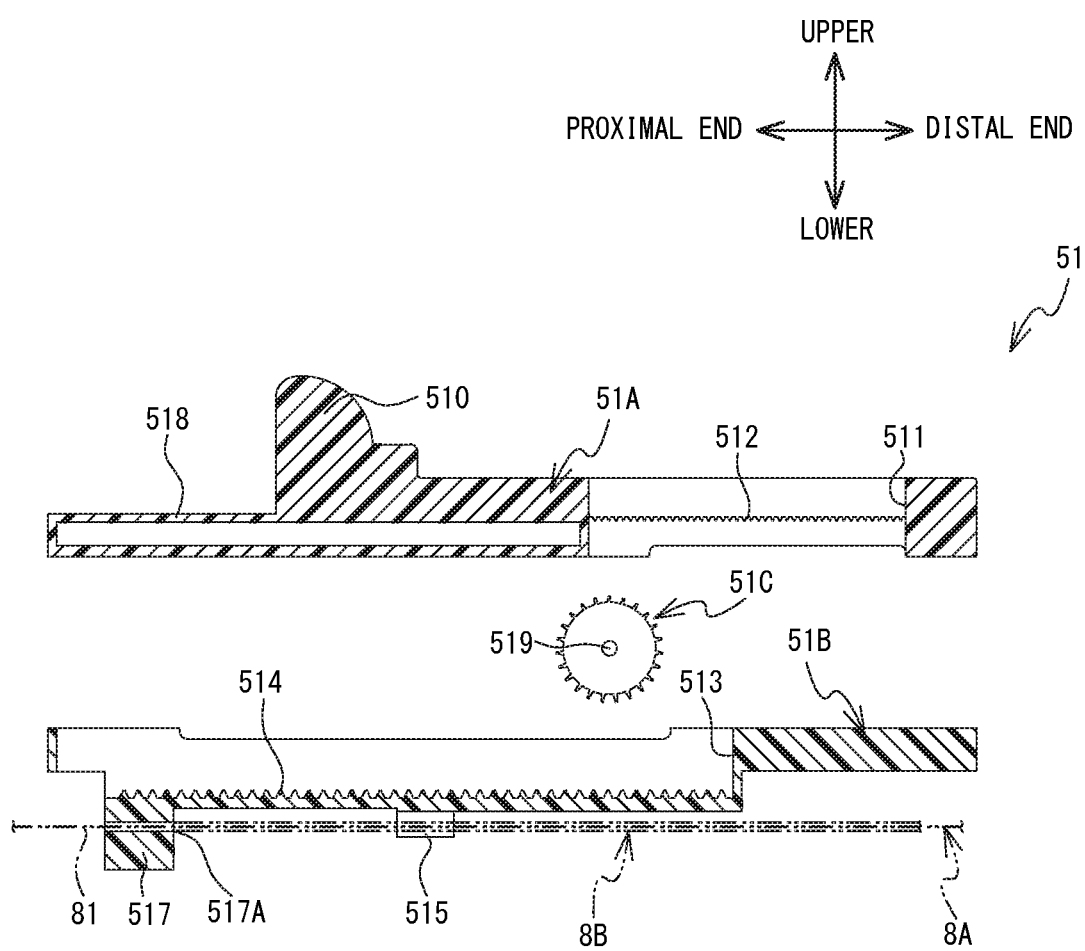
FIG. 8 is a cross-sectional view as seen in the direction of arrows along a line A-A shown in FIG. 7.

As shown in FIG. 7, a slit-shaped through hole 511 that penetrates in the up-down direction is formed in a portion of the moving member 51A further to the distal end side than a center thereof in the extending direction. As shown in FIG. 8, a rack gear 512 is provided inside the through hole 511. As shown in FIG. 7, of the upper end section of the moving member 51A, the first operation unit 510 is provided on a portion further to the proximal end side than the through hole 511. Of the moving member 51A, a portion extending further to the proximal end side than the first operation unit 510 is referred to as a "distal end section 518." A groove 513 that extends in the extending direction is provided in the upper surface of the moving member 51B. As shown in FIG. 8, a rack gear 514 is provided inside the groove 513.

The pinion gear 51C is disposed inside the through hole 511 of the moving member 51A and the groove 513 of the moving member 51B. A rotation shaft 519 of the pinion gear 51C is sandwiched in the up-down direction by the moving members 51A and 51B, and is rotatably supported (refer to FIG. 2 and FIG. 3). Teeth of the pinion gear 51C mesh with the rack gears 512 and 514. The pinion gear 51C rotates as a result of the moving member 51A moving in the extending direction in accordance with the operation of the first operation unit 510. When the pinion gear 51C rotates, the moving member 51B moves along the extending direction in the opposite direction to the moving member 51A. Thus, when the operation is performed to move the first operation unit 510 to the distal end side, the moving member 51B moves to the proximal end side. When the operation is performed to move the first operation unit 510 to the proximal end side, the moving member 51B moves to the distal end side.

A protruding section 517 that protrudes downward is provided in the vicinity of the proximal end section of the lower surface of the moving member 51B. A through hole 517A that extends in the extending direction is formed in the protruding section 517. The proximal end section of the push-out member 8B is connected around the periphery of the through hole 517A, of the surface of the distal end side of the protruding section 517. The push-out member 8B extends to the distal end side from the protruding section 517. The extending section 81 of the positioning member 8A that extends to the distal end side from the switching member 72B (refer to FIG. 6) is inserted, from the proximal end side, through the through hole 517A. The positioning member 8A passes through the through hole 517A and extends further to the distal end side than the protruding section 517, and passes through the lumen of the push-out member 8B.

When the moving member 51B moves in the extending direction in accordance with the operation of the first operation unit 510, the push-out member 8B also moves in the extending direction. Hereinafter, the position of the moving member 51B that has moved furthest to the proximal end side is referred to as a "second proximal end position" (refer to FIG. 14 to FIG. 16, to be described later), and the position of the moving member 51B that has moved furthest to the distal end side is referred to as a "second distal end position" (refer to FIG. 19 to FIG. 22, to be described later). An intermediate position between the second proximal end position and the second distal end position is referred to as a "second intermediate position" (refer to FIG. 17 and FIG. 18, to be described later). In the initial state in which the hemostatic device 10 is not being used, the moving member 51B is disposed in the second proximal end position.

As shown in FIG. 7, a protruding section 515 that protrudes to the right is provided in substantially the center, in the extending direction, of the right surface of the moving member 51B. A protruding section 516 (refer to FIG. 20) that protrudes to the left is provided in substantially the center, in the extending direction, of the left surface of the moving member 51B. A magnet 515A (refer to FIG. 7) is built into the protruding section 515, and a magnet 516A (refer to FIG. 20) is built into the protruding section 516.

Moving Member 73A

As shown in FIG. 2 and FIG. 3, the moving member 73A is disposed on the distal end side of the switching member 72B in the interior of the housing 71. The moving member 73A is connected to the end section, on the proximal end side, of the moving member 51B of the lever module 51. When the moving member 51B moves in the extending direction in accordance with the operation of the first operation unit 510, the moving member 73A moves in concert with the moving member 51B in the extending direction.

Hereinafter, a position of the moving member 73A when the moving member 51B is disposed in the second proximal end position is referred to as a "third proximal end position" (refer to FIG. 14 to FIG. 16, to be described later), and a position of the moving member 73A when the moving member 51B is disposed in the second distal end position is referred to as a "third proximal end position" (refer to FIG. 19 to FIG. 22, to be described later). An intermediate position between the third proximal end position and the third distal end position is referred to as a "third intermediate position" (refer to FIG. 17 and FIG. 18, to be described later). In the initial state in which the hemostatic device 10 is not being used, the moving member 73A is disposed in the third proximal end position. A region through which the moving member 73A passes when moving in the extending direction is referred to as a "first movement region."

Figure 9:
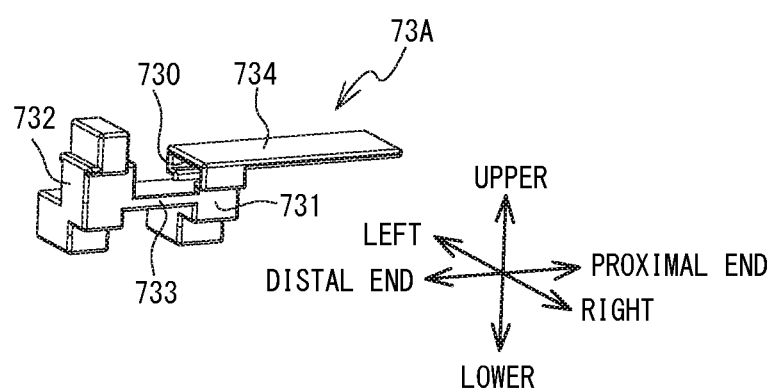
FIG. 9 is a perspective view of a moving member 73A.

As shown in FIG. 9, the moving member 73A includes base sections 731 and 732, a bridge section 733, and the extension section 734.

The base sections 731 and 732 each have a shape formed by a plurality of cuboid bodies coupled together. The second engagement section 730, which is a through hole penetrating a section, in the extending direction, between a surface on the distal end side and a surface on the proximal end side, is provided on the upper end section of the base section 731. The plate-shaped extension section 734 extends from the upper side of the second engagement section 730 of the base section 731 toward the proximal end side. The base section 732 is disposed on the distal end side of the base section 731, with a gap therebetween. The upper end section of the base section 732 is connected to the lower surface of the proximal end section of the moving member 51B of the lever module 51 (refer to FIG. 5). The bridge section 733 has a plate shape, and extends in the extending direction. The proximal end section of the bridge section 733 is connected to the surface on the distal end side of the base section 731. The distal end section of the bridge section 733 is connected to the surface on the proximal end side of base section 732.

As shown in FIG. 5, in the state in which the moving member 73A is disposed in the third proximal end position, the extension section 726 of the switching member 72B disposed in the first intermediate position is inserted, from the proximal end side, through the second engagement section 730. Further, a limiting section 723 of the restricting member 72A to be described later can be inserted through and engage with the second engagement section 730, from the distal end side. In addition, the extension section 734 of the moving member 73A is inserted, from the distal end side, through a gap between the first portion 727A and the third portion 727C of the extension section 727 of the switching member 72B. Note that the switching member 72B is switched from the first intermediate position to the first distal end position by the switching member 72B moving from the first intermediate position toward the distal end side, until the distal end of the extension section 734 of the moving member 73A comes into contact with the second portion 727B.

As shown in FIG. 6, in a state in which the moving member 73A (refer to FIG. 5) is disposed in the third distal end position, the moving member 73A is separated to the distal end side from the switching member 72B. In this case, the extension section 726 of the switching member 72B is not inserted through the second engagement section 730 of the moving member 73A. Further, the extension section 734 (refer to FIG. 5) of the moving member 73A is not inserted through the gap between the first portion 727A and the third portion 727C of the extension section 727 of the switching member 72B. In this state, the switching member 72B elastically deforms such that the gap between the first portion 727A and the third portion 727C becomes smaller, and the protruding section 727D can be disengaged from the restriction wall 710A. In a state in which the protruding section 727D is disengaged from the restriction wall 710A, the switching member 72B moves from the first intermediate position toward the proximal end side, until the base section 725 comes into contact with the proximal end wall 710B of the housing 71. In this way, the switching member 72B switches from the first intermediate position to the first proximal end position.

Restricting Member 72A

Figure 10:
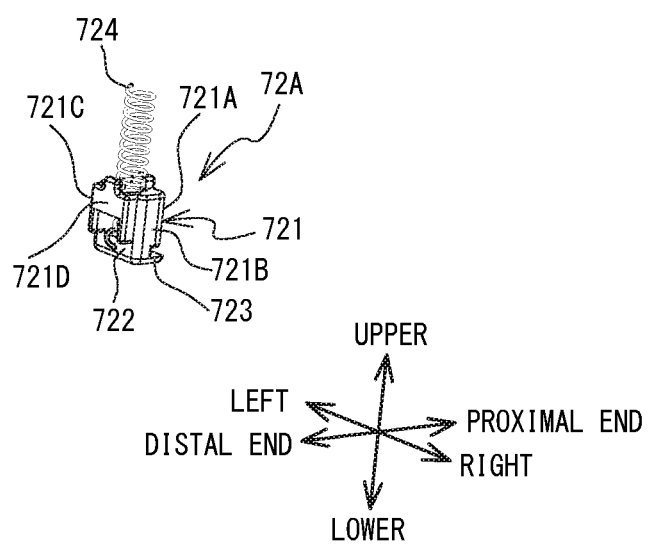
FIG. 10 is a perspective view of the restricting member 72A.

As shown in FIG. 2 and FIG. 3, the restricting member 72A is disposed below the protruding section 711A of the housing 71. The restricting member 72A moves up and down in accordance with an urging force of an urging section 724 to be described later (refer to FIG. 10). As shown in FIG. 10, the restricting member 72A includes a base section 721, an extension section 722, the limiting section 723, and the urging section 724.

The base section 721 includes a first portion 721A, second portions 721B and 721C, and a third portion 721D. On the proximal end side, the first portion 721A has a surface orthogonal to the extending direction. The second portion 721B extends to the distal end side from the right end section of the first portion 721A, and has a surface, on the right side thereof, that is orthogonal to the left-right direction. The second portion 721C extends to the distal end side from the left end section of the first portion 721A, and has a surface, on the left side thereof, that is orthogonal to the left-right direction. The third portion 721D is provided between the respective distal end sections of the second portions 721B and 721C. The urging section 724 is a tension coil spring. The lower end section of the urging section 724 is connected to the base section 721, inside a hole surrounded by the respective surfaces of the first portion 721A, the second portions 721B and 721C, and the third portion 721D. The upper end section of the urging section 724 is connected to an inner wall on the upper side of the protruding section 711A (refer to FIG. 1 to FIG. 3) of the housing 71. The urging force in the upward direction, which results from the elastic force of the urging section 724, acts on the restricting member 72A. The extension section 722 extends downward from the base section 721. The limiting section 723 has a plate shape, and protrudes to the proximal end side from the lower end section of the extension section 722.

As shown in FIG. 5, in a state in which the base section 721 has moved downward in resistance to the urging force of the urging section 724, the limiting section 723 is disposed in the first movement region of the moving member 73A. In this state, from the distal end side, the limiting section 723 is inserted through and engages with the second engagement section 730 of the moving member 73A disposed in the third proximal end position. When the limiting section 723 is engaged with the moving member 73A, the upward movement of the restricting member 72A as a result of the urging force of the urging section 724 is restricted. Further, in this state, the movement of the moving member 73A from the third proximal end position toward the third distal end position is restricted by the limiting section 723. Therefore, the movement of the moving member 51B, which is connected to the moving member 73A, from the second proximal end position toward the second intermediate position is also restricted, and furthermore, the movement of the push-out member 8B (refer to FIG. 7), which is connected to the moving member 51B, is also restricted. Hereinafter, a state in which the limiting section 723 has engaged with the second engagement section 730 of the moving member 73A and has restricted the movement of the moving member 51B is referred to as a "restricting state."

When the restricting member 72A is in the restricting state, when the switching member 72B has moved to the distal end side from the first intermediate position toward the first distal end position, the extension section 726 of the switching member 72B protrudes to the distal end side from the second engagement section 730 of the moving member 73A. As a result of this, the state of engagement of the limiting section 723 with the second engagement section 730 of the moving member 73A is released. In this case, the base section 721 of the restricting member 72A moves upward in accordance with the urging force of the urging section 724 (refer to FIG. 6). In this way, the limiting section 723 of the restricting member 72A is no longer disposed in the first movement region of the moving member 73A. In this state, the movement of the moving member 73A is not restricted by the limiting section 723, and thus, the moving member 73A can move in the extending direction through the first movement region. In this way, the moving member 51B connected to the moving member 73A can also move in the extending direction. Hereinafter, a state in which the limiting section 723 is not engaged with the second engagement section 730 of the moving member 73A, and the movement of the moving member 51B is not restricted is referred to as an "enabling state."

Moving Member 73B

Figure 11:
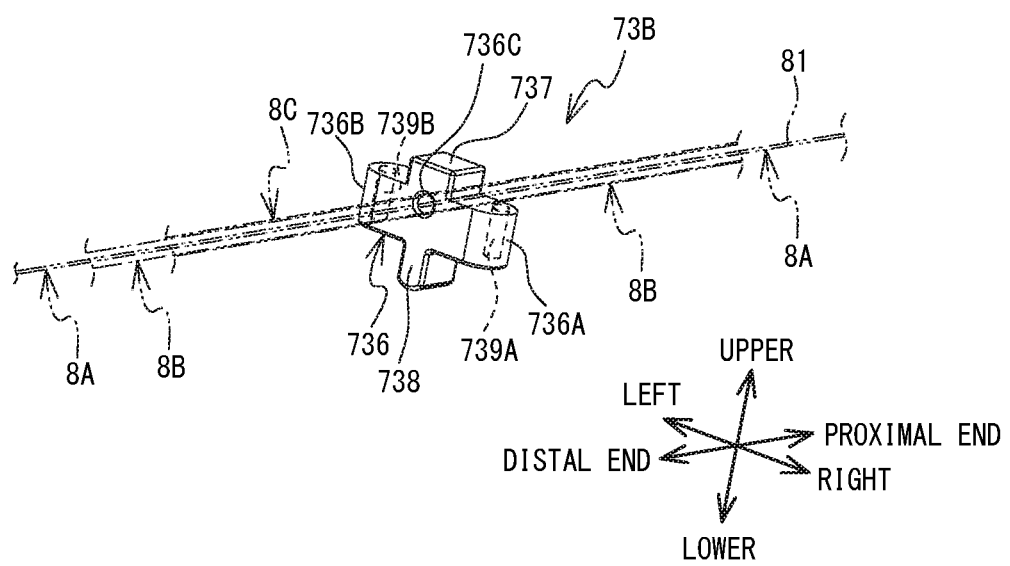
FIG. 11 is a perspective view of a moving member 73B.

As shown in FIG. 3, the moving member 73B is disposed below the lever module 51 inside the housing 71. The moving member 73B moves in the extending direction in accordance with the operation of the first operation unit 510, and causes the first tubular member 8C to move in the extending direction. Hereinafter, a position of the moving member 73B that has moved furthest to the proximal end side is referred to as a "fourth proximal end position" (refer to FIG. 14 to FIG. 16), and a position of the moving member 73B that has moved furthest to the distal end side is referred to as a "fourth distal end position" (refer to FIG. 17 to FIG. 22). In the initial state in which the hemostatic device 10 is not being used, the moving member 73B is disposed in the fourth proximal end position. As shown in FIG. 11, the moving member 73B includes a base section 736 and extension sections 737 and 738.

The base section 736 is a substantially cuboid shape that is long in the left-right direction. The extension section 737 protrudes upward from the center, in the left-right direction, of the upper section of the base section 736. The extension section 738 protrudes downward from the center, in the left-right direction, of the lower end section of the base section 736. The extension section 738 is disposed in an internal space of the protruding section 711B of the housing 71 (refer to FIG. 1 to FIG. 3), and moves in the extending direction along the internal space. When the moving member 73B is disposed in the fourth proximal end position, the extension section 738 is disposed in the proximal end section of the internal space of the protruding section 711B. When the moving member 73B is disposed in the fourth distal end position, the extension section 738 is disposed in the distal end section of the internal space of the protruding section 711B. The base section 736 has a magnet 739A that is built into a portion 736A further to the right side than the extension sections 737 and 738, and a magnet 739B that is built into a portion 736B further to the left side than the extension sections 737 and 738.

A through hole 736C that extends in the extending direction is formed in the center of the base section 736. The proximal end section of the first tubular member 8C is connected around the periphery of the through hole 736C, of the surface of the distal end side of the base section 736. The first tubular member 8C extends to the distal end side from the base section 736. The extending section 81 of the positioning member 8A extending to the distal end side from the switching member 72B (refer to FIG. 6), and the push-out member 8B extending to the distal end side from the moving member 51B (refer to FIG. 7) are inserted through the through hole 736C, from the proximal end side. The extending section 81 of the positioning member 8A, and the push-out member 8B pass through the through hole 736C and extend further to the distal end side than the base section 736, and pass through the lumen of the first tubular member 8C.

Moving Member 74B

Figure 12:
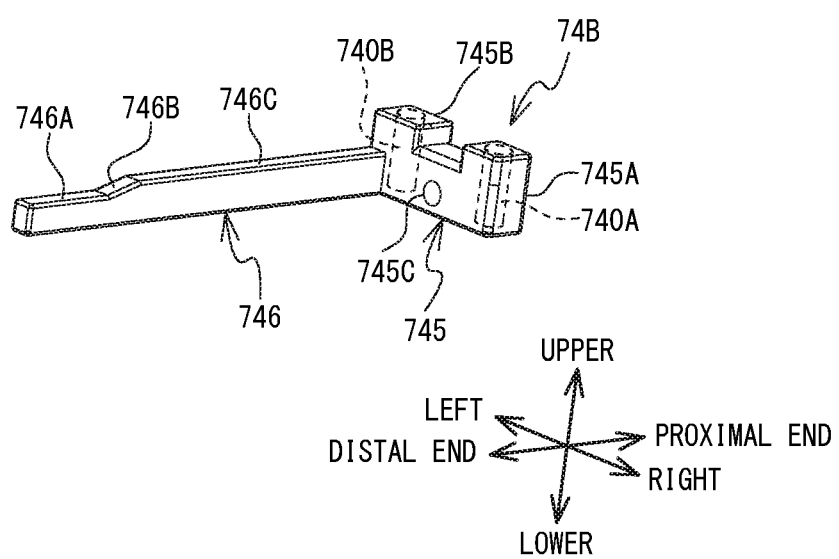
FIG. 12 is a perspective view of a moving member 74B.

As shown in FIG. 2 and FIG. 3, the moving member 74B is disposed further to the distal end side than the moving member 73B inside the housing 71. The moving member 74B moves in the extending direction in accordance with the operation of the first operation unit 510, and switches a state of the restricting mechanism 74C to be described later (refer to FIG. 13). Hereinafter, a position of the moving member 74B that has moved furthest to the proximal end side is referred to as a "fifth proximal end position" (refer to FIG. 14 to FIG. 18), and a position of the moving member 74B that has moved furthest to the distal end side is referred to as a "fifth distal end position" (refer to FIG. 19 to FIG. 22). In the initial state in which the hemostatic device 10 is not being used, the moving member 74B is disposed in the fifth proximal end position (refer to FIG. 14 to FIG. 18). As shown in FIG. 12, the moving member 74B includes a base section 745 and an extending section 746.

The base section 745 is a substantially cuboid shape that is long in the left-right direction. A recessed section that is recessed downward is provided in the center, in the left-right direction, of the upper end section of the base section 745. In the base section 745, a magnet 740A is built into a portion 745A further to the right side of the recessed section, and a magnet 740B is built into a portion 745B further to the left side of the recessed section. The extending section 746 has a plate shape, and extends to the distal end side from the left end section of the base section 745. The upper end section of the extending section 746 is provided with a first portion 746A, a second portion 746B, and a third portion 746C. The first portion 746A extends in the extending direction from the distal end section of the extending section 746 toward the proximal end side. The second portion 746B extends while being inclined diagonally upward, from the proximal end section of the first portion 746A toward the proximal end side. The third portion 746C extends in the extending direction from the proximal end section of the second portion 746B toward the proximal end side.

A through hole 745C that extends in the extending direction is formed below the recessed section in the base section 745. The extending section 81 of the positioning member 8A that extends to the distal end side from the switching member 72B (refer to FIG. 6), the push-out member 8B that extends to the distal end side from the moving member 51B (refer to FIG. 7), and the first tubular member 8C that extends to the distal end side from the moving member 73B (refer to FIG. 11) are inserted, from the proximal end side, through the through hole 745C. The extending section 81 of the positioning member 8A, the push-out member 8B, and the first tubular member 8C pass through the through hole 745C and extend further to the distal end side than the base section 745.

Coupling Section 71C

As shown in FIG. 3, the coupling section 71C is provided in the distal end section of the housing 71. The coupling section 71C moves in accordance with the operation of the second operation unit 520, and causes the second tubular member 8D to move in the extending direction. Hereinafter, a position of the coupling section 71C that has moved furthest to the proximal end side is referred to as a "sixth proximal end position" (refer to FIG. 14 to FIG. 20), and a position of the coupling section 71C that has moved furthest to the distal end side is referred to as a "sixth distal end position" (refer to FIG. 21 and FIG. 22). The movement of the coupling section 71C can be restricted by the restricting mechanism 74C to be described later (refer to FIG. 13). As shown in FIG. 3, the coupling section 71C includes a tubular section 716, an extension section 717, and a protruding section 718.

The tubular section 716 is a tubular member that has a lumen extending in the extending direction. The tubular section 716 includes a distal end tubular section 716A and a proximal end tubular section 716B that are aligned in the extending direction. The distal end tubular section 716A is disposed on the distal end side with respect to the proximal end tubular section 716B. The diameter of the distal end tubular section 716A is larger than the diameter of the proximal end tubular section 716B. The second tubular member 8D is removably connected to the distal end section of the distal end tubular section 716A, via a connector 88 (refer to FIG. 14). The extending section 81 of the positioning member 8A, the push-out member 8B, and the first tubular member 8C pass through the lumen of the second tubular member 8D and extend further to the distal end side.

The extension section 717 has a long, thin plate shape. The extension section 717 extends to the proximal end side from the upper end section of the distal end tubular section 716A. The protruding section 718 protrudes to the right from the proximal end section of the proximal end tubular section 716B. The proximal end section of the extension section 717 is connected to the protruding section 718. The proximal end sections of each of the proximal end tubular section 716B and the extension section 717 are inserted, from the distal end side, through a through hole provided in the distal end section of the housing 71. When the coupling section 71C has moved to the distal end side, the protruding section 718 is caught on the inner wall of the housing 71. In this way, the coupling section 71C is inhibited from becoming disengaged from the housing 71.

As shown in FIG. 2, a plate-shaped bridge section 52 is connected to the right end section of the protruding section 718. The bridge section 52 extends to the proximal end side from the protruding section 718. The second operation unit 520 is connected to the base section of the bridge section 52. A force generated in accordance with the operation of the second operation unit 520 is transmitted to the coupling section 71C via the bridge section 52, and causes the coupling section 71C to move in the extending direction.

Restricting Mechanism 74C

Figure 13:
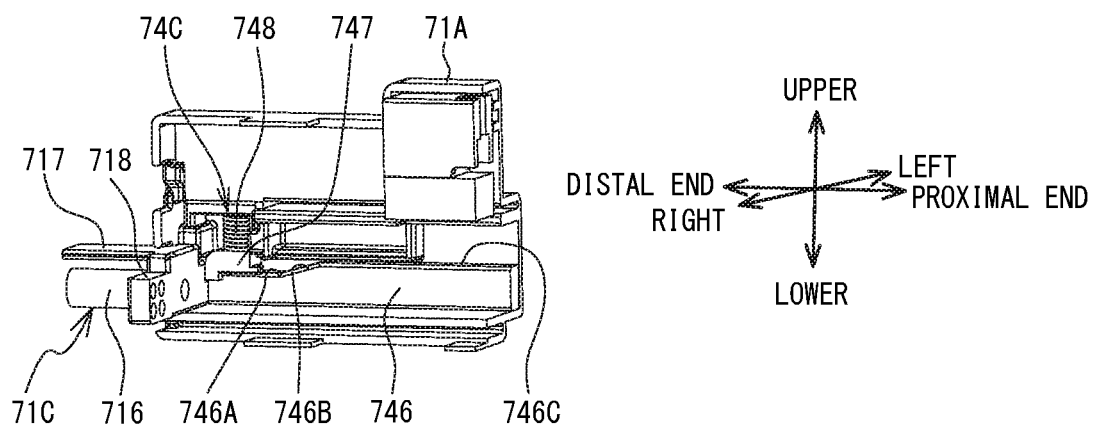
FIG. 13 is a perspective view of a coupling section 71C.

As shown in FIG. 13, inside the housing 71, the restricting mechanism 74C is disposed further to the left side than the proximal end tubular section 716B (refer to FIG. 1 to FIG. 3) of the coupling section 71C, and higher than the extending section 746 (refer to FIG. 12) of the moving member 74B. The restricting mechanism 74C includes a limiting section 747 and an urging section 748. The limiting section 747 is a substantially cuboid shape. The urging section 748 is disposed above the limiting section 747. The urging section 748 is a compression coil spring. The upper end section of the urging section 748 is connected to the inner wall of the housing 71. The lower end section of the urging section 748 is connected to the upper end section of the limiting section 747. An urging force in the downward direction, which results from the elastic force of the urging section 748, acts on the limiting section 747.

FIG. 13 shows a state in which the moving member 74B is disposed in the fifth proximal end position. In this state, the limiting section 747 of the restricting mechanism 74C is in contact with the first portion 746A of the extending section 746 of the moving member 74B. The limiting section 747 is pressed, from above, against the first portion 746A of the extending section 746, in accordance with the urging force of the urging section 748. Hereinafter, a position, in the up-down direction, of the limiting section 747 in the state in which the limiting section 747 is in contact with the first portion 746A of the extending section 746 of the moving member 74B is referred to as a "restricting position." The limiting section 747 in the state of being disposed in the restricting position comes into contact with the surface on the proximal end side of the protruding section 718 of the coupling section 71C that is in the state of being disposed in the sixth distal end position. In this case, the limiting section 747 is disposed in a movement region in the extending direction of the protruding section 718 of the coupling section 71C (hereinafter referred to as a "second movement region"), and thus, the movement of the coupling section 71C to the proximal end side is restricted by the limiting section 747. Note that, in the initial state in which the hemostatic device 10 is not being used, the limiting section 747 is disposed in the restricting position.

In the course of the moving member 74B moving from the fifth proximal end position to the fifth distal end position, the limiting section 747 of the restricting mechanism 74C *comes* into contact, in order, with the first portion 746A, the second portion 746B, and the third portion 746C of the extending section 746 of the moving member 74B, and moves upward in resistance to the urging force of the urging section 748. When the moving member 74B is disposed in the fifth distal end position, the limiting section 747 of the restricting mechanism 74C is in contact with the third portion 746C of the extending section 746 of the moving member 74B. Hereinafter, a position, in the up-down direction, of the limiting section 747 in a state in which the limiting section 747 is in contact with the third portion 746C of the extending section 746 of the moving member 74B is referred to as an "enabling position." The limiting section 747 that is disposed in the enabling position is disposed higher than the limiting section 747 that is disposed in the restricting position. The limiting section 747 in the state of being disposed in the enabling position is disposed higher than the second movement region. In this case, the movement in the extending direction of the coupling section 71C is not restricted by the limiting section 747.

Hemostasis Operation

An operation of hemostasis of the puncture hole by the hemostatic agent S, using the hemostatic device 10, will be explained with reference to FIG. 14 to FIG. 22. When performing medical treatment via a puncture hole 61 (refer to FIG. 14, and the like), a guide wire is inserted into a blood vessel 6 (refer to FIG. 14, and the like) via the puncture hole 61. Next, the second tubular member 8D is inserted into the puncture hole 61 along the guide wire. The second distal end 86 of the second tubular member 8D is disposed inside the blood vessel 6, via an opening 6A (refer to FIG. 14, and the like) formed in the blood vessel 6.

Figure 14:
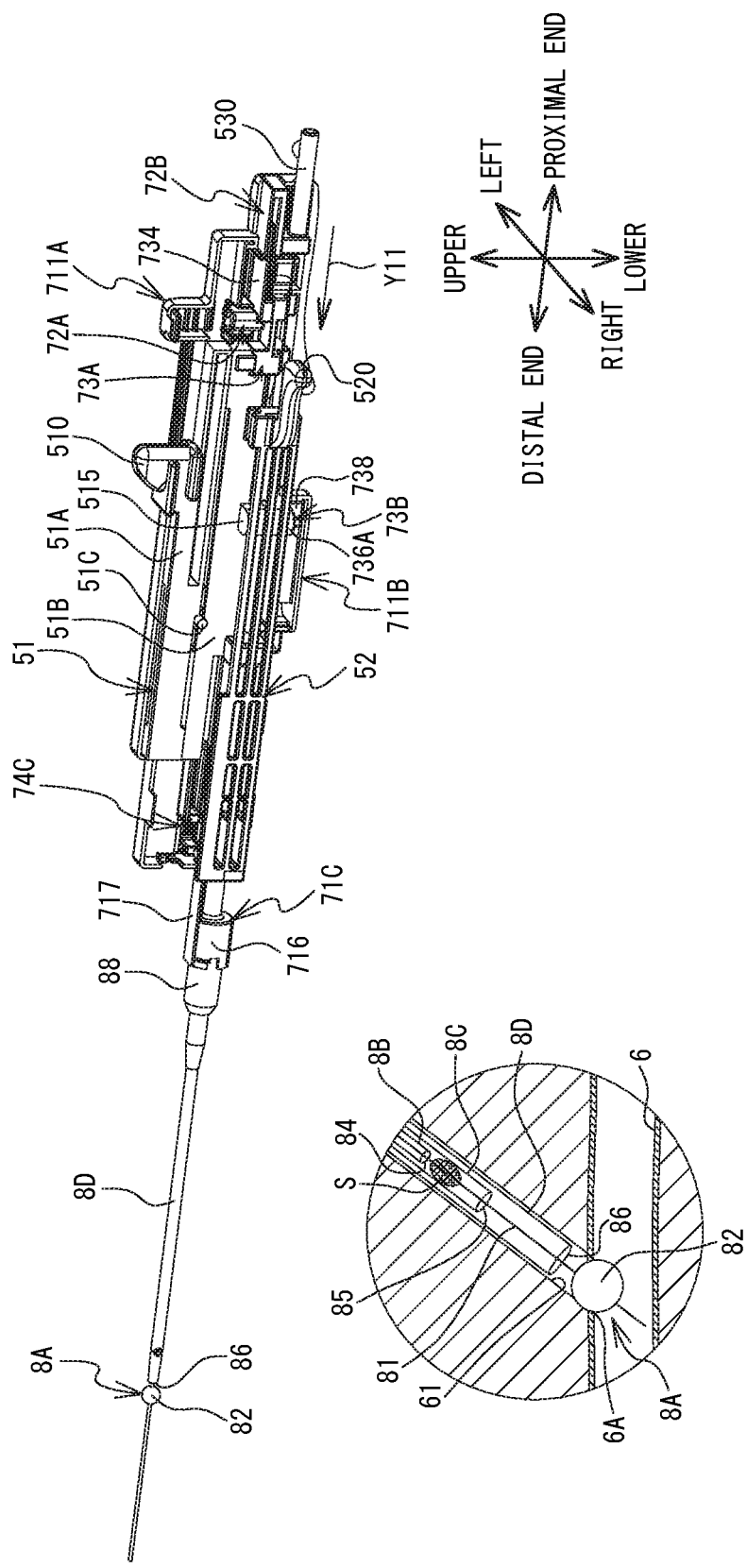
FIG. 14 is a perspective view showing an initial state of a hemostasis operation.
Figure 15:
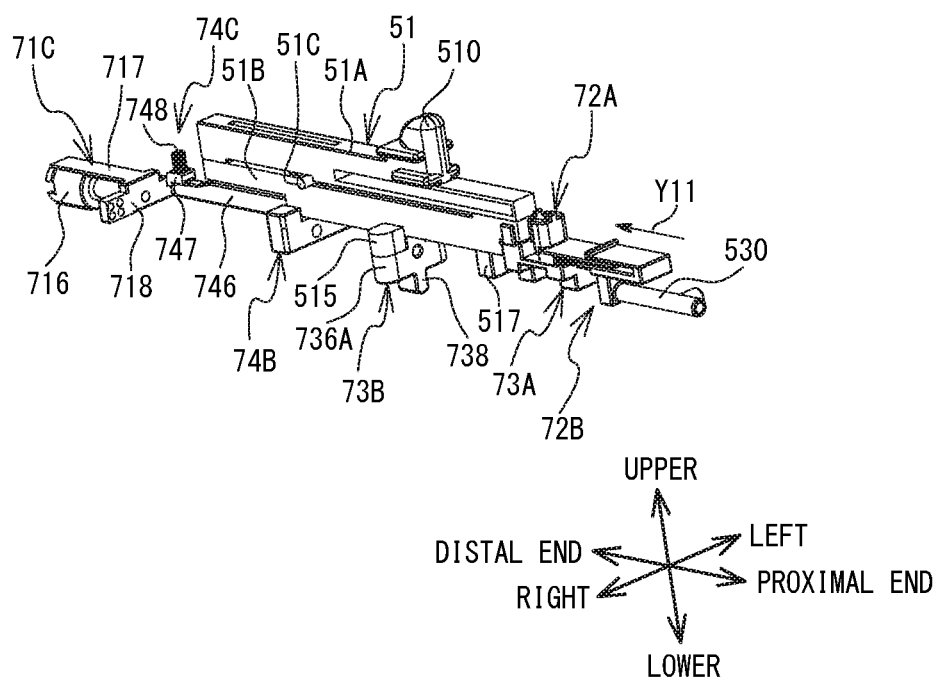
FIG. 15 is a perspective view showing a state of each of the moving members in a state shown in FIG. 14.

After the medical treatment is complete, as shown in FIG. 14 and FIG. 15, the hemostatic device 10 is prepared in which the restricting member 72A is in the restricting state, the switching member 72B is in the first intermediate position, the moving member 51B of the lever module 51 is in the second proximal end position, the moving member 73A is in the third proximal end position, the moving member 73B is in the fourth proximal end position, the moving member 74B is in the fifth proximal end position, and the coupling section 71C is in the sixth distal end position, respectively.

The portion 736A of the moving member 73B is disposed below the protruding section 515 of the moving member 51B of the lever module 51. A force of attraction acts between the magnet 515A (refer to FIG. 7) built into the protruding section 515, and the magnet 739A (refer to FIG. 11) built into the portion 736A. Similarly, although not shown in the drawings, the portion 736B (refer to FIG. 11) of the moving member 73B is disposed below the protruding section 516 (refer to FIG. 20) of the moving member 51B of the lever module 51. A force of attraction acts between the magnet 516A (refer to FIG. 20) built into the protruding section 516, and the magnet 739B (refer to FIG. 11) built into the portion 736B.

As shown in FIG. 15, when the hemostatic device 10 is in the above-described state, the restricting member 72A is in the restricting state, and thus, the limiting section 723 (refer to FIG. 10) of the restricting member 72A engages, from the distal end side, with the second engagement section 730 (refer to FIG. 9) of the moving member 73A and is disposed in the first movement region of the moving member 73A. As a result, the movement of the moving member 73A in the extending direction is restricted by the limiting section 723. Thus, the movement of the push-out member 8B (refer to FIG. 7), which is connected to the moving member 51B via the moving member 73A, is also restricted. Further, since the moving member 74B is disposed in the fifth proximal end position, the limiting section 747 of the restricting mechanism 74C is disposed in the restricting position. Thus, the movement to the proximal end side of the coupling section 71C disposed in the sixth distal end position is restricted by the restricting mechanism 74C.

Pre-Operation

As shown in FIG. 14, the positioning member 8A, the hemostatic agent S, the push-out member 8B, and the first tubular member 8C of the hemostatic device 10 are inserted through the second tubular member 8D that is disposed in the puncture hole 61. After that, the connector 88 of the second tubular member 8D is caused to come into contact with the coupling section 71C of the hemostatic device 10. The first engagement section 82 of the positioning member 8A protrudes to the distal end side from the second distal end 86 of the second tubular member 8D, and is disposed inside the blood vessel 6. The hemostatic agent S, the push-out member 8B, and the first tubular member 8C are disposed inside the second tubular member 8D. The second distal end 86 of the second tubular member 8D, the first distal end 85 of the first tubular member 8C, the hemostatic agent S, and the push-out distal end 84 of the push-out member 8B are arranged, in this order, from the first engagement section 82 of the positioning member 8A toward the proximal end side.

Next, in accordance with the compressed fluid being supplied from the hub, the first engagement section 82 of the positioning member 8A expands inside the blood vessel 6. In this state, the user holds the housing 71 of the hemostatic device 10 and applies pressure, and moves the housing 71 toward a side (the proximal end side) in which the second tubular member 8D is pulled out from the puncture hole 61. In this way, the first engagement section 82 that is expanded inside the blood vessel 6 engages, from the inside, with the opening 6A formed in the blood vessel 6. The user moves the housing 71 further to the proximal end side. In this way, the positioning member 8A moves relatively to the distal end side with respect to the housing 71, and, as shown in FIG. 14 and FIG. 15, the switching member 72B that is connected to the positioning member 8A also moves relatively to the distal end side with respect to the moving member 73A (refer to an arrow Y11 in FIG. 14 and FIG. 15).

Figure 16:
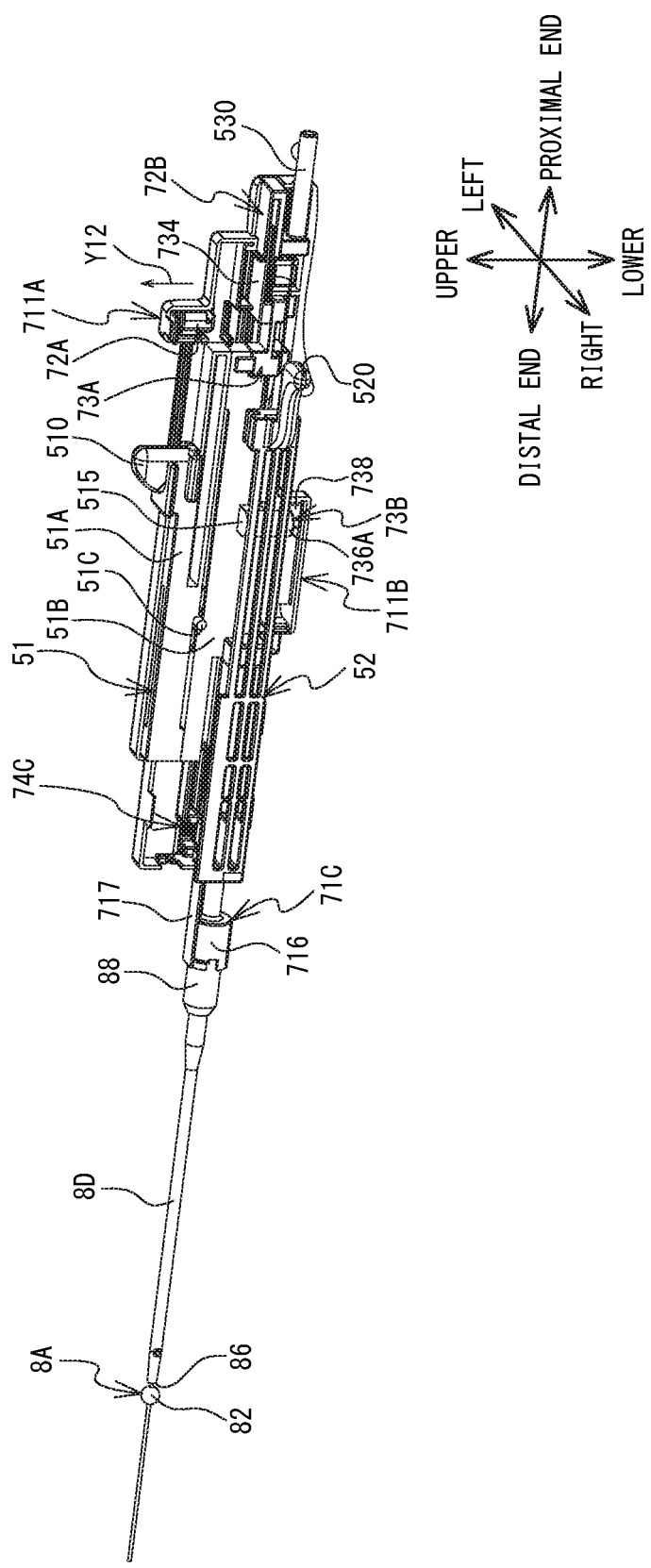
FIG. 16 is a perspective view showing a case in which the restricting member 72A is in the enabling state.

When the switching member 72B has moved from the first intermediate position to the first distal end position, the extension section 726 (refer to FIG. 4) of the switching member 72B protrudes to the distal end side from the second engagement section 730 (refer to FIG. 9) of the moving member 73A. In this way, the engagement of the limiting section 723 with the second engagement section 730 of the moving member 73A is released. In this case, as shown in FIG. 16, the restricting member 72A moves upward (an arrow Y12) in accordance with the urging force of the urging section 724 (refer to FIG. 10), and the restricting member 72A switches from the restricting position to the enabling position. The limiting section 723 is no longer disposed in the first movement region of the moving member 73A, and thus, the moving member 73A is in a state of being able to move through the first movement region.

Note that after the position of the restricting member 72A has once switched from the restricting state to the enabling state, even if the force applied to the housing 71 by the user is released, the restricting member 72A does not return to the original restricting state. In other words, when the engagement of the limiting section 723 with the moving member 73A is once released and the restricting member 72A is in the enabling state, the restricting member 72A is maintained in the enabling state, and does not return to the original restricting state.

First Distal End Operation

Figure 17:
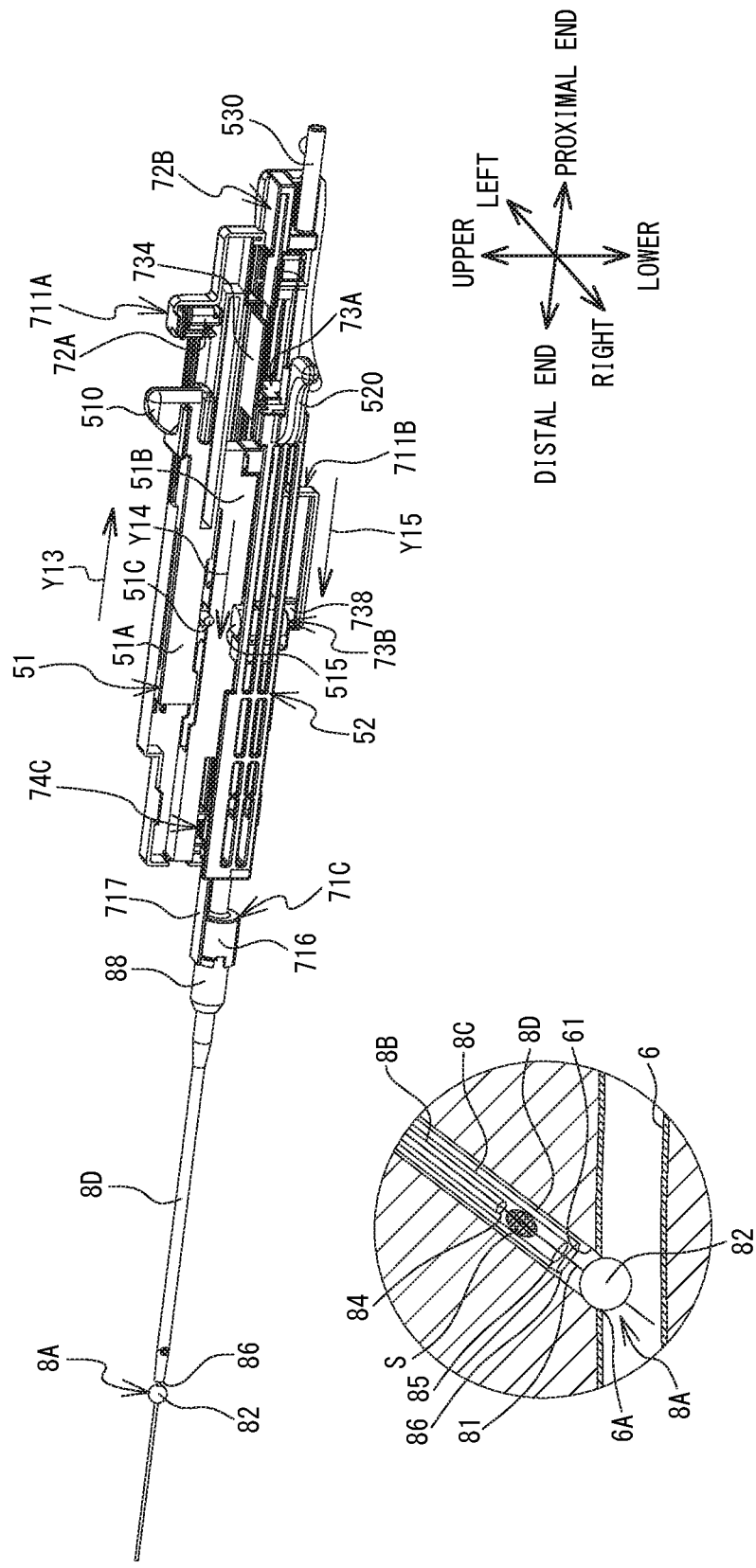
FIG. 17 is a perspective view showing a first distal end operation.

In the hemostatic device 10, when the restricting member 72A is in the enabling state, the moving member 73A can move in the extending direction. As shown in FIG. 17, in this state, the user performs an operation to move the first operation unit 510 to the proximal end side (refer to an arrow Y13). In accordance with the rotation of the pinion gear 51C of the lever module 51, the moving member 51B moves to the distal end side from the second proximal end position to the second intermediate position (an arrow Y14). Further, a force of attraction acts between the magnets 515A (refer to FIG. 7) and 739A (refer to FIG. 11), and between the magnets 516A (refer to FIG. 20) and 739B (refer to FIG. 11). As a result, in accordance with the movement of the moving member 51B, the moving member 73B moves, while maintaining contact with the moving member 51B, to the distal end side from the fourth proximal end position to the fourth distal end position (an arrow Y15).

In accordance with the movement to the distal end side of the moving member 51B, the push-out member 8B that has come into contact with the protruding section 517 (refer to FIG. 7) moves to the distal end side. Further, in accordance with the movement of the moving member 73B to the distal end side, the first tubular member 8C that has come into contact with the base section 736 (refer to FIG. 11) moves to the distal end side. Note that, since the switching member 72B is maintained in the first distal end position, the positioning member 8A that has come into contact with the base section 725 does not move even when the first operation unit 510 is operated. In other words, the push-out member 8B and the first tubular member 8C move relatively to the distal end side with respect to the housing 71 and the positioning member 8A. Hereinafter, the above-described operation resulting from the operation of the first operation unit 510 is referred to as a "first distal end operation." In the first distal end operation, disengagement of the moving members 51B and 73B is restricted by the magnets 515A, 516A, 739A and 739B, and thus, only the positioning member 8A is restricted from moving to the distal end side. As a result of the first distal end operation, the hemostatic agent S is pressed to the distal end side by the push-out member 8B in a state in which the hemostatic agent S is disposed in the vicinity of the first distal end 85 inside the first tubular member 8C, and the hemostatic agent S moves to the vicinity of the second distal end 86 of the second tubular member 8D.

Figure 18:
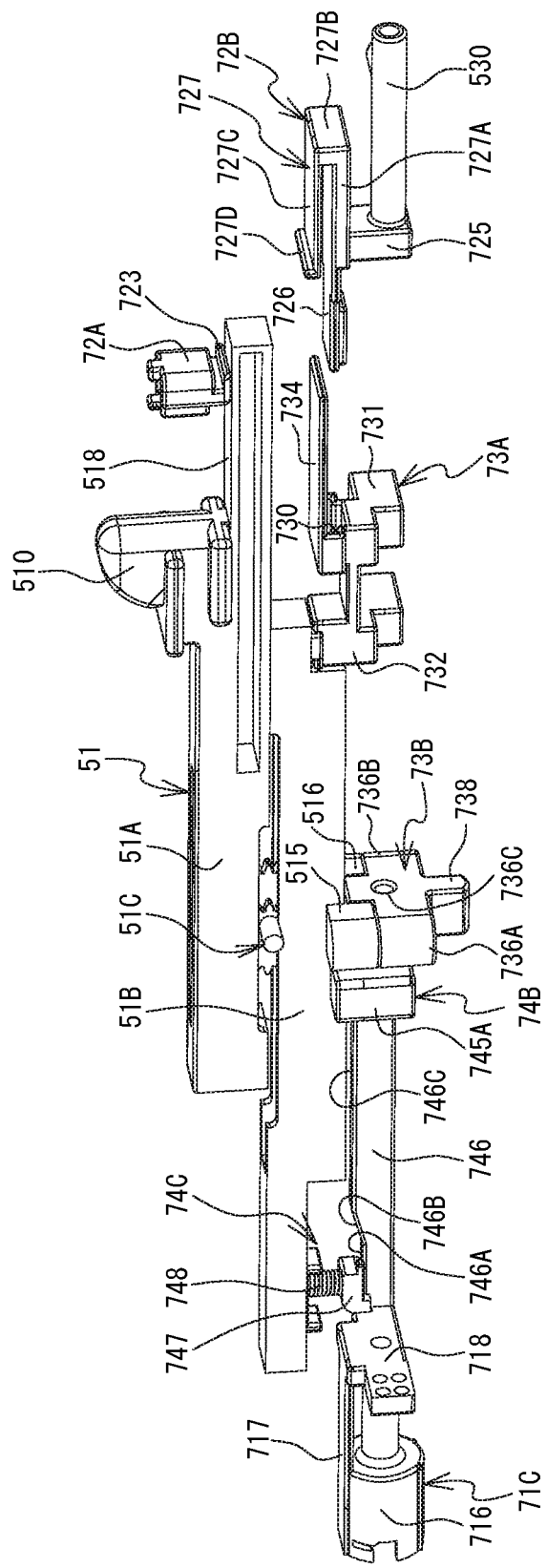
FIG. 18 is a perspective view showing a state of each of the moving members in a state shown in FIG. 17.

In accordance with the movement to the distal end side of the moving member 73B from the fourth proximal end position, the extension section 738 moves to the distal end side from the vicinity of the proximal end section along the internal space inside the protruding section 711B of the housing 71. When the moving member 73B has moved to the fourth distal end position, the protruding section 738 is disposed in the vicinity of the distal end section of the internal space of the protruding section 711B. As shown in FIG. 18, the protruding sections 515 and 516 of the moving member 51B, and the moving member 73B come into contact with the proximal end section of the moving member 74B disposed in the fifth proximal end position. Note that the movement of the moving member 73B further to the distal end side is restricted by the protruding section 738 coming into contact, from the proximal end side, with distal end section of the inner wall of the protruding section 711B (refer to FIG. 17).

Of the moving member 51A of the lever module 51, the proximal end section 518 that is further to the proximal end side than the first operation unit 510 is disposed below the restricting member 72A in the enabling state. The proximal end section 518 inhibits the restricting member 72A from moving downward from the enabling state and returning to the original restricting state.

The moving member 73A moves from the third proximal end position to the third intermediate position in accordance with the movement of the moving member 51B. The extension section 734 of the moving member 73A switches from the state of being inserted into the gap between the first portion 727A and the third portion 727C of the extension section 727 of the switching member 72B to the state in which it is not inserted therebetween. The second portion 727B of the extension section 727 of the switching member 72B can elastically deform such that the gap between the first portion 727A and the third portion 727C becomes narrower.

Second Distal End Operation

Figure 19:
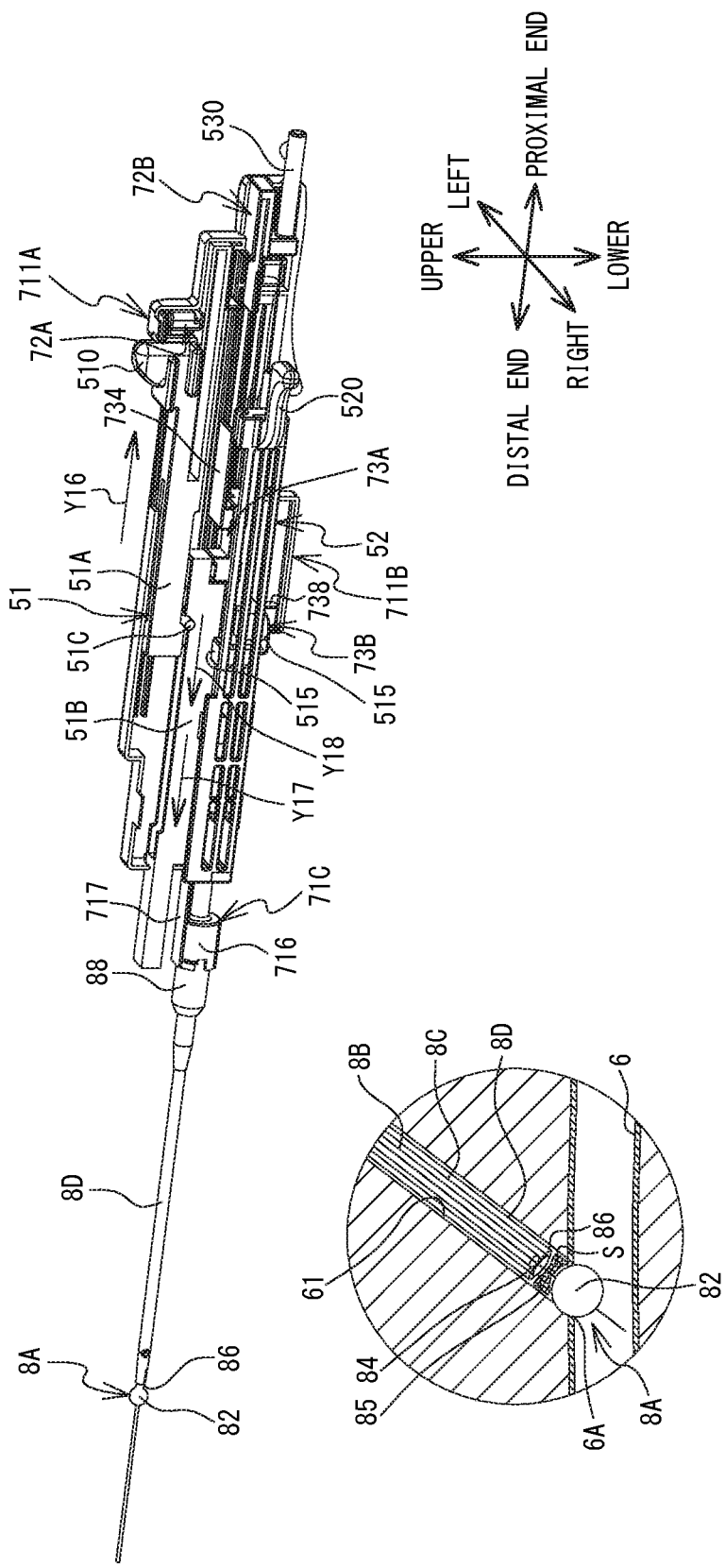
FIG. 19 is a perspective view showing a second distal end operation.

As shown in FIG. 19, next, the user performs an operation to move the first operation unit 510 further to the proximal end side (refer to an arrow Y16). In accordance with the rotation of the pinion gear 51C of the lever module 51, the moving member 51B moves from the second intermediate position to the second distal end position (refer to an arrow Y17). Note that the movement of the moving member 73B to the distal end side is restricted by the extension section 738 coming into contact, from the proximal end side, with the inner wall of the protruding section 711B. The moving member 73B is maintained in the fourth distal end position. Thus, the moving member 51B separates from the moving member 73B, and moves to the distal end side in accordance with the operation of the first operation unit 510. Further, in accordance with the movement of the moving member 51B, the moving member 73A that is in contact with the moving member 51B moves from the third intermediate position to the third distal end position.

In accordance with the moving member 51B moving to the distal end side, the push-out member 8B that is in contact with the protruding section 517 (refer to FIG. 7) moves to the distal end side. On the other hand, the first tubular member 8C that is in contact with the base section 736 (refer to FIG. 11) of the moving member 73B does not move to the distal end side. Further, since the moving member 72B is maintained in the first distal end position, the positioning member 8A that is in contact with the base section 725 (refer to FIG. 4) does not move to the distal end side. In other words, the push-out member 8B moves relatively to the distal end side, with respect to the housing 71, the positioning member 8A, and the first tubular member 8C. Hereinafter, the above-described operation resulting from the operation of the first operation unit 510 is referred to as a "second distal end operation." In the second distal end operation, the disengagement of the moving members 51B and 73B is enabled, and thus, it is possible to cause the push-out member 8B only to move to the distal end side. In other words, until the first distal end operation is complete, the moving members 51B and 73B restrict the second distal end operation, and once the first distal end operation is complete, the restriction on the second distal end operation is released and the second distal end operation can be performed.

As a result of the second distal end operation, the hemostatic agent S is pushed out, to the distal end side, further than the first distal end 85 of the first tubular member 8C, by the push-out distal end 84 of the push-out member 8B. In the vicinity of the second distal end 86 of the second tubular member 8D, the hemostatic agent S is pushed, from the proximal end side, against the first engagement section 82 of the positioning member 8A. In this way, the hemostatic agent S closes the opening 6A of the blood vessel 6 with which the first engagement section 82 engages.

Figure 20:
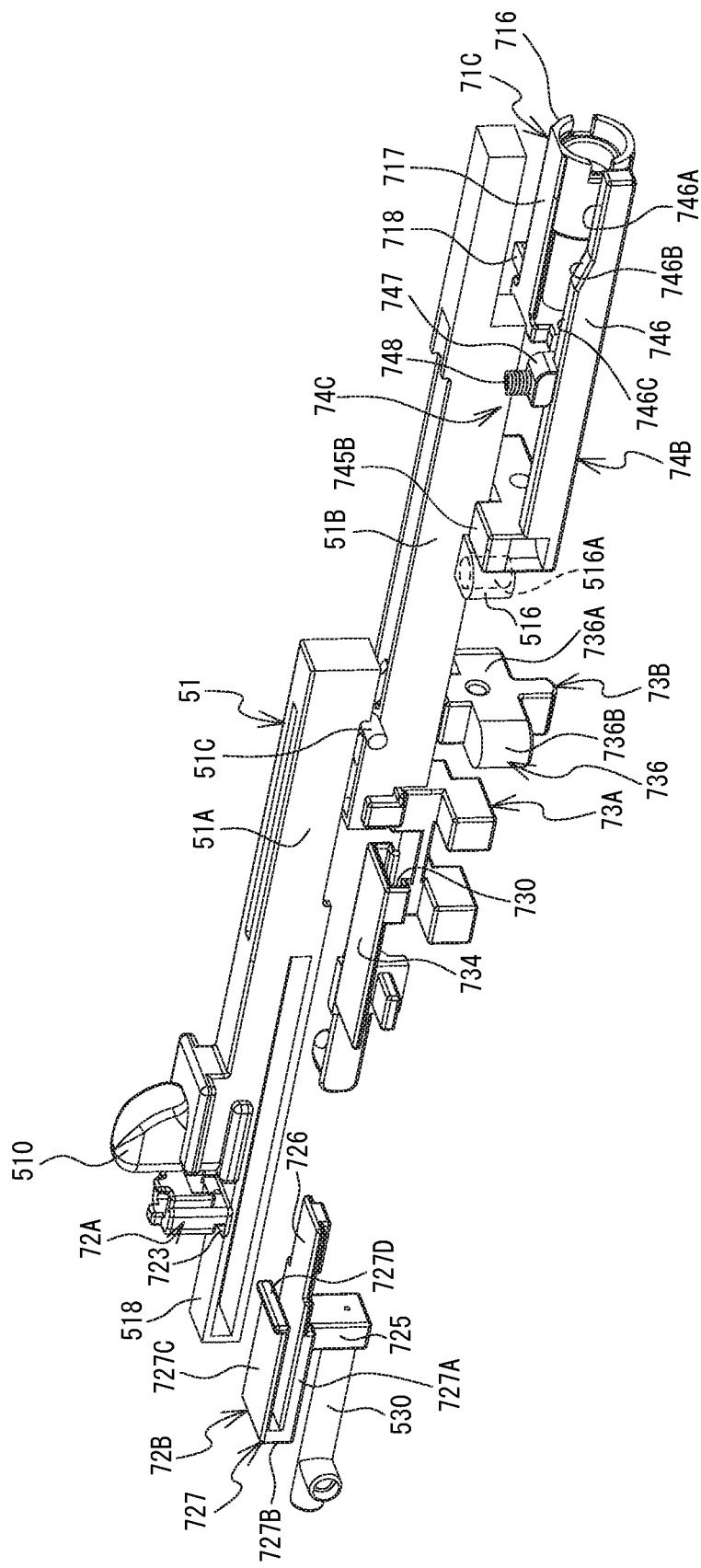
FIG. 20 is a perspective view showing a state of each of the moving members in a state shown in FIG. 19.

As shown in FIG. 20, in accordance with the moving member 51B moving to the second distal end position as a result of the second distal end operation, the moving member 74B is pressed to the distal end side by the protruding sections 515 and 516 of the moving member 51B, and the moving member 74B moves to the distal end side from the fifth proximal end position to the fifth distal end position (refer to an arrow Y18 in FIG. 19). In this way, the limiting section 747 of the restricting mechanism 74C moves from the restricting position (refer to FIG. 13) to the enabling position (refer to FIG. 20). In this case, the limiting section 747 moves from a state of being disposed in the second movement region to a state of not being disposed in the second movement region. As a result, the coupling section 71C can move from the sixth distal end position toward the sixth proximal end position. In other words, in accordance with the push-out member 8B having moved to the distal end side during the second distal end operation, the coupling section 71C is in a state of being able to move relatively to the proximal end side with respect to the housing 71, the positioning member 8A, the push-out member 8B, and the first tubular member 8C.

Coupling Proximal End Operation

As shown in FIG. 21, next, the user performs an operation to move the second operation unit 520 to the proximal end side (refer to an arrow Y19). Note that the second operation unit 520 is connected to the coupling section 71C via the bridge section 52. In addition, the coupling section 71C is in the state of being able to move to the proximal end side from the sixth distal end position to the sixth proximal end position, as a result of the second distal end operation. Thus, in accordance with the operation of the second operation unit 520, the coupling section 71C moves from the sixth distal end position to the sixth proximal end position (refer to an arrow Y20). Hereinafter, the above-described operation resulting from the operation of the second operation unit 520 is referred to as a "coupling proximal end operation." In other words, until the second distal end operation is complete, the coupling proximal end operation is restricted by the limiting section 747 being disposed in the restricting position. On the other hand, the limiting section 747 is switched to the enabling position by the completion of the second distal end operation, and as a result, the restriction on the coupling proximal end operation is released and the coupling proximal end operation can be performed.

By the coupling proximal end operation, the second tubular member 8D coupled to the coupling section 71C moves to the proximal end side. On the other hand, the positioning member 8A connected to the switching member 72B, the push-out member 8B connected to the moving member 51B, and the first tubular member 8C connected to the moving member 73B do not move. In other words, the second tubular member 8D moves relatively to the proximal end side with respect to the housing 71, the positioning member 8A, the push-out member 8B, and the first tubular member 8C. In this case, the second distal end 86 of the second tubular member 8D separates, to the proximal end side, from the hemostatic agent S that is in the state of closing the opening 6A of the blood vessel 6.

Positioning Proximal End Operation

Figure 22:
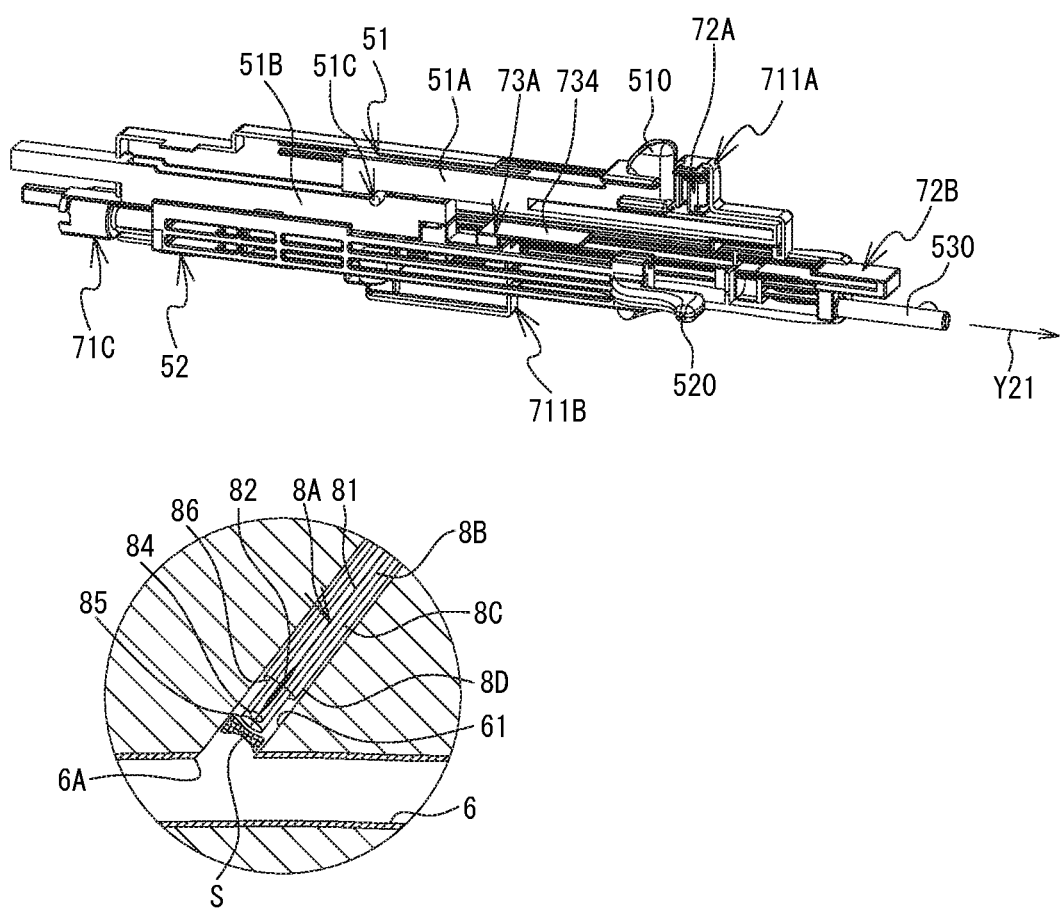
FIG. 22 is a perspective view showing a positioning proximal end operation.

Next, the user removes, via the hub, the compressed fluid supplied to the first engagement section 82, and causes the first engagement section 82 to contract. Next, as shown in FIG. 22, the user performs an operation to relatively move the third operation unit 530 to the proximal end side with respect to the housing 71 (refer to an arrow Y21). Note that the third operation unit 530 is connected to the switching member 72B. The extension section 734 of the moving member 73A is in the state of not being inserted into the gap between the first portion 727A and the third portion 727C of the switching member 72B. Thus, in accordance with the operation of the third operation unit 530, the switching member 72B elastically deforms such that the gap between the first portion 727A and the third portion 727C becomes narrower, and the protruding section 727D (refer to FIG. 5 and FIG. 6) can be disengaged from the restricting wall 710A (refer to FIG. 5 and FIG. 6). In the state in which the protruding section 727D is disengaged from the restricting wall 710A, the switching member 72B moves toward the proximal end side from the first intermediate position, until the base section 725 comes into contact with the proximal end wall 710B of the housing 71. In this way, the switching member 72B moves to the proximal end side from the first intermediate position to the first proximal end position, and the positioning member 8A connected to the switching member 72B also moves to the proximal end side. On the other hand, the push-out member 8B connected to the moving member MB, the first tubular member 8C connected to the moving member 73B, and the second tubular member 8D connected to the coupling section 71C do not move. In other words, the positioning member 8A moves relatively to the proximal end side with respect to the housing 71, the push-out member 8B, the first tubular member 8C, and the second tubular member 8D. Hereinafter, the above-described operation resulting from the operation of the third operation unit 530 is referred to as a "positioning proximal end operation."

As a result of the positioning proximal end operation, the first engagement section 82 of the positioning member 8A moves further to the proximal end side than the push-out distal end 84 of the push-out member 8B, and is disposed inside the push-out member 8B. After that, the positioning member 8A, the hemostatic agent S, the push-out member 8B, the first tubular member 8C, and the second tubular member 8D are removed from the puncture hole 61.

Operations and Effects of First Embodiment

As described above, in the hemostatic device 10, the first distal end operation is performed in the state in which the first engagement section 82 of the positioning member 8A is engaged with the opening 6A of the blood vessel 6. In the first distal end operation, the first tubular member 8C and the push-out member 8B move relatively to the distal end side with respect to the housing 71. As a result, the hemostatic device 10 can move the hemostatic agent S to the distal end side in the state in which the hemostatic agent S is held inside the first tubular member 8C, and can cause the hemostatic agent S to come close to the first engagement section 82 of the positioning member 8A. In the second distal end operation, the push-out member 8B moves relatively to the distal end side with respect to the housing 71 and the first tubular member 8C. As a result, the hemostatic device 10 pushes out the hemostatic agent S from the first tubular member 8C using the push-out member 8B, and causes the hemostatic agent S to be exposed in the vicinity of the first engagement section 82. Further, in the second distal end operation, using the push-out member 8B, the hemostatic agent S is pushed as far as a position of being in contact with the first engagement section 82, and the puncture hole 61 including the opening 6A of the blood vessel 6 is closed by the hemostatic agent S.

In the hemostatic device 10, the second distal end operation is restricted until the first distal end operation is complete. As a result, the hemostatic device 10 restricts the second distal end operation from being performed until the first distal end operation is complete. Thus, even when the hemostatic device 10 is erroneously operated, it is possible to inhibit the hemostatic agent S from being pushed out from the first tubular member 8C before the hemostatic agent S comes close to the first engagement section 82. As a result, the user can easily and reliably operate 018 the hemostatic device 10 to close the opening 6A of the blood vessel 6 using the hemostatic agent S, and stop the bleeding.

The hemostatic device 10 includes the moving member 73B connected to the first tubular member 8C, and the moving member 51B connected to the push-out member 8B. In the first distal end operation, the moving members 51B and 73B move to the distal end side in the state of being in contact with each other. In this way, the push-out member 8B and the first tubular member 8C also move to the distal end side. On the other hand, in the second distal end operation, the moving member 51B moves to the distal end side in the state of being disengaged from the moving member 73B. In this way, the push-out member 8B moves to the distal end side. As a result, using the moving members 51B and 73B, the hemostatic device 10 can easily realize a configuration to realize a function of restricting the second distal end operation until the first distal end operation is complete, and a configuration to realize a function releasing the restriction on the second distal end operation after the first distal end operation is complete.

In the hemostatic device 10, the first distal end operation is performed in accordance with the operation to move the first operation unit 510 to one side in the extending direction (the proximal end side). Further, in the hemostatic device 10, the second distal end operation is performed in accordance with the operation to move the first operation unit 510 further to the one side (the proximal end side) in the extending direction. Thus, simply by performing the operation to move the first operation unit 510 in the same direction (the one side in the extending direction (the proximal end side)), the user can cause the hemostatic device 10 to perform the first distal end operation and the second distal end operation. Thus, the user can easily operate the hemostatic device 10 and perform the first distal end operation and the second distal end operation.

The second tubular member 8D is connected to the coupling section 71C that is provided on the distal end section of the housing 71. The positioning member 8A, the push-out member 8B, and the first tubular member 8C are respectively inserted through the interior of the second tubular member 8D. When the second distal end operation has been performed, the opening 6A of the blood vessel 6 is closed by the hemostatic agent S. At the same time, the coupling section 71C is in the state of being able to move relatively to the proximal end side with respect to the housing 71, the positioning member 8A, the push-out member 8B, and the first tubular member 8C. In this case, the hemostatic device 10 can cause the second tubular member 8D to move to the proximal end side as a result of the coupling proximal end operation being subsequently performed. Note that, by the coupling proximal end operation, the hemostatic agent S is disengaged from the second distal end 86 of the second tubular member 8D. Thus, the hemostatic device 10 can remove the second tubular member 8D from the puncture hole 61 in a state in which the hemostatic agent S has been caused to be disengaged from the second distal end 86 of the second tubular member 8D.

When the limiting section 747 of the restricting mechanism 74C is disposed in the second movement region of the coupling section 71C, the limiting section 747 restricts the movement of the coupling section 71C. When the limiting section 747 of the restricting mechanism 74C is not disposed in the second movement region of the coupling section 71C, the limiting section 747 enables the movement of the coupling section 71C. In accordance with the push-out member 8B having moved to the distal end side in the second distal end operation, the restricting mechanism 74C switches the limiting section 747 from the state of being disposed in the second movement region to the state of not being disposed in the second movement region. In this way, the coupling section 71C is switched from the state of not being able to move to the proximal end side to the state of being able to move to the proximal end side. As a result, the hemostatic device 10 can release the restriction on the movement of the coupling section 71C in concert with the second distal end operation to move the push-out member 8B.

The hemostatic device 10 causes the positioning member 8A to move relatively to the proximal end side with respect to the first tubular member 8C, the second tubular member 8D, and the push-out member 8B, in the positioning distal end operation that is performed in accordance with the operation of the third operation unit 530. In this way, after closing the opening 6A of the blood vessel 6 using the hemostatic agent S, the hemostatic device 10 causes the first engagement section 82 of the positioning member 8A to move further to the proximal end side than the hemostatic agent S. The hemostatic device 10 can cause the positioning member 8A to move to the proximal end side independently from the first tubular member 8C, the second tubular member 8D, and the push-out member 8B. Thus, the hemostatic device 10 can easily enable the first engagement section 82 to be removed from the blood vessel 6.

When the first distal end operation and the second distal end operation are performed, the first operation unit 510 is moved to the proximal end side. Thus, when performing the second distal end operation, the user can move the first operation unit 510 to the proximal end side and push out the hemostatic agent S into the opening 6A, while pulling the housing 71 to the proximal end side in order to cause the first engagement section 82 of the positioning member 8A to adhere closely to the opening 6A of the blood vessel 6. In other words, the hemostatic device 10 can cause the direction of a force acting on the housing 71 in order to cause the positioning member 8A to adhere closely to the blood vessel 6 to be the same as an operation direction of the first operation unit 510. Thus, the hemostatic device 10 can cause an operation by the user when performing of the first distal end operation and the second distal end operation to be easier.

The first engagement section 82 of the positioning member 8A is the balloon that can be switched between the inflated state and the contracted state. The balloon engages with the opening 6A in the inflated state. In this case, the hemostatic device 10 can introduce the balloon in the inflated state into the blood vessel 6, via the opening 6A. By causing the balloon introduced into the blood vessel 6 to be in the inflated state, the hemostatic device 10 can cause the balloon to engage with the opening 6A from the inside of the blood vessel 6.

Second Embodiment

The hemostatic device 20 according to an embodiment of the present disclosure will be explained with reference to the drawings. A description of a configuration that is the same as that of the first embodiment (the positioning member 8A, the push-out member 8B) will be omitted or simplified.

Housing 1

Figure 23:
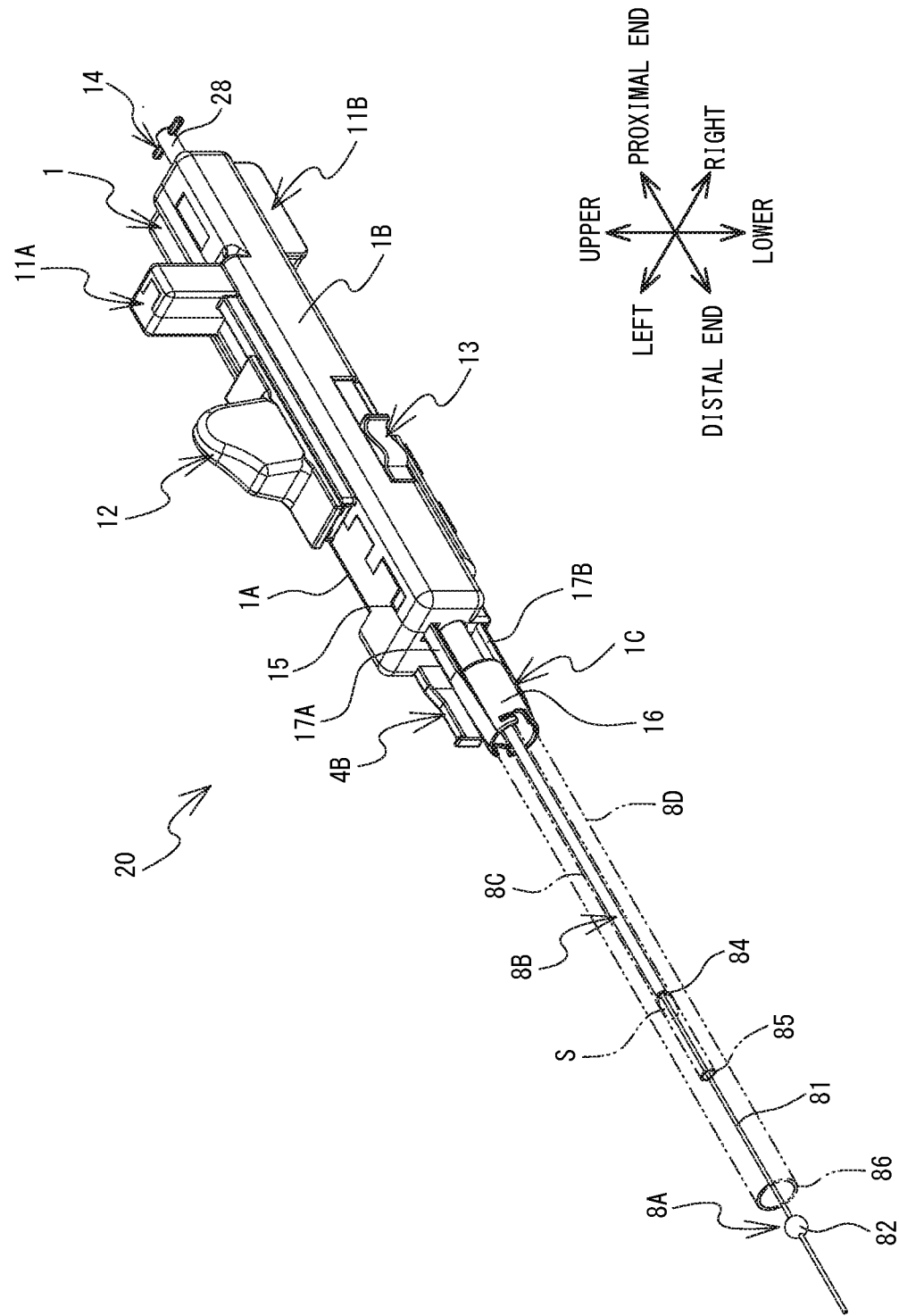
FIG. 23 is a perspective view of a hemostatic device 20.
Figure 24:
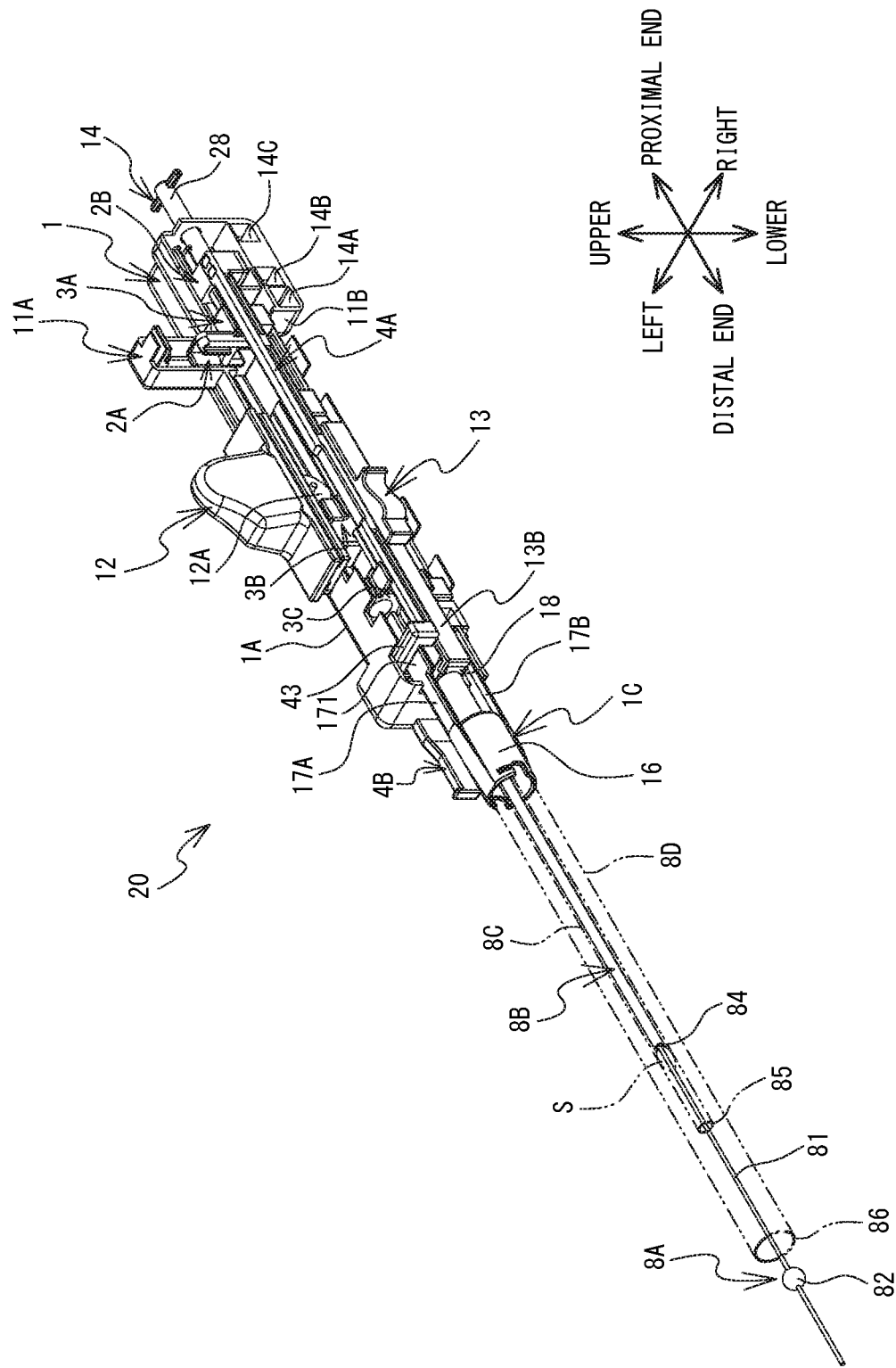
FIG. 24 is a perspective view showing an internal structure of the hemostatic device 20.

As shown in FIG. 23, a housing 1 has a substantially cuboid shape that is long in the extending direction. The housing 1 is formed by combining a left housing 1A corresponding to a part that is the left side half of the housing 1, and a right housing 1B corresponding to a part that is the right side half of the housing 1. The housing 1 includes a protruding section 11A that protrudes upward from the upper side in the vicinity of the proximal end section of the housing 1. As shown in FIG. 24, at least a part of each of the positioning member 8A, the push-out member 8B, the first tubular member 8C, a restricting member 2A, a switching member 2B, a first moving member 3A, a second moving member 4A, a fourth moving member 3B, a fifth moving member 3C, a sixth moving member 4B, and a restricting mechanism 4C (refer to FIG. 34 and FIG. 35), all of which are to be described later, is housed inside the housing 1.

As shown in FIG. 23, on the upper surface of the housing 1, a first operation unit 12 is provided on the distal end side of the protruding section 11A. The first operation unit 12 is a slide lever that is operated by the user, using a finger. The first operation unit 12 can move in the extending direction in accordance with the operation by the user. The first operation unit 12 causes the first moving member 3A (refer to FIG. 28), the fourth moving member 3B (refer to FIG. 30), the fifth moving member 3C (refer to FIG. 31), and the sixth moving member 4B (refer to FIG. 33), to be described later, to move in the extending direction. Further, the first operation unit 12 causes the push-out member 8B that is connected to the first moving member 3A, and the first tubular member 8C that is connected to the fourth moving member 3B, to move in the extending direction.

On the right surface of the housing 1, a third operation unit 13 is provided in substantially the same position as the first operation unit 12 in the extending direction. The third operation unit 13 is a slide lever that is operated by the user, using a finger. The third operation unit 13 can move in the extending direction in accordance with the operation by the user. The third operation unit 13 causes a coupling section 1C to be described later (refer to FIG. 32), and the second tubular member 8D that is connected to the coupling section 1C to move in the extending direction.

A second operation unit 14 is provided on the proximal end side of the housing 1. The second operation unit 14 is a handle that is grasped and operated by the user. The second operation unit 14 can move in the extending direction in accordance with the operation by the user. The second operation unit 14 causes the switching member 2B to be described later (refer to FIG. 26), and the positioning member 8A that is connected to the switching member 2B to move in the extending direction.

A notification section 15 is provided on the upper surface of the housing 1, further to the front than the first operation unit 12. The notification section 15 is an opening provided in the upper surface of the housing 1. The user can visually observe the interior of the housing 1 via the notification section 15.

Figure 25:
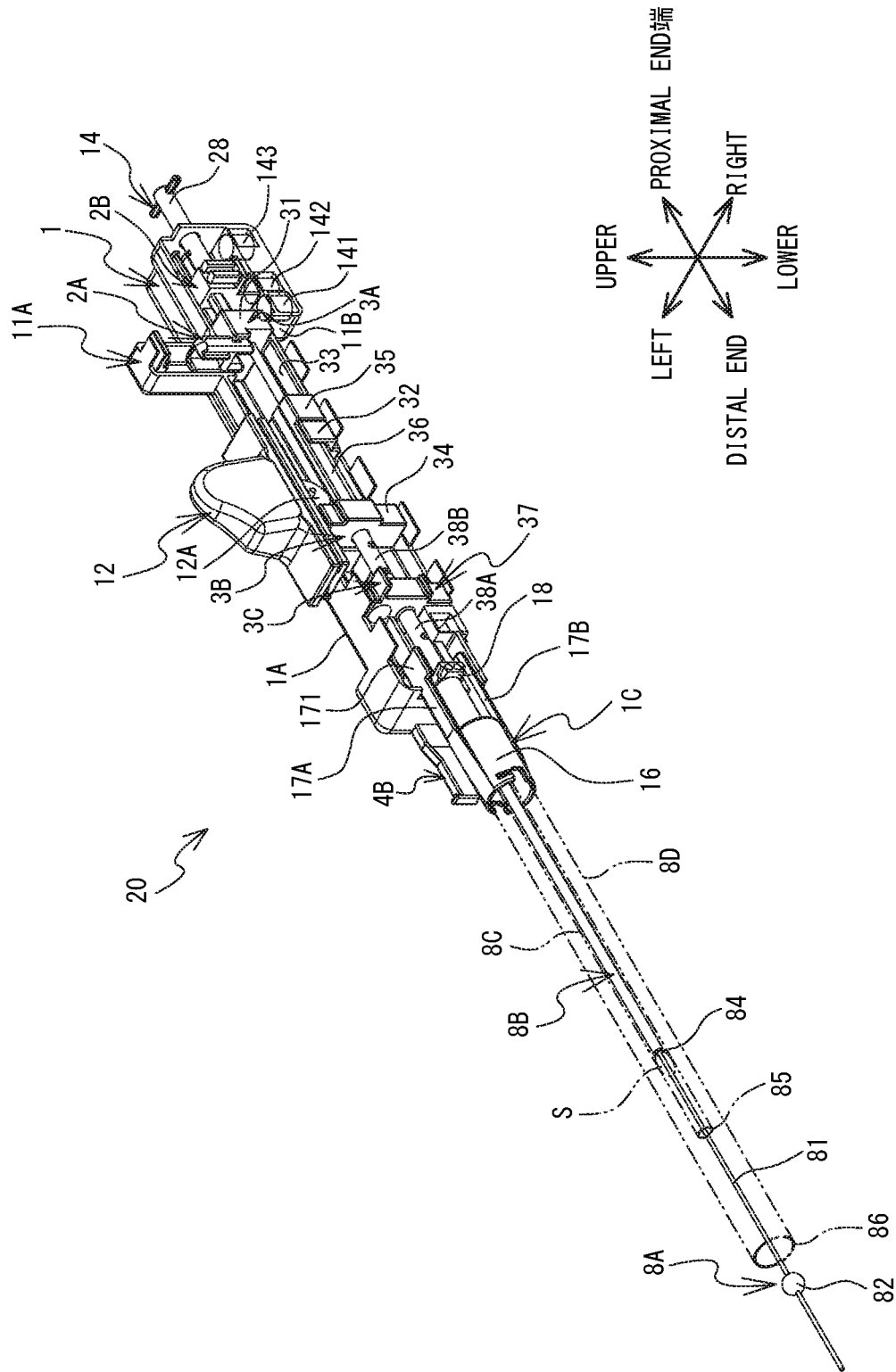
FIG. 25 is a perspective view showing the internal structure of the hemostatic device 20.

A protruding section 11B that protrudes downward is provided on the lower surface in the vicinity of the proximal end section of the housing 1. As shown in FIG. 24, housing sections 14A to 14C are formed in the interior of the protruding section 11B. Each of the housing sections 14A to 14C is a substantially cuboid space. The housing sections 14A to 14C are aligned in order along the extending direction. The housing section 14A and the housing section 14B are adjacent to each other in the extending direction, and the housing section 14B and the housing section 14C are separated from each other in the extending direction. Further, thicknesses of each of the housing sections 14A to 14C, and wall sections dividing up the interior space of the housing 1 (hereinafter referred to as "partition walls") are respectively different from each other. Specifically, the thickness of the partition wall on the upper side of the housing section 14A is greater than the thickness of the partition walls on the upper side of each of the housing sections 14B and 14C. As shown in FIG. 25, a magnet 141 is housed in the housing section 14A. A magnet 142 is housed in the housing section 14B. A magnet 143 is housed in the housing section 14C. Using magnetic force, the magnets 141 to 143 limit the movement, in the extending direction, of the switching member 2B to be described later (refer to FIG. 26). Note that the magnets 141 to 143 are not illustrated in FIG. 24.

Positioning Member 8A, Push-Out Member 8B, First Tubular Member 8C, and Second Tubular Member 8D

As shown in FIG. 23 to FIG. 25, the proximal end section of the extending section 81 of the positioning member 8A is connected to the switching member 2B to be described later (refer to FIG. 26). The extending section 81 extends from the switching member 2B through the interior of the housing 1 toward the distal end side, and protrudes to the distal end side from the distal end section of the housing 1. The proximal end section of the push-out member 8B is connected to the first moving member 3A to be described later (refer to FIG. 28). The push-out member 8B extends from the first moving member 3A through the interior of the housing 1 toward the distal end side, and protrudes to the distal end side from the distal end section of the housing 1. The extending section 81 of the positioning member 8A is inserted through the lumen of the push-out member 8B. The proximal end section of the first tubular member 8C is connected to the fourth moving member 3B to be described later (refer to FIG. 30). The first tubular member 8C extends from the fourth moving member 3B through the interior of the housing 1 toward the distal end side, and protrudes to the distal end side from the distal end section of the housing 1. The extending section 81 of the positioning member 8A and the push-out member 8B are inserted through the lumen of the first tubular member 8C. The proximal end section of the second tubular member 8D is connected to the coupling section 1C to be described later (refer to FIG. 32). The extending section 81 of the positioning member 8A, the push-out member 8B, and the first tubular member 8C are inserted through the lumen of the second tubular member 8D.

Switching Member 2B

As shown in FIG. 25, the switching member 2B is disposed above the protruding section 11B in the interior of the housing 1. The switching member 2B switches a state of the restricting member 2A to be described later (refer to FIG. 29). The switching member 2B moves in the extending direction in accordance with operation of the second operation unit 14, and causes the positioning member 8A to move in the extending direction. As shown in FIG. 26, the switching member 2B includes a base section 25, protruding sections 26A and 26B, a connection section 27, and a cylindrical section 28.

The base section 25 is a substantially cuboid shape. The base section 25 includes a through hole (not shown in the drawings) that penetrates in the extending direction between a surface of the base section 25 on the distal end side and a surface of the base section 25 on the proximal end side. The proximal end section of the extending section 81 of the positioning member 8A is connected to the surface of the base section 25 on the distal end side. The lumen of the extending section 81 is communicated with the through hole of the base section 25. A magnet 25A is built into the lower end section of the base section 25. In accordance with the movement in the extending direction of the switching member 2B, the magnet 25A faces, from above, one of the magnets 141 to 143 (refer to FIG. 25) of the housing 1. Hereinafter, the position of the switching member 2B when the magnet 25A of the base section 25 is in a state of being above and facing the magnet 141 of the housing 1 is referred to as a "first switching position." The position of the switching member 2B when the magnet 25A of the base section 25 is in a state of being above and facing the magnet 142 of the housing 1 is referred to as a "second switching position." The position of the switching member 2B when the magnet 25A of the base section 25 is in a state of being above and facing the magnet 143 of the housing 1 is referred to as a "third switching position." The position of the switching member 2B when the magnet 25A of the base section 25 is in a state of being above and facing a separation section between the magnets 142 and 143 of the housing 1 is referred to as an "initial switching position." In an initial state in which the hemostatic device 20 is not being used, the switching member 2B is disposed in the initial switching position (refer to FIG. 36 and FIG. 37).

Note that, as described with reference to FIG. 24 and FIG. 25, the thickness of the partition wall above the housing sections 14B and 14C of the housing 1 that house the magnets 142 and 143 is less than the thickness of the partition wall above the housing section 14A that houses the magnet 141. Thus, when the switching member 2B is disposed in the second switching position or in the third switching position, the magnetic force acting between the magnet 25A of the switching member 2B and the magnets 142 and 143 of the housing 1 is relatively large. On the other hand, when the switching member 2B is disposed in the first switching position, the magnetic force acting between the magnet 25A of the switching member 2B and the magnet 141 of the housing 1 is relatively small.

Figure 26:
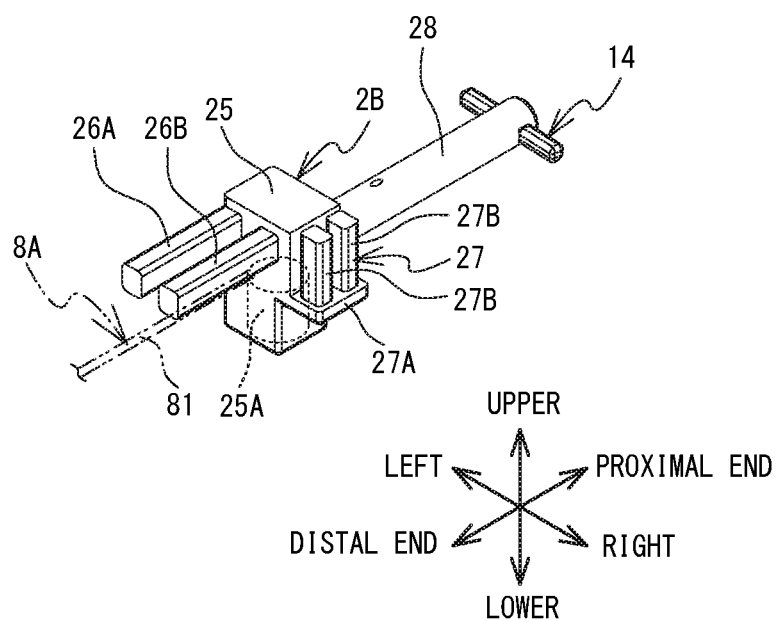
FIG. 26 is a perspective view of a switching member 2B.

As shown in FIG. 26, each of the protruding sections 26A and 26B has a bar shape and protrudes to the distal end side from the surface of the base section 25 on the distal end side. The protruding sections 26A and 26B are aligned in the left-right direction. The protruding section 26A is disposed on the left side of the protruding section 26B. As shown in FIG. 25, the protruding sections 26A and 26B are inserted, from the proximal end side, through second engagement sections 311 and 312 (refer to FIG. 28) of the first moving member 3A to be described later.

As shown in FIG. 26, the connection section 27 includes a plate-shaped first extension section 27A that extends to the right from the right surface of the base section 25, and two bar-shaped second extension sections 27B that extend upward from the first extension section 27A. The two second extension sections 27B are aligned in the extending direction. As shown in FIG. 24, the second moving member 4A to be described later is connected to the connection section 27. As shown in FIG. 26, the cylindrical section 28 has a cylindrical shape, and protrudes to the proximal end side from the surface of the base section 25 on the proximal end side. The lumen of the cylindrical section 28 is communicated with the through hole (not shown in the drawings) of the base section 25. The second operation unit 14 is connected to the proximal end section of the cylindrical section 28.

As shown in FIG. 23 to FIG. 25, the cylindrical section 28 protrudes to the proximal end side from the proximal end section of the housing 1. A hub (not shown in the drawings) is connected to the proximal end section of the cylindrical section 28, via a tube (not shown in the drawings). The hub injects the compressed fluid into the lumen of the extending section 81 of the positioning member 8A, via the lumen of the cylindrical section 28, and the through hole (not shown in the drawings) of the base section 25. By inflating the first engagement section 82 of the positioning member 8A, the compressed fluid injected into the extending section 81 switches the first engagement section 82 from the contracted state to the inflated state.

Second Moving Member 4A

Figure 27:
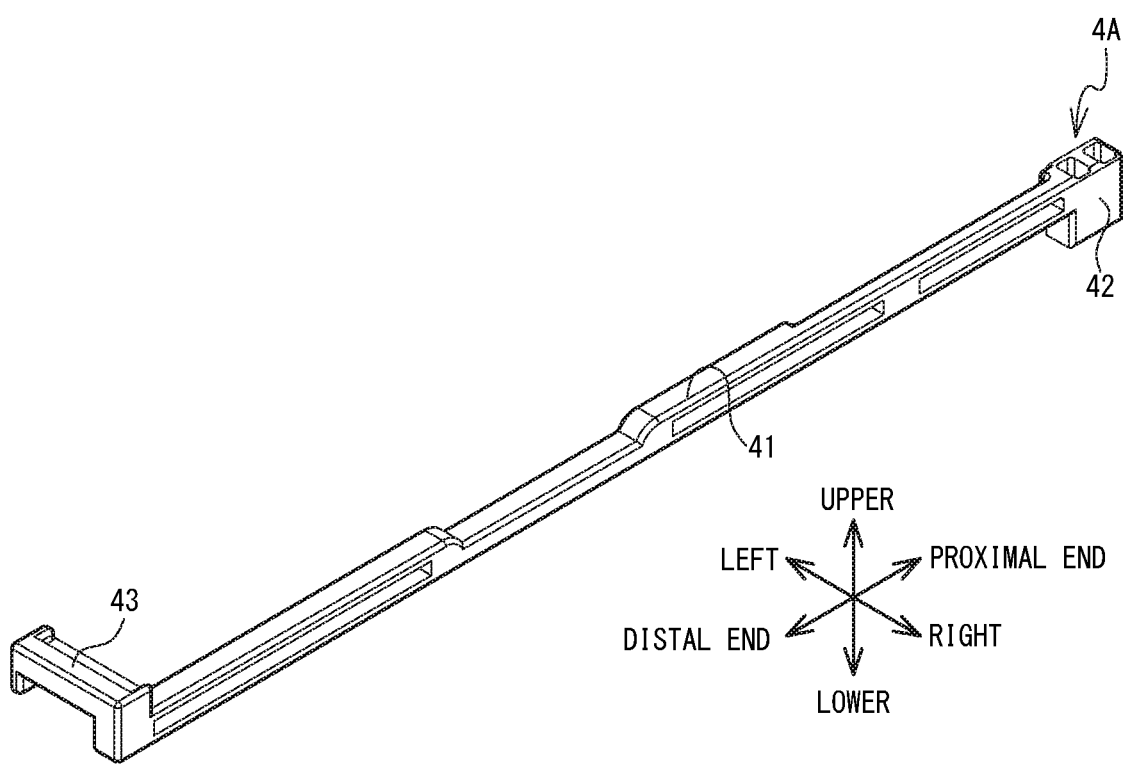
FIG. 27 is a perspective view of a second moving member 4A.

As shown in FIG. 24, the second moving member 4A is connected to the connection section 27 (refer to FIG. 26) of the switching member 2B. The second moving member 4A notifies the user, via the notification portion 15 (refer to FIG. 23) of the housing 1, of a relative position of the switching member 2B with respect to the housing 1. As shown in FIG. 27, the second moving member 4A includes a bar section 41, a connection section 42, and an exposed section 43.

The bar section 41 is substantially bar shaped, and extends along the extending direction. The connection section 42 is provided on the proximal end section of the bar section 41, and includes two through holes that penetrate in the up-down direction. The two second extension sections 27B (refer to FIG. 26) of the connection section 27 of the switching member 2B are inserted, from below, through the two through holes of the connection section 42. In this way, the proximal end section of the second moving member 4A is connected to the switching member 2B. In a state in which the second moving member 4A is connected to the switching member 2B, the bar section 41 extends to the proximal end side from the switching member 2B. The second moving member 4A can move in the extending direction along with the movement of the switching member 2B.

The exposed section 43 is connected to the proximal end section of the bar section 41, and extends to the left. When the switching member 2B is disposed in the initial switching position or in the third switching position, the exposed section 43 is disposed further to the proximal end side than the notification section 15 of the housing 1. In this case, the user cannot visually observe the exposed section 43 via the notification section 15. When the switching member 2B is disposed in the second switching position, the exposed section 43 is disposed below the notification section 15 of the housing 1. In this case, the user can visually observe the exposed section 43 via the notification section 15. When the switching member 2B is disposed in the first switching position, the exposed section 43 is disposed further to the distal end side than the notification section 15 of the housing 1. In this case, the user cannot visually observe the exposed section 43 via the notification section 15. In this way, in accordance with the relative position of the second moving member 4A with respect to the housing 1, the hemostatic device 20 switches between a state in which the exposed section 43 can be visually observed and a state in which the exposed section 43 cannot be visually observed via the notification section 15.

First Moving Member 3A

As shown in FIG. 25, the first moving member 3A is disposed to the distal end side of the switching member 2B inside the housing 1. The first moving member 3A moves in the extending direction in accordance with the operation of the first operation unit 12. Hereinafter, the position of the first moving member 3A that has moved furthest to the proximal end side is referred to as the "first proximal end position" (refer to FIG. 36 to FIG. 39, to be described later), and the position of the first moving member 3A that has moved furthest to the distal end side is referred to as the "first distal end position" (refer to FIG. 44 to FIG. 47, to be described later). An intermediate position between the first proximal end position and the first distal end position is referred to as the "first intermediate position" (refer to FIG. 40 to FIG. 43, to be described later). In the initial state in which the hemostatic device 20 is not being used, the first moving member 3A is disposed in the first proximal end position (refer to FIG. 36 and FIG. 37). A region through which the first moving member 3A passes when moving in the extending direction is referred to as the "first movement region." As shown in FIG. 28, the first moving member 3A includes a first base section 31, a second base section 32, and a bridge section 33.

The first base section 31 is substantially cuboid. The first base section 31 includes a through hole 313 and the second engagement sections 311 and 312, which are through holes penetrating in the extending direction between the surface on the distal end side of the first base section 31 and the surface on the proximal end side of the first base section 31. The second engagement sections 311 and 312 are provided on the upper end section of the first base section 31 and are aligned in the left-right direction. The second engagement section 311 is disposed to the left of the second engagement section 312. As shown in FIG. 25, when the first moving member 3A is disposed in the first proximal end position, the protruding section 26A (refer to FIG. 26) of the switching member 2B disposed in the initial switching position is inserted, from the proximal end side, through the second engagement section 311, and the protruding section 26B (refer to FIG. 26) of the switching member 2B is inserted, from the proximal end side, through the second engagement section 312. Further, limiting sections 23A and 23B (refer to FIG. 29) of the restricting member 2A to be described later can be inserted through and engage with the second engagement sections 311 and 312 from the distal end side.

Figure 28:
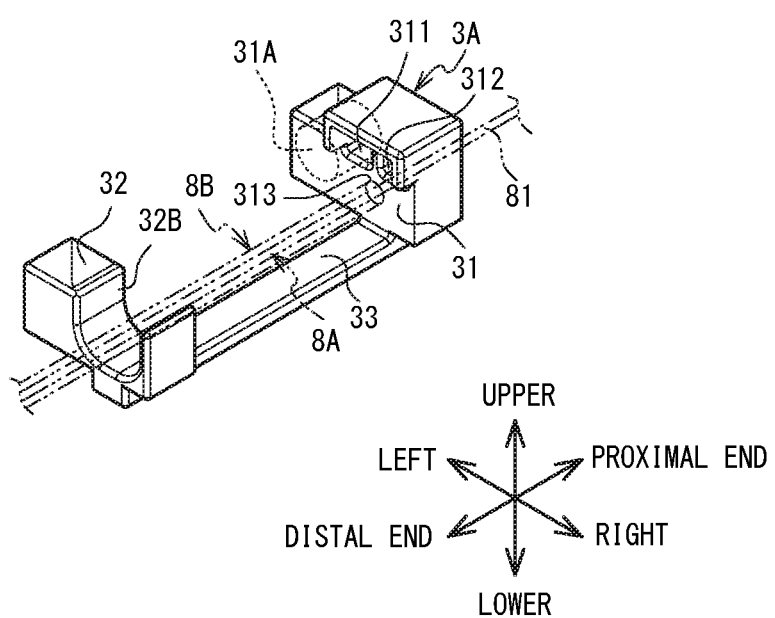
FIG. 28 is a perspective view of a first moving member 3A.

As shown in FIG. 28, the through hole 313 is provided below the second engagement sections 311 and 312 of the first base section 31. The extending section 81 of the positioning member 8A extending to the distal end side from the switching member 2B (refer to FIG. 26) passes through the through hole 313 from the proximal end side. The proximal end section of the push-out member 8B is connected to the surface on the distal end side of the first base section 31. The lumen of the push-out member 8B is communicated with the through hole 313. The extending section 81 of the positioning member 8A extends to the distal end side from the through hole 313 and passes through the lumen of the push-out member 8B. A magnet 31A is built into the left end section of the first base section 31.

The second base section 32 is disposed so as to be separated, to the distal end side, from the first base section 31. The second base section 32 is substantially cuboid and includes a recessed section 32B that is recessed downward. The extending section 81 of the positioning member 8A, and the push-out member 8B pass through the inside of the recessed section 32B. The bridge section 33 has a plate shape, and extends in the extending direction. The proximal end section of the bridge section 33 is connected to the lower end section of the first base section 31. The distal end section of the bridge section 33 is connected to the lower end section of the second base section 32.

Restricting Member 2A

Figure 29:
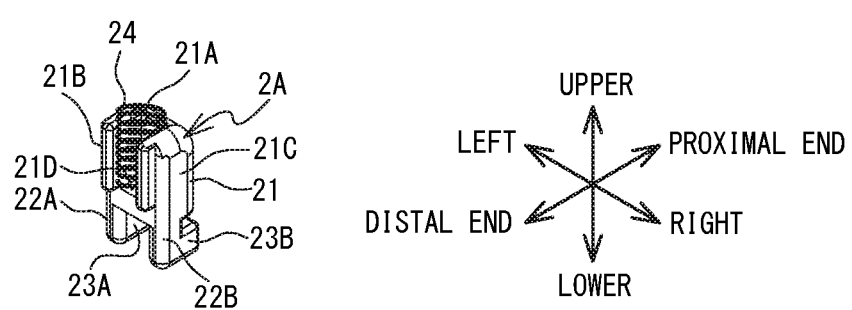
FIG. 29 is a perspective view of a restricting member 2A.

As shown in FIG. 25, the restricting member 2A is disposed inside the protruding section 11A of the housing 1. The restricting member 2A moves in the up-down direction inside the protruding section 11A, in accordance with an urging force of an urging section 24 (refer to FIG. 29) to be described later. As shown in FIG. 29, the restricting member 2A includes a base section 21, extension sections 22A and 22B, the limiting sections 23A and 23B, and the urging section 24.

The base section 21 includes a first portion 21A, second portions 21B and 21C, and a third portion 21D. On the proximal end side, the first portion 21A has a surface orthogonal to the extending direction. The second portion 21B extends to the distal end side from the right end section of the first portion 21A, and has a surface, on the left side thereof, orthogonal to the left-right direction. The second portion 21C extends to the distal end side from the left end section of the first portion 21A and has a surface, on the right side thereof, orthogonal to the left-right direction. The third portion 21D extends to the distal end side from the lower end section of the first portion 21A, and has a surface, on the upper side thereof, orthogonal to the up-down direction. The urging section 24 is disposed in a recessed section surrounding by the respective surfaces of the first portion 21A, the second portions 21B and 21C, and the third portion 21D. The urging section 24 is a tension coil spring. The upper end section of the urging section 24 is connected to an inner wall of the upper side of the protruding section 11A (refer to FIG. 23 to FIG. 25) of the housing 1. The lower end section of the urging section 24 is connected to the upper surface of the third portion 21D of the base section 21 of the restricting member 2A. The urging force in the upward direction, which results from the elastic force of the urging section 24, acts on the restricting member 2A.

The extension section 22A extends downward from the left end section of the third portion 21D of the base section 21. The limiting section 23A protrudes to the proximal end side from the lower end section of the extension section 22A. The extension section 22B extends downward from the right end section of the third portion 21D of the base section 21. The limiting section 23B protrudes to the proximal end side from the lower end section of the extension section 22B.

In a state in which the base section 21 has moved downward in resistance to the urging force of the urging section 24 (refer to FIG. 25), the limiting sections 23A and 23B are disposed in the first movement region of the first moving member 3A. In this state, from the distal end side, the limiting sections 23A and 23B are inserted through and engage with the second engagement sections 311 and 312 (refer to FIG. 28) of the first moving member 3A disposed in the first proximal end position. When the limiting sections 23A and 23B are engaged with the first moving member 3A, the upward movement of the restricting member 2A due to the urging force of the urging section 24 is limited. Further, in this state, the movement of the first moving member 3A from the first proximal end position toward the first distal end position is restricted by the limiting sections 23A and 23B. Thus, the movement of the push-out member 8B connected to the first moving member 3A is also restricted. Hereinafter, a state in which the limiting sections 23A and 23B are engaged with the second engagement sections 311 and 312 of the first moving member 3A and restrict the movement of the first moving member 3A is referred to as the "restricting state."

When the restricting member 2A is in the restricting state, when the switching member 2B (refer to FIG. 26) has moved from the initial switching position toward the distal end side, the protruding sections 26A and 26B (refer to FIG. 26) of the switching member 2B protrude to the distal end side from the second engagement sections 311 and 312 (refer to FIG. 28) of the first moving member 3A. In this way, the state of engagement of the second engagement sections 311 and 312 of the first moving member 3A with respect to the limiting sections 23A and 23B is released. In this case, the base section 21 moves upward in accordance with the urging force of the urging section 24. In this way, the limiting sections 23A and 23B of the restricting member 2A are no longer disposed in the first movement region of the first moving member 3A. In this state, the movement of the first moving member 3A is not restricted by the limiting sections 23A and 23B, and the first moving member 3A can move in the extending direction through the first movement region. Hereinafter, the state in which the limiting sections 23A and 23B are not engaged with the second engagement sections 311 and 312 of the first moving member 3A, and the movement of the first moving member 3A is not restricted is referred to as the "enabling state."

Fourth Moving Member 3B

Figure 30:
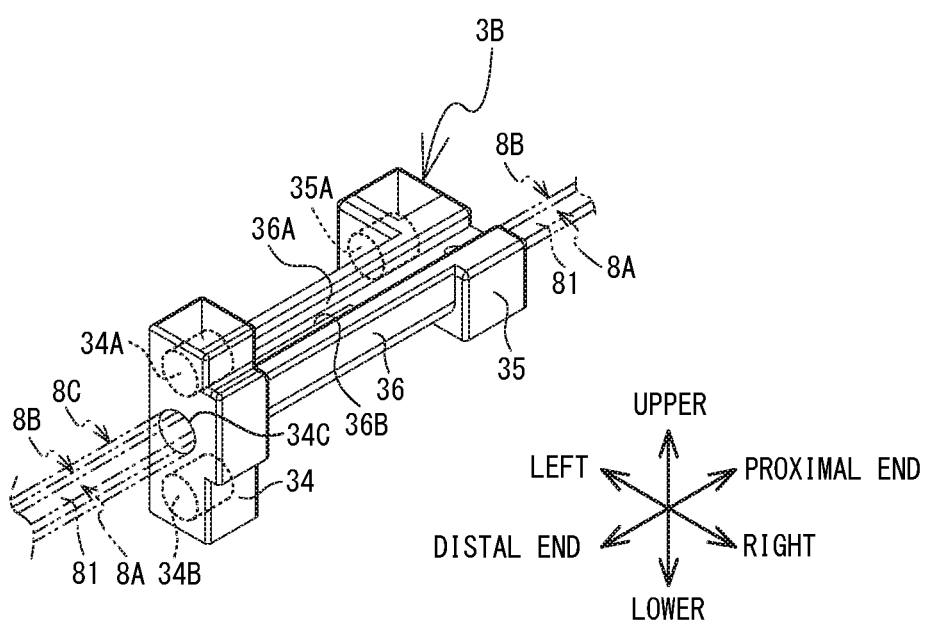
FIG. 30 is a perspective view of a fourth moving member 3B.

As shown in FIG. 25, in the interior of the housing 1, the fourth moving member 3B is disposed to the distal end side of the first moving member 3A and below the first operation unit 12. The fourth moving member 3B moves in the extending direction in accordance with the operation of the first operation unit 12, and causes the first tubular member 8C to move in the extending direction. Hereinafter, a position of the fourth moving member 3B that has moved furthest to the proximal end side is referred to as the "fourth proximal end position" (refer to FIG. 36 to FIG. 39, FIG. 42, and FIG. 43), and a position of the fourth moving member 3B that has moved furthest to the distal end side is referred to as the "fourth distal end position" (refer to FIG. 40, FIG. 41, and FIG. 44 to FIG. 47). In the initial state in which the hemostatic device 20 is not being used, the fourth moving member 3B is disposed in the fourth proximal end position (refer to FIG. 36 and FIG. 37). As shown in FIG. 30, the fourth moving member 3B includes a first base section 34, a second base section 35, and a bridge section 36.

The first base section 34 is a substantially cuboid shape that is long in the up-down direction. A magnet 34A is built into the upper end section of the first base section 34, and a magnet 34B is built into the lower end section of the first base section 34. The second base section 35 is disposed to the proximal end side of the first base section 34 so as to be separated from the first base section 34. The second base section 35 is a substantially cuboid shape that is long in the left-right direction. A magnet 35A is built into the left end section of the second base section 35. The bridge section 36 extends in the extending direction, and couples the first base section 34 and the second base section 35. The distal end section of the bridge section 36 is connected to the center, in the up-down direction, of the surface on the proximal end side of the first base section 34. The proximal end section of the bridge section 36 is connected to the right side of the surface on the distal end side of the second base section 35.

A through hole 34C that extends in the extending direction is formed through the first base section 34, the bridge section 36, and the second base section 35. The proximal end section of the first tubular member 8C is connected to the surface on the proximal end side of the second base section 35. The first tubular member 8C passes through the through hole 34C from the proximal end section to the distal end section thereof, and extends further to the distal end side than the first base section 34. The extending section 81 of the positioning member 8A that extends to the proximal end side from the switching member 2B (refer to FIG. 26), and the push-out member 8B that extends to the proximal end side from the first moving member 3A (refer to FIG. 28) are inserted through the through hole 34C, from the proximal end side. The extending section 81 of the positioning member 8A, and the push-out member 8B pass through the lumen of the first tubular member 8C, and extend further to the proximal end side than the first base section 34. A tubular section 38B (refer to FIG. 31) of the fifth moving member 3C to be described later, is inserted through the through hole 34C, from the proximal end side.

A groove section 36A that extends in the extending direction is provided in the upper surface of the bridge section 36. A rack gear 36B is formed in the bottom surface of the groove section 36A. As shown in FIG. 25, a pinion gear 12A provided inside the housing 1 and below the first operation unit 12 meshes with the rack gear 36B. The pinion gear 12A rotates in accordance with the operation of the first operation unit 12. The fourth moving member 3B moves in the extending direction in accordance with the rotation of the pinion gear 12A. More specifically, when an operation is performed to move the first operation unit 12 to the distal end side, the fourth moving member 3B moves to the proximal end side. When an operation is performed to move the first operation unit 12 to the proximal end side, the fourth moving member 3B moves to the distal end side.

As shown in FIG. 25, the second base section 35 of the fourth moving member 3B is disposed further to the proximal end side than the second base section 32 of the first moving member 3A. The bridge section 36 of the fourth moving member 3B fits, from above, into the recessed section 32B (refer to FIG. 28) provided in the second base section 32 of the first moving member 3A.

Fifth Moving Member 3C

Figure 31:
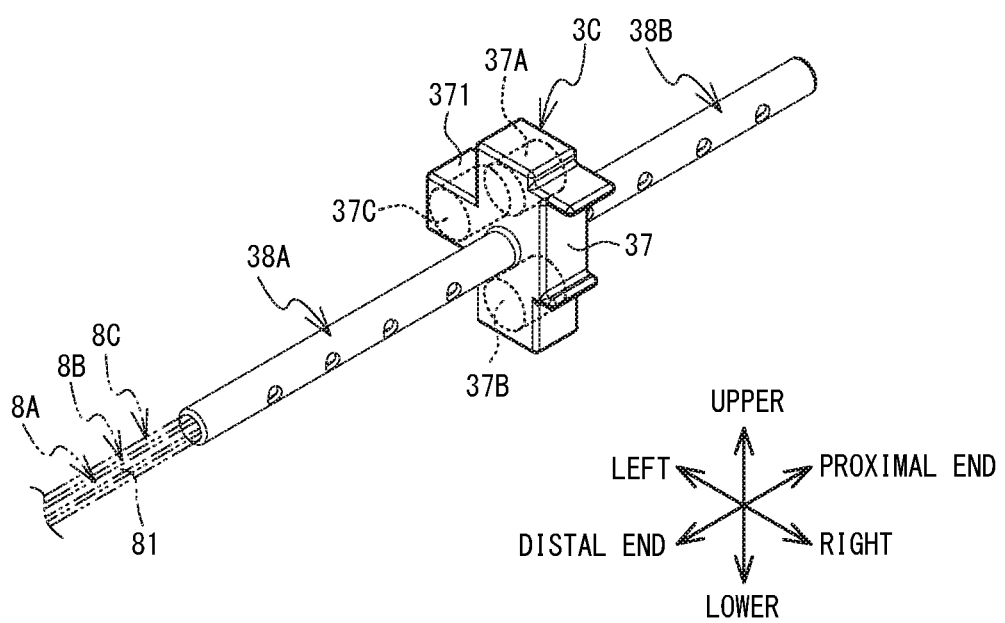
FIG. 31 is a perspective view of a fifth moving member 3C.

As shown in FIG. 25, in the interior of the housing 1, the fifth moving member 3C is disposed to the distal end side of the fourth moving member 3B. The fifth moving member 3C moves in the extending direction in accordance with the operation of the first operation unit 12. Hereinafter, a position of the fifth moving member 3C that has moved furthest to the proximal end side is referred to as the "fifth proximal end position" (refer to FIG. 42 and FIG. 43), and a position of the fifth moving member 3C that has moved furthest to the distal end side is referred to as the "fifth distal end position" (refer to FIG. 36 to FIG. 41, and FIG. 44 to FIG. 47). In the initial state in which the hemostatic device 20 is not being used, the fifth moving member 3C is disposed in the fifth distal end position (refer to FIG. 36 and FIG. 37). As shown in FIG. 31, the fifth moving member 3C includes a base section 37, and tubular sections 38A and 38B.

The base section 37 is a substantially cuboid shape that is long in the up-down direction. The base section 37 includes a protruding section 371 that protrudes to the left from the center, in the up-down direction, of the base section 37. A magnet 37A is built into the upper end section of the base section 37, and a magnet 37B is built into the lower end section of the base section 37. A magnet 37C is built into the protruding section 371 of the base section 37. The base section 37 includes a through hole (not shown in the drawings) that extends in the extending direction, in the center of the base section 37 in the up-down direction. The tubular section 38A extends to the distal end side from a portion in which the through hole is formed, of the surface of the base section 37 on the distal end side. The tubular section 38B extends to the proximal end side from a portion in which the through hole is formed, of the surface of the base section 37 on the proximal end side. A lumen of each of the tubular sections 38A and 38B is communicated with the through hole of the base section 37.

As shown in FIG. 25, the tubular section 38B is inserted, from the distal end side, through the through hole 34C (refer to FIG. 30) of the fourth moving member 3B. As shown in FIG. 31, the extending section 81 of the positioning member 8A extending to the distal end side from the switching member 2B (refer to FIG. 26), the push-out member 8B extending to the distal end side from the first moving member 3A (refer to FIG. 29), and the first tubular member 8C extending to the distal end side from the fourth moving member 3B (refer to FIG. 30) are inserted through the tubular section 38B from the proximal end side. The extending section 81 of the positioning member 8A, the push-out member 8B, and the first tubular member 8C pass through the lumens of the tubular sections 38A and 38B, and extend to the distal end side from the distal end section of the tubular section 38A.

Coupling Section 1C

Figure 32:
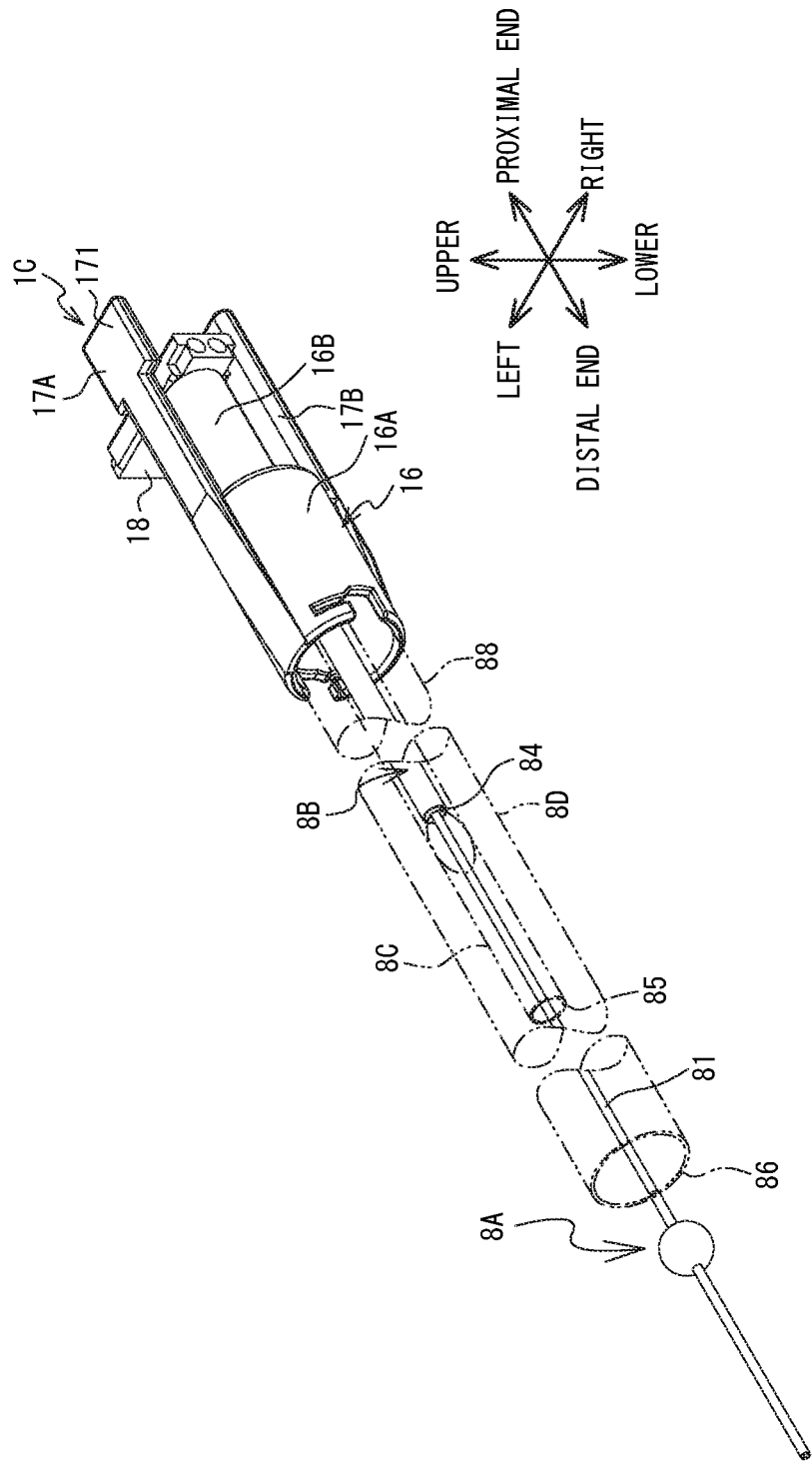
FIG. 32 is a perspective view of a coupling section 1C.

As shown in FIG. 5, the coupling section 1C is provided on the distal end section of the housing 1. The coupling section 1C moves in accordance with the operation of the third operation unit 13 (refer to FIG. 23), and causes the second tubular member 8D to move in the extending direction. Hereinafter, a position of the coupling section 1C that has moved furthest to the proximal end side is referred to as a "coupling proximal end position" (refer to FIG. 35, FIG. 46, and FIG. 47), and a position of the coupling section 1C that has moved furthest to the distal end side is referred to as a "coupling distal end position" (refer to FIG. 34, and FIG. 36 to FIG. 45). The movement of the coupling section 1C can be restricted by the restricting mechanism 4C (refer to FIG. 34 and FIG. 35) to be described later. As shown in FIG. 32, the coupling section 1C includes a tubular section 16, extension sections 17A and 17B, and a protruding section 18.

The tubular section 16 is a tubular member that includes a lumen extending in the extending direction. The tubular section 16 includes a distal end tubular section 16A and a proximal end tubular section 16B that are aligned in the extending direction. The distal end tubular section 16A is disposed to the distal end side of the proximal end tubular section 16B. The diameter of the distal end tubular section 16A is larger than the diameter of the proximal end tubular section 16B. The second tubular member 8D is removably connected to the proximal end section of the distal end tubular section 16A, via the connector 88. The extending section 81 of the positioning member 8A, the push-out member 8B, and the first tubular member 8C pass through the lumen of the second tubular member 8D and extend to the distal end side.

The extension sections 17A and 17B have a long thin plate shape. The extension section 17A extends to the proximal end side from the upper end section of the distal end tubular section 16A. A widened section 171 is connected to the proximal end section of the extension section 17A. The width, in the left-right direction, of the widened section 171 is greater than that of the extension section 17A. The extension section 17B extends to the proximal end side from the lower end section of the proximal end tubular section 16B. The protruding section 18 protrudes to the left from the proximal end section of the proximal end tubular section 16B.

As shown in FIG. 25, the proximal end sections of each of the proximal end tubular section 16B and the extension sections 17A and 17B are inserted, from the distal end side, through a through hole provided in the distal end section of the housing 1. When the coupling section 1C has moved to the distal end side, the widened section 171 is caught on the inner wall of the housing 1. In this way, the coupling section 1C is inhibited from becoming disengaged from the housing 1.

As shown in FIG. 24, a plate-shaped bridge section 13B is connected to the right end section of the protruding section 18. The bridge section 13B extends to the proximal end side from the protruding section 18. The third operation unit 13 is connected to the proximal end section of the bridge section 13B. A force generated in accordance with the operation of the third operation unit 13 is transmitted to the coupling section 1C via the bridge section 13B, and causes the coupling section 1C to move in the extending direction.

Sixth Moving Member 4B

Figure 33:
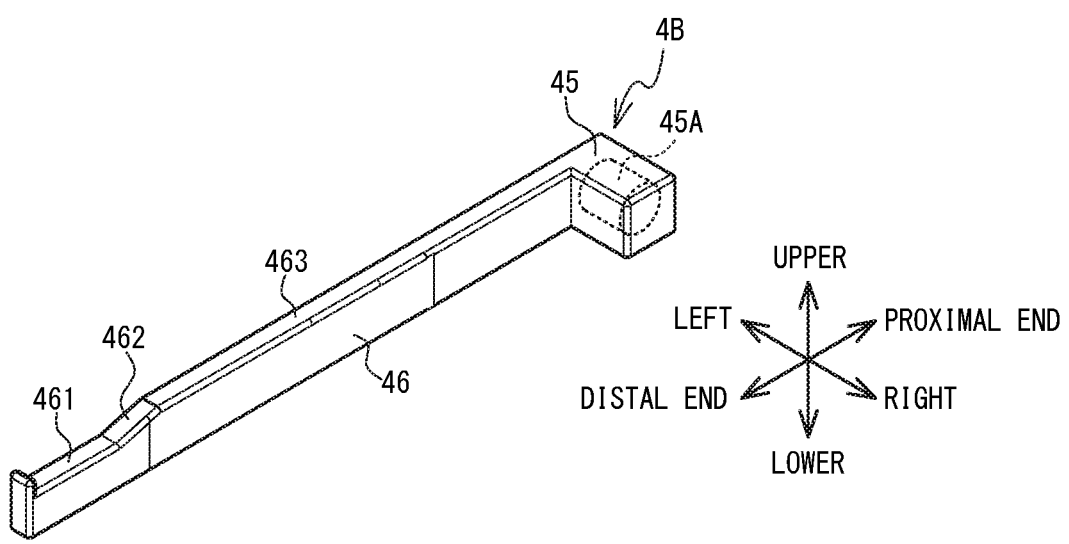
FIG. 33 is a perspective view of a sixth moving member 4B.

As shown in FIG. 23 to FIG. 25, in the interior of the housing 1, the sixth moving member 4B is disposed to the left of the fifth moving member 3C and the coupling section 1C. The sixth moving member 4B moves in the extending direction in accordance with the operation of the first operation unit 12, and switches a state of the restricting mechanism 4C (refer to FIG. 34 and FIG. 35) to be described later. Hereinafter, a position of the sixth moving member 4B that has moved furthest to the proximal end side is referred to as the "sixth proximal end position" (refer to FIG. 36 to FIG. 43), and a position of the sixth moving member 4B that has moved furthest to the distal end side is referred to as the "sixth distal end position" (refer to FIG. 44 to FIG. 47). In the initial state in which the hemostatic device 20 is not being used, the sixth moving member 4B is disposed in the sixth proximal end position (refer to FIG. 36 and FIG. 37). As shown in FIG. 33, the sixth moving member 4B includes a base section 45 and an extending section 46.

The base section 45 is a substantially cuboid shape that is long in the left-right direction. The base section 45 is disposed to the proximal end side of the protruding section 371 (refer to FIG. 31) of the fifth moving member 3C (refer to FIG. 37, FIG. 39, FIG. 41, FIG. 43, and FIG. 45). A magnet 45A is built into the base section 45. The extending section 46 has a plate shape, and extends to the distal end side from the left end section of the base section 45. The extending section 46 includes a first portion 461, a second portion 462, and a third portion 463 on the upper section thereof. The first portion 461 extends in the extending direction toward the proximal end side, from the distal end section of the extending section 46. The second portion 462 extends while inclining diagonally upward toward the proximal end side, from the proximal end section of the first portion 461. The third portion 463 extends in the extending direction toward the proximal end side, from the proximal end section of the second portion 462.

Restricting Mechanism 4C

Figure 34:
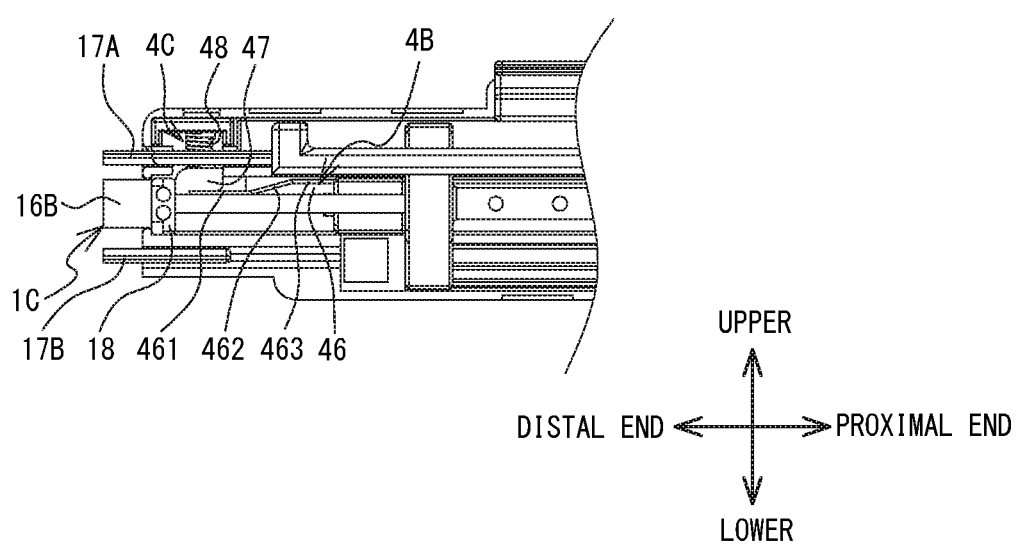
FIG. 34 is side view of a restricting mechanism 4C in a restricting state.
Figure 35:
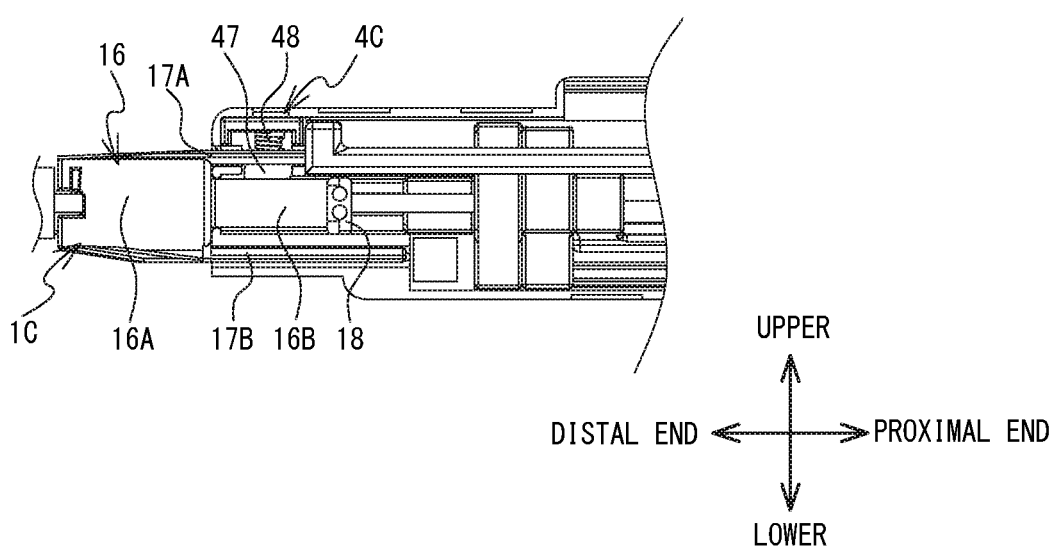
FIG. 35 is a side view of the restricting mechanism 4C in an enabling state.

As shown in FIG. 34 and FIG. 35, in the interior of the housing 1, the restricting mechanism 4C is disposed further to the left than the proximal end tubular section 16B of the coupling section 1C and above the extending section 46 of the sixth moving member 4B. The restricting mechanism 4C includes a limiting section 47 and an urging section 48. The limiting section 47 is a substantially cuboid shape. The urging section 48 is disposed above the limiting section 47. The urging section 48 is a compression coil spring. The upper end section of the urging section 48 is connected to the inner wall of the housing 1. The lower end section of the urging section 48 is connected to the upper end section of the limiting section 47. An urging force in the downward direction, which results from the elastic force of the urging section 48, acts on the limiting section 47.

FIG. 34 shows a state in which the sixth moving member 4B is disposed in the sixth proximal end position. In this state, the limiting section 47 of the restricting mechanism 4C comes into contact with the first portion 461 of the extending section 46 of the sixth moving member 4B. In accordance with the urging force of the urging section 48, the limiting section 47 is pushed, from above, against the first portion 461 of the extending section 46. Hereinafter, a position, in the up-down direction, of the limiting section 47 in the state in which the limiting section 47 is in contact with the first portion 461 of the extending section 46 of the sixth moving member 4B is referred to as the "restricting position." The limiting section 47 in the state of being disposed in the restricting position comes into contact with the surface on the proximal end side of the protruding section 18 of the coupling section 1C that is in the state of being disposed in the coupling distal end position. In this case, the limiting section 47 is disposed in a movement region in the extending direction of the protruding section 18 of the coupling section 1C (hereinafter referred to as the "second movement region"), and thus, the movement of the coupling section 1C to the proximal end side is restricted by the limiting section 47. Note that, in the initial state in which the hemostatic device 20 is not being used, the limiting section 47 is disposed in the restricting position.

In the course of the sixth moving member 4B moving from the sixth proximal end position to the sixth distal end position, the limiting section 47 of the restricting mechanism 4C comes into contact, in order, with the first portion 461, the second portion 462, and the third portion 463 of the extending section 46 of the sixth moving member 4B, and moves upward in resistance to the urging force of the urging section 48. As shown in FIG. 35, when the sixth moving member 4B is disposed in the sixth distal end position, the limiting section 47 of the restricting mechanism 4C is in contact with the third portion 463 of the extending section 46 of the sixth moving member 4B. Hereinafter, a position, in the up-down direction, of the limiting section 47 in a state in which the limiting section 47 is in contact with the third portion 463 of the extending section 46 of the sixth moving member 4B is referred to as the "enabling position." The limiting section 47 that is disposed in the enabling position is disposed higher than the limiting section 47 that is disposed in the restricting position. The limiting section 47 in the state of being disposed in the enabling position is disposed higher than the second movement region. In this case, the movement in the extending direction of the coupling section 1C is not restricted by the limiting section 47.

Hemostasis Operation

An operation of hemostasis of the puncture hole by the hemostatic agent S, using the hemostatic device 20, will be explained with reference to FIG. 36 to FIG. 47. An explanation of operations that are the same as those of the first embodiment will be simplified or omitted.

Figure 36:
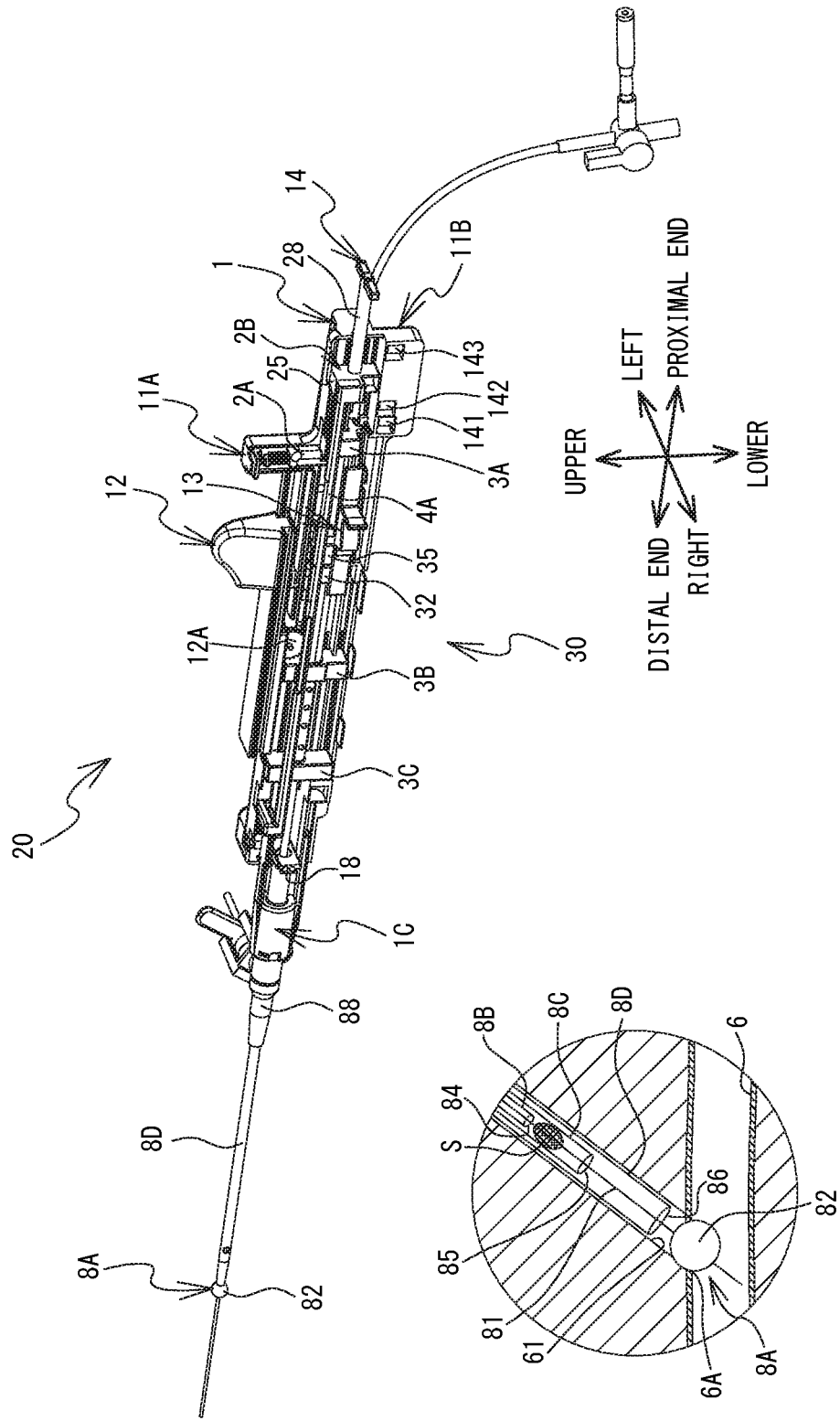
FIG. 36 is a perspective view showing an initial state of a hemostasis operation.
Figure 37:
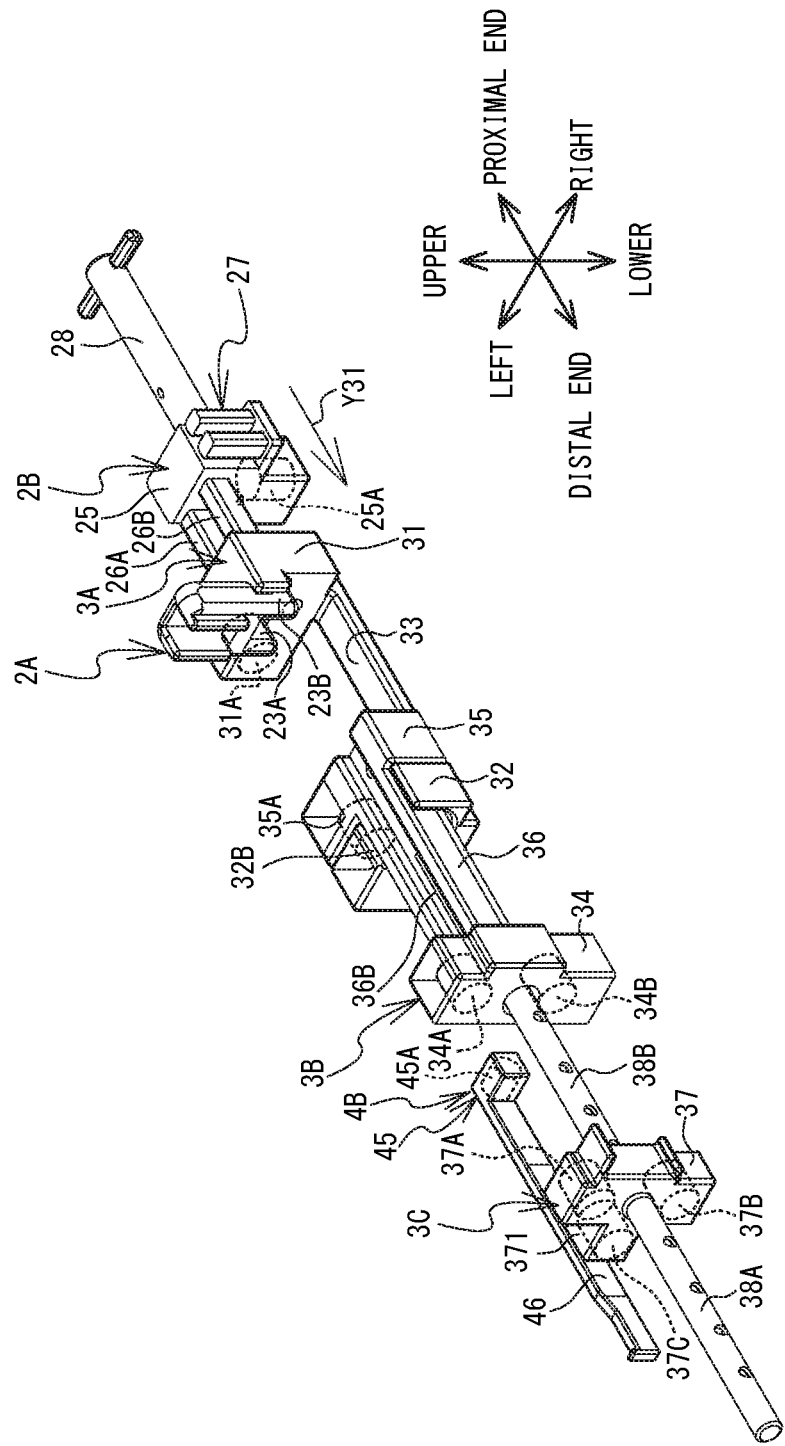
FIG. 37 is a perspective view showing a state of each of the moving members in a state shown in FIG. 36.

After the medical treatment via the puncture hole 61 is complete, as shown in FIG. 36 and FIG. 37, the hemostatic device 20 is prepared in which the restricting member 2A is in the restricting state, the switching member 2B is in the initial switching position, the first moving member 3A is in the first proximal end position, the fourth moving member 3B is in the fourth proximal end position, the fifth moving member 3C is in the fifth distal end position, the sixth moving member 4B is in the sixth proximal end position, and the coupling section 1C is in the coupling distal end position, respectively.

As shown in FIG. 37, when the hemostatic device 20 is in the above-described state, the restricting member 2A is in the restricting state, and thus, the limiting sections 23A and 23B of the restricting member 2A engage, from the distal end side, with the second engagement sections 311 and 312 (refer to FIG. 28) of the first moving member 3A and are disposed in the first movement region of the first moving member 3A. As a result, the movement of the first moving member 3A in the extending direction is restricted by the limiting sections 23A and 23B. Thus, the movement of the push-out member 8B connected to the first moving member 3A is also restricted. Since the sixth moving member 4B is disposed in the sixth proximal end position, the limiting section 47 (refer to FIG. 34) of the restricting mechanism 4C is disposed in the restricting position. Thus, the movement to the proximal end side of the coupling section 1C disposed in the coupling distal end position is restricted by the restricting mechanism 4C (refer to FIG. 34).

The same pre-operation as that of the first embodiment is performed. As shown in FIG. 36, in the pre-operation, the compressed fluid is supplied from the hub, and thus, the first engagement section 82 of the positioning member 8A expands inside the blood vessel 6. In this state, the user holds the housing 1 of the hemostatic device 20 and applies pressure, and moves the housing 1 toward the side (the proximal end side) in which the second tubular member 8D is pulled out from the puncture hole 61. In this way, the first engagement section 82 that is expanded inside the blood vessel 6 engages, from the inside, with the opening 6A formed in the blood vessel 6. The user moves the housing 1 further to the proximal end side. In this way, the positioning member 8A moves relatively to the distal end side with respect to the housing 1. As shown in FIG. 37, the switching member 2B that is connected to the positioning member 8A also moves relatively to the distal end side with respect to the first moving member 3A (refer to an arrow Y31 in FIG. 37).

Figure 38:
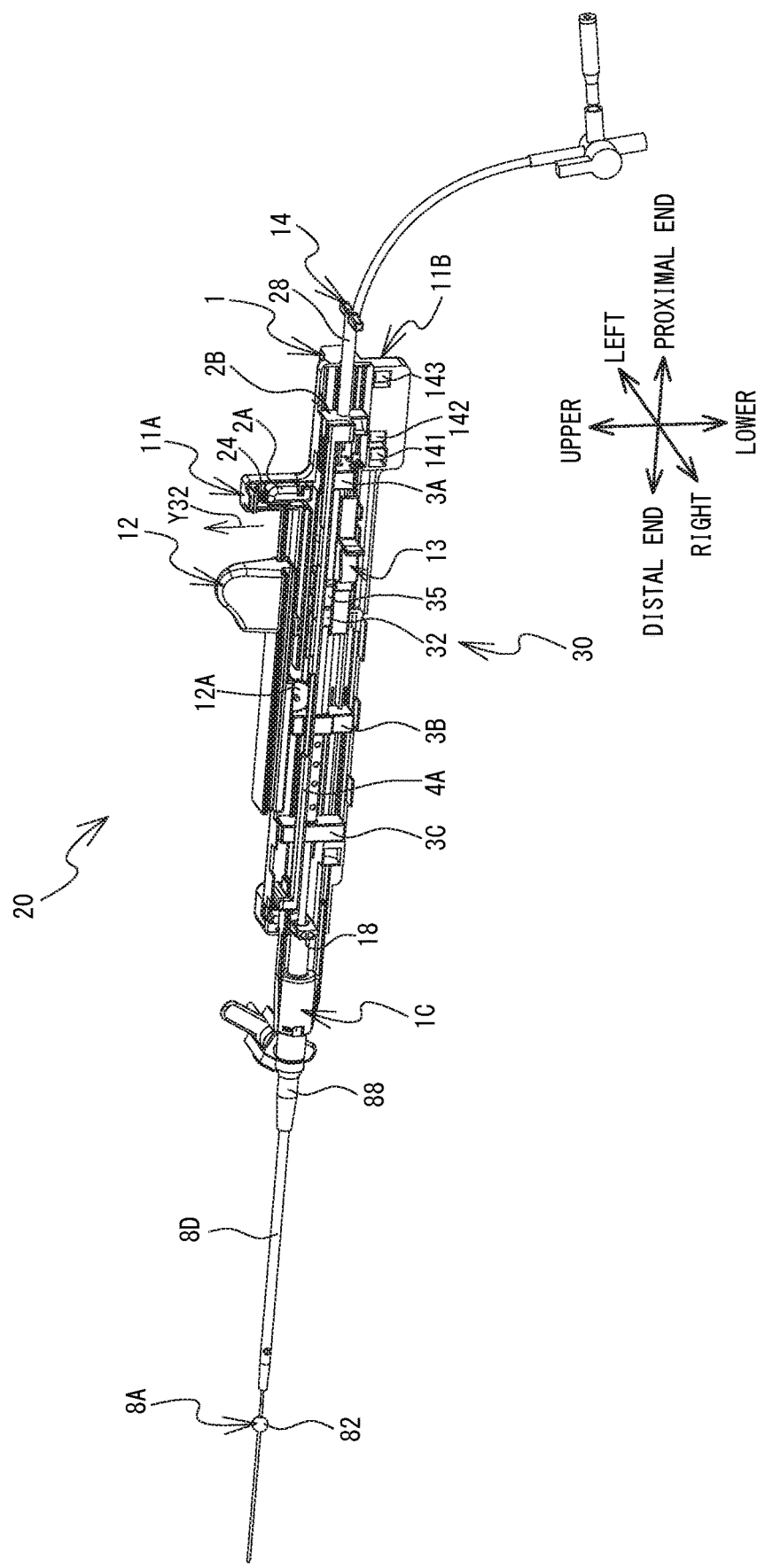
FIG. 38 is a perspective view showing a case in which the restricting member 2A is in an enabling state.
Figure 39:
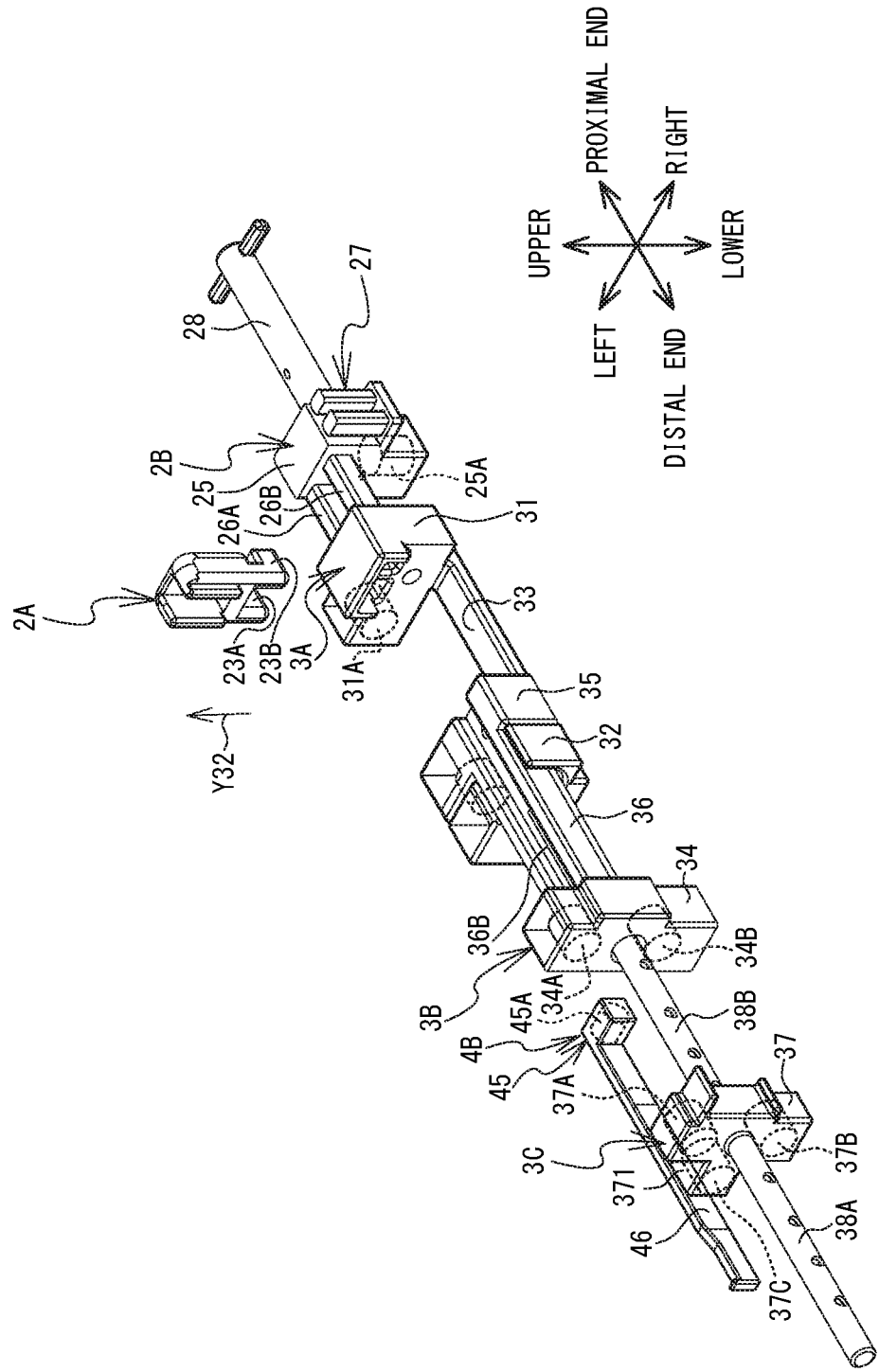
FIG. 39 is a perspective view showing a state of each of the moving members in a state shown in FIG. 38.

When the switching member 2B has moved from the initial switching position to the second switching position, the protruding sections 26A and 26B of the switching member 2B protrude to the distal end side from the second engagement sections 311 and 312 (refer to FIG. 28) of the first moving member 3A. In this way, the engagement of the limiting sections 23A and 23B with respect to the second engagement sections 311 and 312 of the first moving member 3A is released. In this case, as shown in FIG. 38, the restricting member 2A moves upward (an arrow Y32) in accordance with the urging force of the urging section 24, and the restricting member 2A switches from the restricting position to the enabling position. As shown in FIG. 39, the limiting sections 23A and 23B are no longer disposed in the first movement region of the first moving member 3A, and thus, the first moving member 3A is in a state of being able to move through the first movement region.

After the position of the restricting member 2A has once switched from the restricting state to the enabling state, even if the force applied to the housing 1 by the user is released, the restricting member 2A does not return to the original restricting state. In other words, when the engagement of the limiting sections 23A and 23B with respect to the first moving member 3A is once released and the restricting member 2A is in the enabling state, the restricting member 2A is maintained in the enabling state, and does not return to the original restricting state.

As shown in FIG. 39, when the switching member 2B has moved from the initial switching state to the second switching state in accordance with the user moving the housing 1 of the hemostatic device 20 to the proximal end side, the magnet 25A built into the switching member 2B faces the magnet 142 (refer to FIG. 38) of the housing 1, from above. Here, as shown in FIG. 38, the thickness of the partition walls on the upper side of the housing sections 14B and 14C housing the magnets 142 and 143 is thinner than the thickness of the partition wall on the upper side of the housing section 14A (refer to FIG. 24). Thus, when the switching member 2B is disposed in the second switching position, the magnetic force that acts between the magnet 25A of the switching member 2B and the magnet 142 of the housing 1 is relatively large, compared to when the switching member 2B is disposed in the first switching position. Thus, since the magnetic force that acts between the magnets 25A and 142 is also relatively large, the movement of the switching member 2B to the distal end side is inhibited by the magnetic force. As a result, after the restricting member 2A is switched from the restricting state to the enabling state by the user moving the housing 1 to the proximal end side, the movement of the switching member 2B further to the distal end side from the second switching position is inhibited by the magnet 142.

In the state in which the switching member 2B is disposed in the second switching position, the exposed section 43 of the second moving member 4A is disposed below the notification section 15 of the housing 1. In this case, the user can visually observe the exposed section 43 via the notification section 15. Thus, by visually observing the exposed section 43 via the notification section 15, the user can recognize that the restricting member 2A has switched from the restricting state to the enabling state in accordance with the switching member 2B having moved to the second switching position.

When a force by which the user further moves the housing 1 to the proximal end side is large, there is a possibility that the switching member 2B may go beyond the second switching position, and may move to the distal end side as far as the first switching position. In this case, the magnet 25A of the switching member 2B faces the magnet 11 (refer to FIG. 38) of the housing 1, from above. The movement of the switching member 2B to the distal end side is inhibited by the magnetic force acting between the magnets 25A and 141. When the switching member 2B has moved as far as the first switching position, the exposed section 43 of the second moving member 4A is no longer exposed from the notification section 15 of the housing 1. Thus, since the user cannot visually observe the exposed section 43 via the notification section 15, the user can recognize that the force to move the housing 1 to the proximal end side is excessive.

First Distal End Operation

Figure 40:
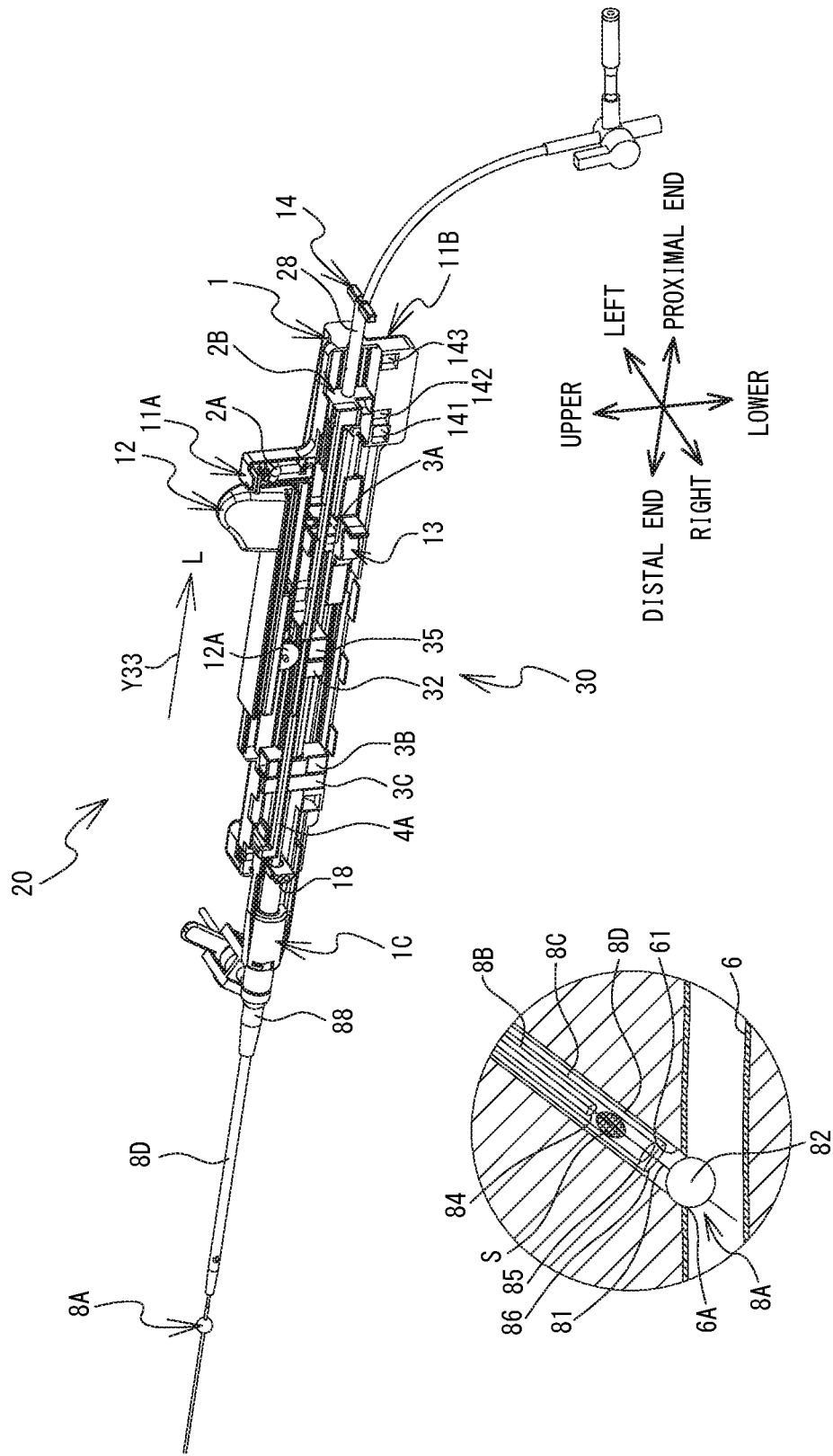
FIG. 40 is a perspective view showing the first distal end operation.

In the hemostatic device 20, when the restricting member 2A is in the enabling state, the first moving member 3A can move in the extending direction. As shown in FIG. 40, in this state, the user performs an operation to move the first operation unit 12 to the proximal end side by a predetermined amount L (refer to an arrow Y33). The pinion gear 12A provided below the first operation unit 12 rotates, and the fourth moving member 3B moves to the distal end side from the fourth proximal end position to the fourth distal end position (refer to an arrow Y34 in FIG. 41).

Figure 41:
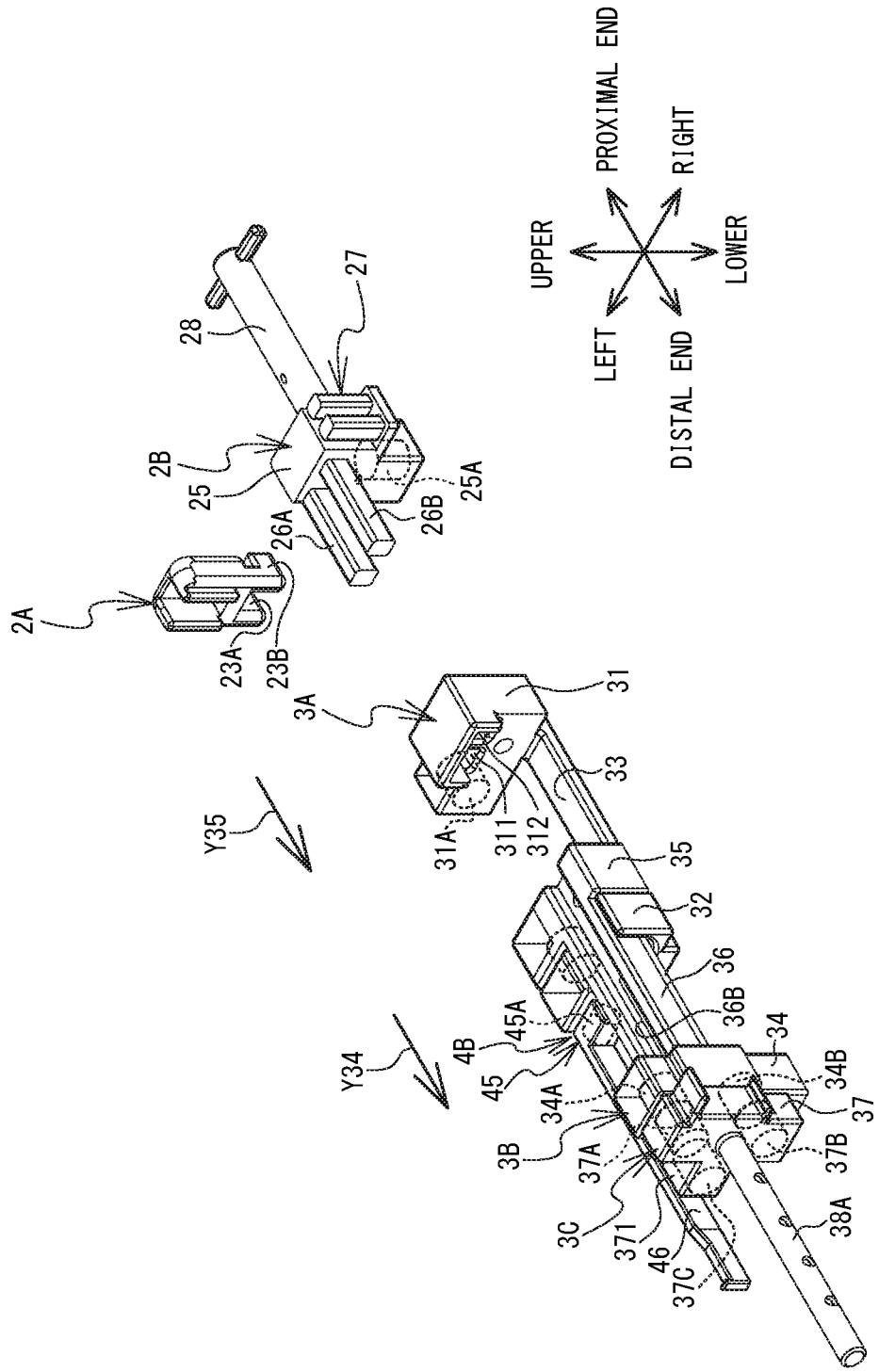
FIG. 41 is a perspective view showing a state of each of the moving members in a state shown in FIG. 40.

As shown in FIG. 41, in accordance with the fourth moving member 3B moving to the distal end side, the first base section 34 of the fourth moving member 3B comes into contact, from the proximal end side, with the base section 37 of the fifth moving member 3C disposed in the fifth distal end position. As a result of the magnetic force acting between the magnets 34A and 34B of the fourth moving member 3B and the magnets 37A and 37B of the fifth moving member 3C, the fourth moving member 3B and the fifth moving member 3C are attracted to each other. Further, the second base section 32 of the first moving member 3A comes into contact with the distal end side of the second base section 35 of the fourth moving member 3B and is disposed. In accordance with the magnetic force acting between the magnet 35A of the fourth moving member 3B and the magnet 31A of the first moving member 3A, the first moving member 3A moves to the distal end side along with the movement of the fourth moving member 3B. In this way, the first moving member 3A moves to the distal end side from the first proximal end position to the first intermediate position (refer to an arrow Y35). In other words, the first moving member 3A and the fourth moving member 3B move to the distal end side in a state of being in mutual contact, due to the operation of the first operation unit 12. Hereinafter, the above-described operation resulting from the operation of the first operation unit 12 is referred to as the "first distal end operation."

As shown in FIG. 40, by the first distal end operation, the push-out member 8B connected to the first moving member 3A, and the first tubular member 8C connected to the fourth moving member 3B move to the distal end side. On the other hand, the positioning member 8A connected to the switching member 2B, and the second tubular member 8D connected to the coupling section 1C do not move. In other words, the push-out member 8B and the first tubular member 8C move relatively to the distal end side with respect to the housing 1, the positioning member 8A, and the second tubular member 8D. In this way, the hemostatic agent S is pressed to the distal end side by the push-out member 8B in a state in which the hemostatic agent S is disposed in the vicinity of the first distal end 85 inside the first tubular member 8C, and the hemostatic agent S moves to the vicinity of the second distal end 86 inside the second tubular member 8D.

Tube Proximal End Operation

Figure 42:
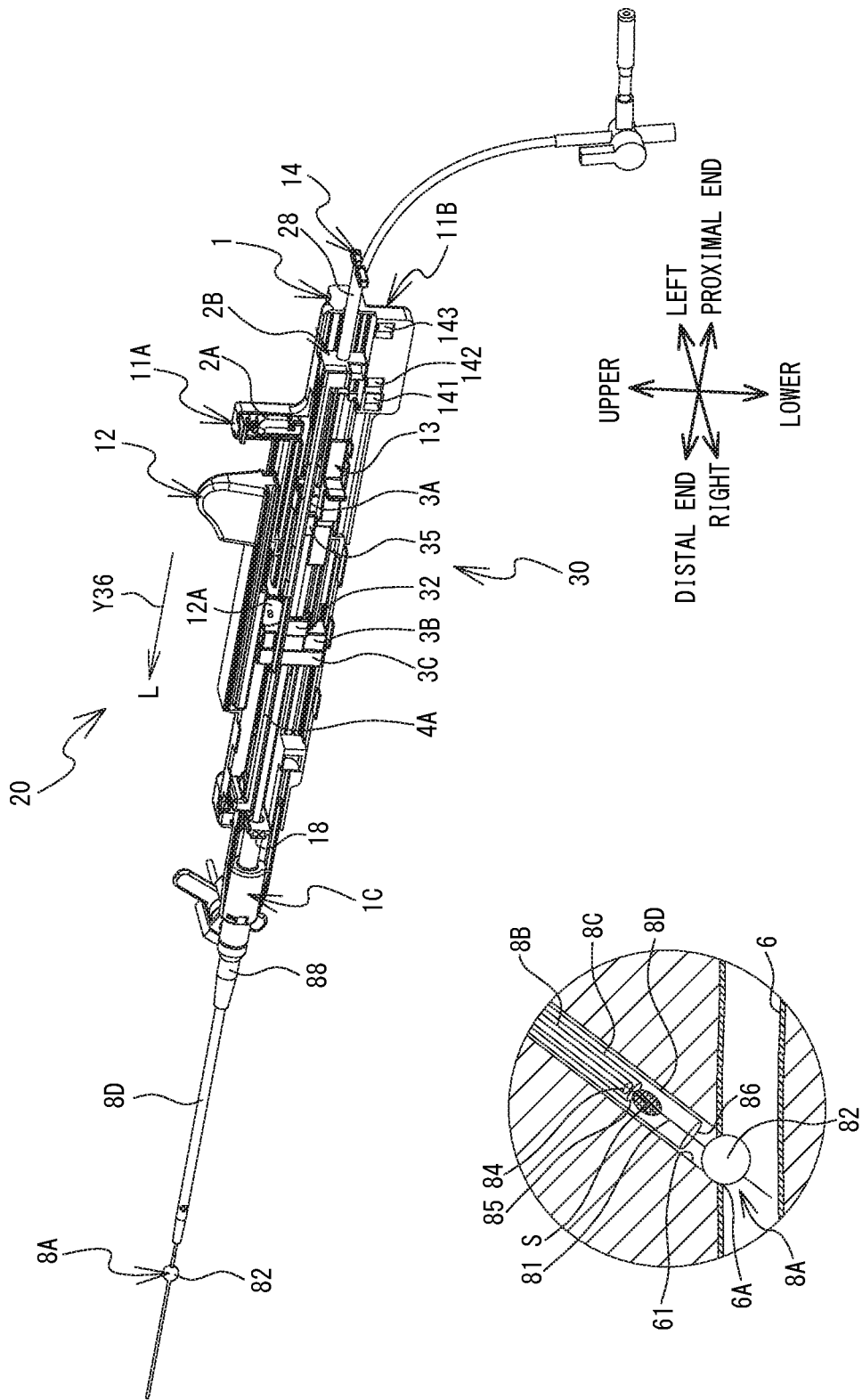
FIG. 42 is a perspective view showing a tube proximal end operation.

As shown in FIG. 42, next, the user performs the operation to move the first operation unit 12 to the distal end side by the predetermined amount L (refer to an arrow Y36). The pinion gear 12A provided below the first operation unit 12 rotates, and the fourth moving member 3B moves from the fourth distal end position to the fourth proximal end position (refer to an arrow Y37 in FIG. 43).

Figure 43:
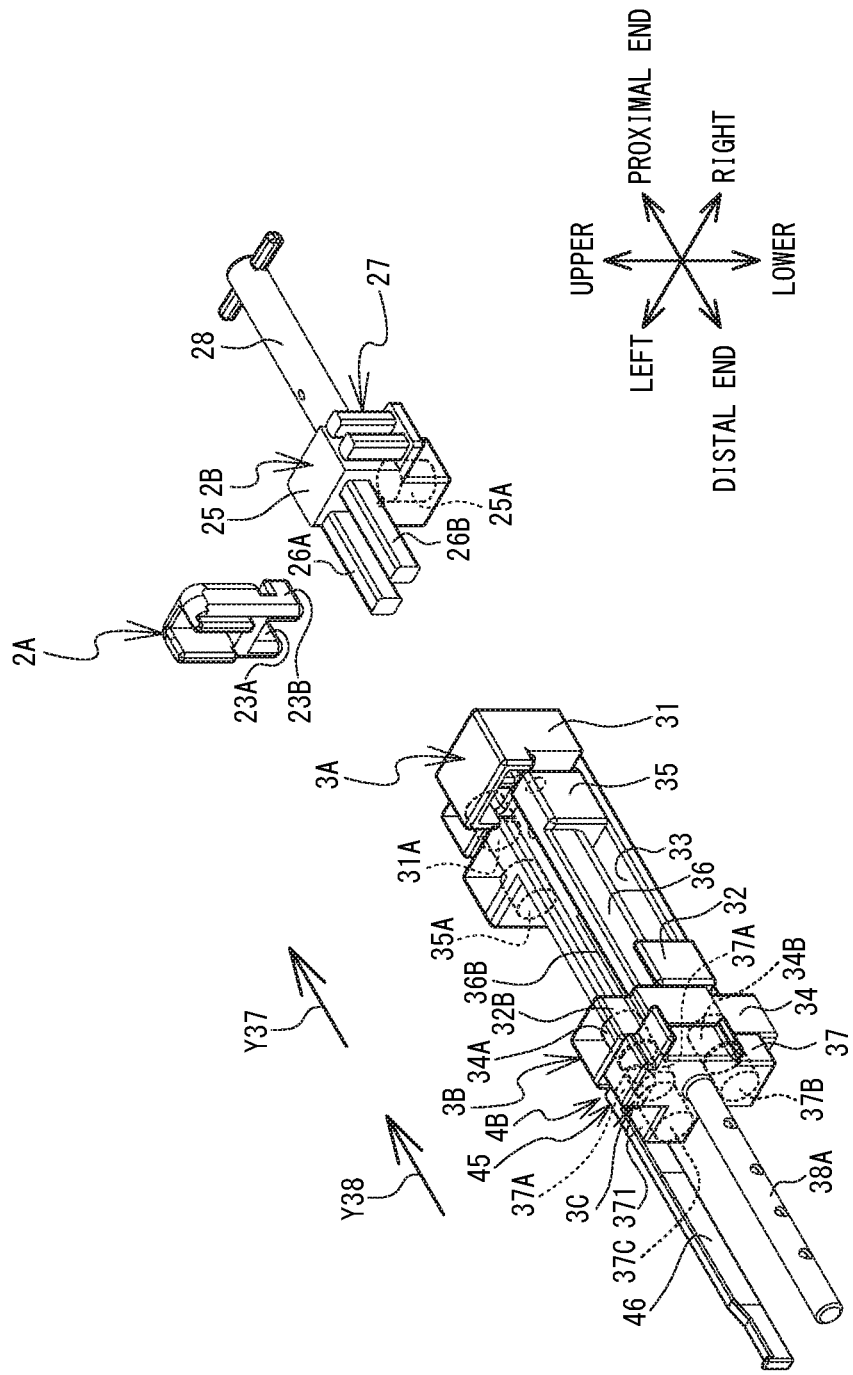
FIG. 43 is a perspective view showing a state of each of the moving members in a state shown in FIG. 42.

As shown in FIG. 43, the base section 37 of the fifth moving member 3C that is attracted by the magnetic force acting between the magnets 34A and 34B and the magnets 37A and 37B comes into contact with the first base section 34 of the fourth moving member 3B. In accordance with the movement to the proximal end side of the fourth moving member 3B, the fifth moving member 3C moves to the proximal end side from the fifth distal end position to the fifth proximal end position (refer to an arrow Y38). The protruding section 371 of the fifth moving member 3C comes into contact with the base section 45 of the sixth moving member 4B, from the distal end side. As a result of the magnetic force acting between the magnet 37C of the fifth moving member 3C, and the magnet 45A of the sixth moving member 4B (refer to FIG. 33), the fifth moving member 3C and the sixth moving member 4B are attracted to each other.

On the other hand, even if the fourth moving member 3B has moved to the proximal end side, the first moving member 3A does not move, and is maintained in the first intermediate position. Thus, in accordance with the movement of the fourth moving member 3B, the second base section 35 of the fourth moving member 3B, and the second base section 32 of the first moving member 3A separate from each other. The first base section 34 of the fourth moving member 3B comes into contact with the second base section 32 of the first moving member 3A, from the distal end side, and the second base section 35 of the fourth moving member 3B comes into contact with the first base section 31 of the first moving member 3A, from the distal end side. As a result of the magnetic force acting between the magnet 35A of the fourth moving member 3B and the magnet 31A of the first moving member 3A, the fourth moving member 3B and the first moving member 3A are attracted to each other. Hereinafter, the above-described operation resulting from the operation of the first operation unit 12 is referred to as a "tube distal end operation." Until the first distal end operation is complete, the first moving member 3A and the fourth moving member 3B restrict the tube distal end operation, and once the first distal end operation is complete, the restriction on the tube distal end operation is released and the tube distal end operation can be performed.

As shown in FIG. 42, as a result of the tube distal end operation, the fourth moving member 3B moves to the proximal end side in the state of being separated from the first moving member 3A. In this way, the first tubular member 8C connected to the fourth moving member 3B moves to the proximal end side. On the other hand, the positioning member 8A connected to the switching member 2B, the push-out member 8B connected to the first moving member 3A, and the second tubular member 8D connected to the coupling section 1C do not move. In other words, the first tubular member 8C moves relatively to the proximal end side with respect to the housing 1, the push-out member 8B, the positioning member 8A, and the second tubular member 8D. In this way, in a state in which the push-out distal end 84 of the push-out member 8B holds the position, on the proximal end side, of the hemostatic agent S, the first tubular member 8C moves until the first distal end 85 is disposed further to the proximal end side than the hemostatic agent S. In this way, the hemostatic agent S is exposed from the first tubular member 8C. The hemostatic agent S is disposed further to the distal end side than the push-out distal end 84 of the push-out member 8B and the first distal end 85 of the first tubular member 8C, and is disposed inside the second tubular member 8D.

Second Distal End Operation

Figure 44:
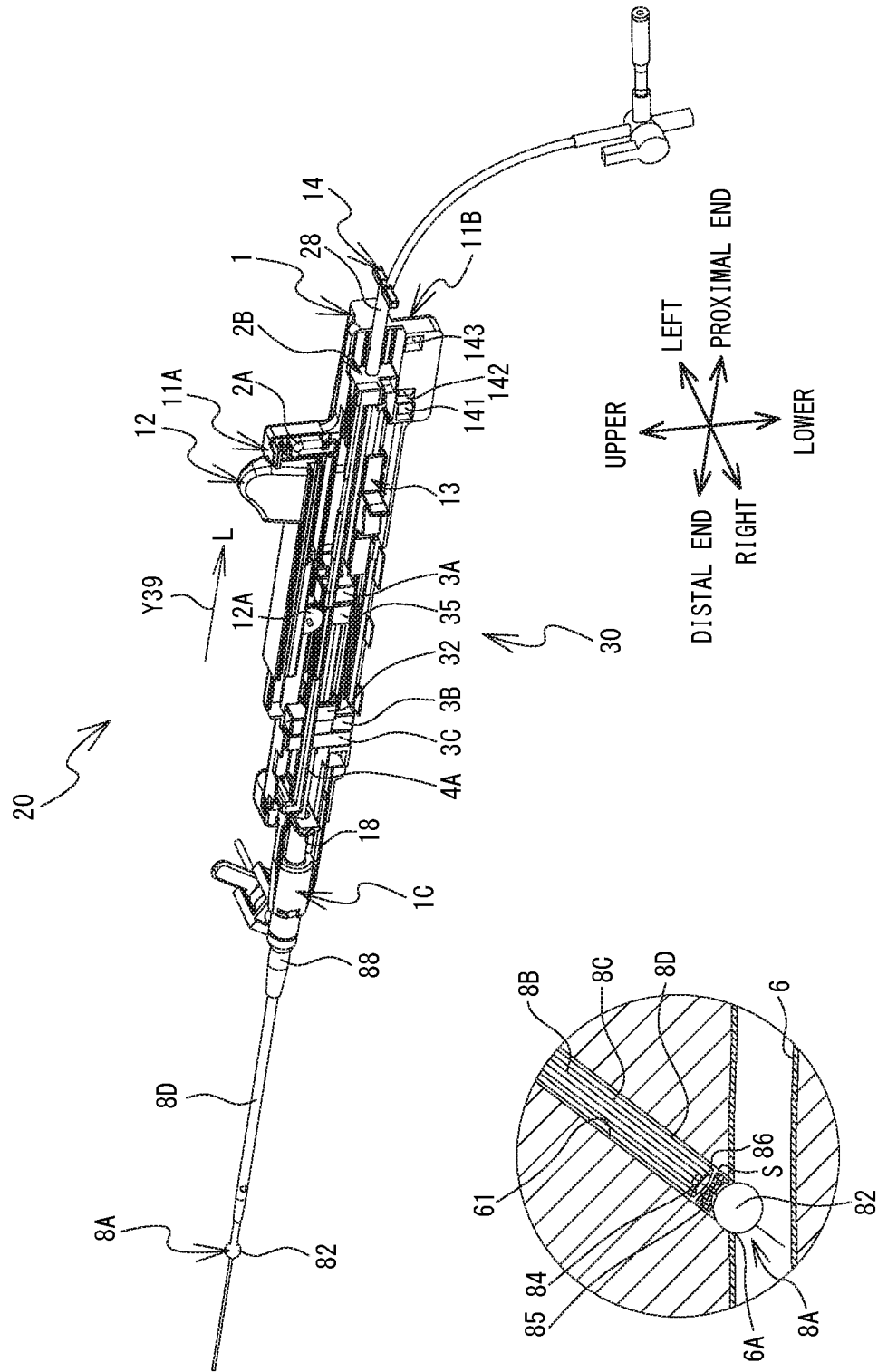
FIG. 44 is a perspective view showing the second distal end operation.

As shown in FIG. 44, next, the user performs an operation to move the first operation unit 12 to the proximal end side by the predetermined amount L (refer to an arrow Y39). In accordance with the rotation of the pinion gear 12A provided below the first operation unit 12, the fourth moving member 3B moves to the proximal end side from the fourth proximal end position to the fourth distal end position (refer to an arrow Y40 in FIG. 45).

Figure 45:
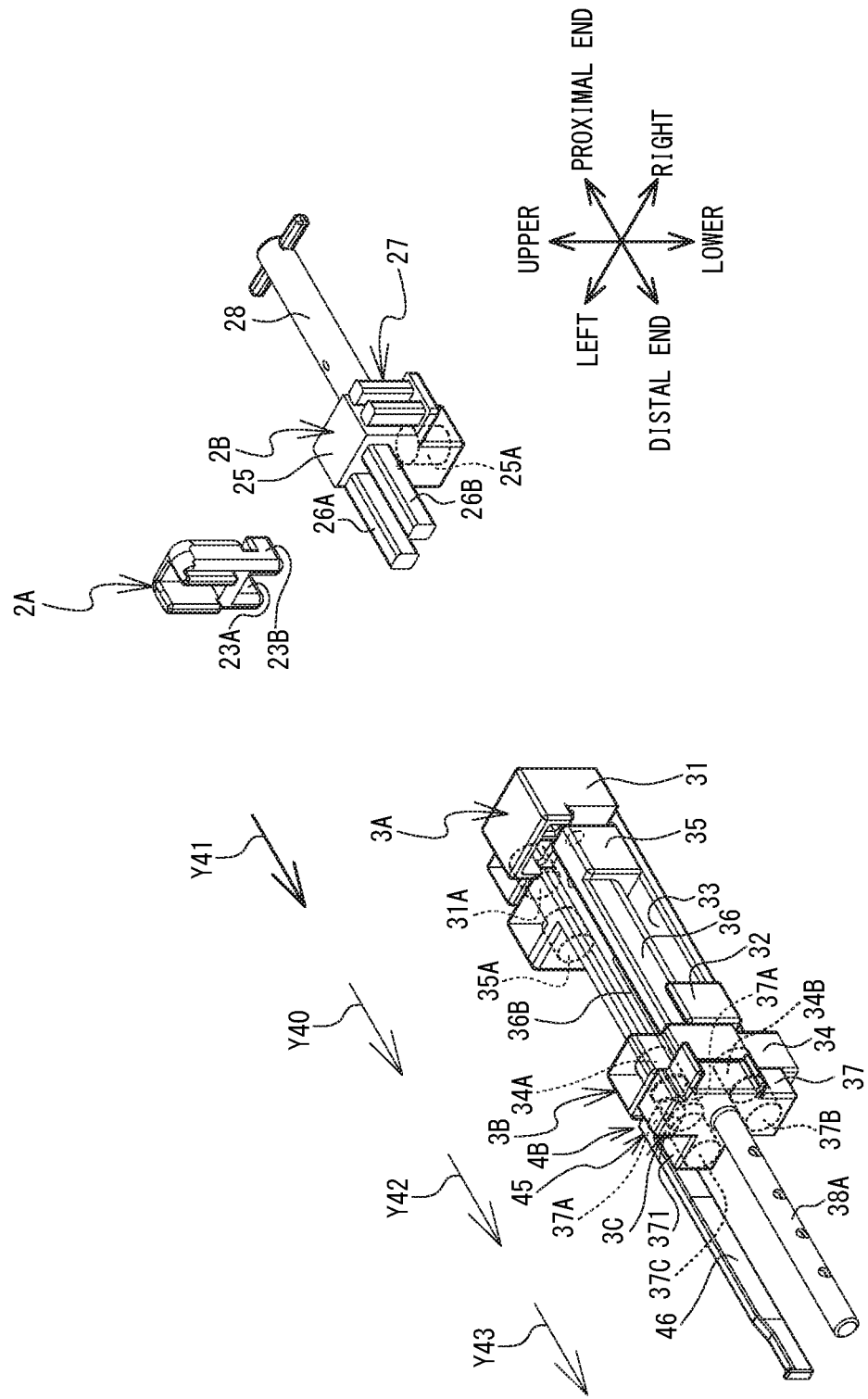
FIG. 45 is a perspective view showing a state of each of the moving members in a state shown in FIG. 44.

As shown in FIG. 45, the first base section 31 of the first moving member 3A that is attracted due to the magnetic force between the magnets 31A and 35A is in contact with the second base section 35 of the fourth moving member 3B.

In accordance with the fourth moving member 3B moving to the distal end side, the first moving member 3A moves to the distal end side from the first intermediate position to the first distal end position (refer to an arrow Y41).

The base section 37 of the fifth moving member 3C that is attracted due to the magnetic force between the magnets 34A and 34B and the magnets 37A and 37B is in contact with the first base section 34 of the fourth moving member 3B. In accordance with the fourth moving member 3B moving to the distal end side, the fifth moving member 3C moves to the distal end side from the fifth proximal end position to the fifth distal end position (refer to an arrow Y42). The sixth moving member 4B that is attracted due to the magnetic force between the magnets 37A and 45A is in contact with the protruding section 371 of the fifth moving member 3C. In accordance with the fifth moving member 3C moving to the distal end side, the sixth moving member 4B moves to the distal end side from the sixth proximal end position to the sixth distal end position (refer to an arrow Y43). Hereinafter, the above-described operation resulting from the operation of the first operation unit 12 is referred to as the "second distal end operation." The first moving member 3A, the fourth moving member 3B, and the sixth moving member 4B restrict the second distal end operation until the tube proximal end operation is complete, and once the tube proximal end operation is complete, the restriction on the second distal end operation is released and the second distal end operation can be performed.

As shown in FIG. 44, as a result of the second distal end operation, the first tubular member 8C connected to the fourth moving member 3B, and the push-out member 8B connected to the first moving member 3A move to the distal end side. On the other hand, the positioning member 8A connected to the switching member 2B and the second tubular member 8D connected to the coupling section 1C do not move. In other words, the first tubular member 8C and the push-out member 8B move relatively to the distal end side with respect to the housing 1, the positioning member 8A, and the second tubular member 8D. In this way, the hemostatic agent S is moved to the distal end side by the push-out member 8B, in a state in which the hemostatic agent S is disposed further to the distal end side than the push-out distal end 84 of the push-out member 8B and the first distal end 85 of the first tubular member 8C. In the vicinity of the second distal end 86 of the second tubular member 8D, the hemostatic agent S is pushed, from the proximal end side, against the first engagement section 82 of the positioning member 8A. In this way, the hemostatic agent S closes the opening 6A of the blood vessel 6 with which the first engagement section 82 engages.

In accordance with the sixth moving member 4B moving to the sixth distal end position as a result of the second distal end operation, the limiting section 47 (refer to FIG. 34 and FIG. 35) of the restricting mechanism 4C moves from the restricting position (refer to FIG. 34) to the enabling position (refer to FIG. 35). In this case, the limiting section 47 moves from the state of being disposed in the second movement region to the state of not being disposed in the second movement region. As a result, the coupling section 1C can move from the coupling distal end position toward the coupling proximal end position. In other words, in accordance with the push-out member 8B having moved to the distal end side during the second distal end operation, the coupling section 1C is in a state of being able to move relatively to the proximal end side with respect to the housing 1, the positioning member 8A, the push-out member 8B, and the first tubular member 8C.

Coupling Proximal End Operation

As shown in FIG. 46, next, the user performs an operation to move the third operation unit 13 to the proximal end side (refer to an arrow Y44). The third operation unit 13 is connected to the coupling section 1C via the bridge section 13B. As a result of the second distal end operation, the coupling section 1C is in the state of being able to move to the proximal end side from the coupling distal end position toward the coupling proximal end position. Thus, in accordance with the operation of the third operation unit 13, the coupling section 1C moves from the coupling distal end position to the coupling proximal end position (refer to an arrow Y45). Hereinafter, the above-described operation resulting from the operation of the third operation unit 13 is referred to as the "coupling proximal end operation." In other words, until the second distal end operation is complete, the coupling proximal end operation is restricted by the limiting section 47 being disposed in the restricting position. On the other hand, the limiting section 47 is switched to the enabling position by the completion of the second distal end operation, and as a result, the restriction on the coupling proximal end operation is released and the coupling proximal end operation can be performed.

By the coupling proximal end operation, the second tubular member 8D coupled to the coupling section 1C moves to the proximal end side. On the other hand, the positioning member 8A connected to the switching member 2B, the push-out member 8B connected to the first moving member 3A, and the first tubular member 8C connected to the fourth moving member 3B do not move. In other words, the second tubular member 8D moves relatively to the proximal end side with respect to the housing 1, the positioning member 8A, the push-out member 8B, and the first tubular member 8C. In this case, the second distal end 86 of the second tubular member 8D separates, to the proximal end side, from the hemostatic agent S that is in the state of closing the opening 6A of the blood vessel 6.

Positioning Proximal End Operation

Next, the user removes, via the hub, the compressed fluid supplied to the first engagement section 82, and causes the first engagement section 82 to contract. Next, as shown in FIG. 47, the user performs an operation to move the second operation unit 14 to the proximal end side (refer to an arrow Y46). The second operation unit 14 is connected to the switching member 2B. Thus, the switching member 2B moves to the proximal end side in accordance with the operation of the second operation unit 14, and the positioning member 8A connected to the switching member 2B also moves to the proximal end side. On the other hand, the push-out member 8B connected to the first moving member 3A, the first tubular member 8C connected to the fourth moving member 3B, and the second tubular member 8D connected to the coupling section 1C do not move. In other words, the positioning member 8A moves relatively to the proximal end side with respect to the push-out member 8B, the first tubular member 8C, and the second tubular member 8D. Hereinafter, the above-described operation resulting from the operation of the second operation unit 14 is referred to as the "positioning proximal end operation."

As a result of the positioning proximal end operation, the first engagement section 82 of the positioning member 8A moves further to the proximal end side than the push-out distal end 84 of the push-out member 8B, and is disposed inside the push-out member 8B. After that, the positioning member 8A, the hemostatic agent S, the push-out member 8B, the first tubular member 8C, and the second tubular member 8D are removed from the puncture hole 61.

Note that, in accordance with the user moving the second operation unit 14 to the proximal end side, the switching member 2B moves to the third switching position. The magnet 25A (refer to FIG. 39) built into the switching member 2B faces the magnet 143 (refer to FIG. 38) of the housing 1, from above. The magnetic force acting between the magnet 25A and the magnet 143 inhibits the switching member 2B from moving further to the proximal end side than the third switching position.

Operations and Effects of Second Embodiment

The same effects as those of the first embodiment are achieved. Further, the following effects unique to the second embodiment are achieved. In the hemostatic device 20, the first distal end operation is performed in the state in which the first engagement section 82 of the positioning member 8A is engaged with the opening 6A of the blood vessel 6. In the first distal end operation, the first tubular member 8C and the push-out member 8B move relatively to the distal end side with respect to the housing 1. As a result, the hemostatic device 20 can move the hemostatic agent S to the distal end side in the state in which the hemostatic agent S is held inside the first tubular member 8C, and can cause the hemostatic agent S to come close to the first engagement section 82 of the positioning member 8A. Further, in the proximal end operation, the first tubular member 8C moves relatively to the proximal end side with respect to the housing 1. As a result, the hemostatic agent S is pushed out from the first tubular member 8C using the push-out member 8B, and the hemostatic agent S is exposed in the vicinity of the first engagement section 82. Further, in the second distal end operation, the push-out member 8B moves relatively to the distal end side with respect to the housing 1. In this way, the push-out member 8B pushes the hemostatic agent S in the state of being exposed from the first tubular member 8C to a position at which the hemostatic agent S comes into contact with the first engagement section 82. The hemostatic device 20 closes the puncture hole 61 including the opening 6A of the blood vessel 6, using the hemostatic agent S.

The hemostatic device 20 restricts the tube proximal end operation until the first distal end operation is complete. Further, the hemostatic device 20 restricts the second distal end operation until the tube proximal end operation is complete. In this way, the hemostatic device 20 restricts the second distal end operation from being performed until the first distal end operation is complete. Thus, even when the hemostatic device 20 is erroneously operated, it is possible to inhibit the hemostatic agent S from being pushed out from the first tubular member 8C before the hemostatic agent S comes close to the first engagement section 82. As a result, the user can easily operate the hemostatic device 20 in the order of the first distal end operation and the second distal end operation.

The hemostatic device 20 includes the fourth moving member 3B connected to the first tubular member 8C, and the first moving member 3A connected to the push-out member 8B. In the first distal end operation and the second distal end operation, the first moving member 3A and the fourth moving member 3B move to the distal end side in accordance with the operation of the first operation unit 12, in the state of being in contact with each other, and the first tubular member 8C and the push-out member 8B move to the distal end side. In the tube proximal end operation, the fourth moving member 3B separates from the first moving member 3A, and, by the fourth moving member 3B moving relatively to the distal end side in accordance with the operation of the first operation unit 12, the first tubular member 8C moves to the distal end side. Thus, using the first tubular member 8C and the push-out member 8B, the hemostatic device 20 can easily realize a configuration for restricting the tube proximal end operation until the first distal end operation is complete, and a configuration for restricting the second distal end operation until the tube proximal end operation is complete.

The first distal end operation and the second distal end operation are performed by the first operation unit 12 moving to the proximal end side by the predetermined amount L. On the other hand, the tube proximal end operation is performed by the first operation unit 12 moving to the distal end side by the predetermined amount L. Thus, the user can cause the hemostatic device 20 to perform the first distal end operation, the tube proximal end operation, and the second distal end operation, simply by moving the first operation unit 12 back and forth in the extending direction by the predetermined amount L.

The hemostatic device 20 moves the hemostatic agent S toward the vicinity of the first engagement section 82 by relatively moving the push-out member 8B to the distal end side in the state in which the first engagement section 82 of the positioning member 8A is engaged with the opening 6A of the blood vessel 6. In this way, using the hemostatic agent S, the hemostatic device 20 can close the puncture hole 61 including the opening 6A with which the first engagement section 82 is engaged, and can stop the bleeding. The restricting member 2A can switch between the restricting state (refer to FIG. 36 and FIG. 37) that restricts the relative movement of the push-out member 8B to the distal end side, and the enabling state (refer to FIG. 38 and FIG. 39) that does not restrict the relative movement of the push-out member 8B to the distal end side.

In the state in which the first engagement section 82 of the positioning member 8A is engaged with the opening 6A of the blood vessel 6, the user moves the housing 1 to the proximal end side. In this case, the positioning member 8A moves relatively to the proximal end side with respect to the opening 6A, and the first engagement section 82 adheres closely to the opening 6A from the inside of the blood vessel 6. Further, in this case, the force in the direction toward the distal end with respect to the positioning member 8A acts in a relative manner, and the positioning member 8A moves relatively to the distal end side. When the positioning member 8A has moved relatively to the distal end side (refer to FIG. 36 and FIG. 37) when the restricting member 2A is in the restricting state, the switching member 2B switches the restricting member 2A to the enabling state (refer to FIG. 38 and FIG. 39). In other words, the movement of the push-out member 8B to the distal end side is enabled in the state in which the first engagement section 82 is closely adhered to the opening 6A from the inside. Thus, when the push-out member 8B moves relatively to the distal end side in this state and the hemostatic agent S has moved to the distal end side, the hemostatic agent S can appropriately close the puncture hole 61 and can stop the bleeding. In addition, since the first engagement section 82 is in the state of being closely adhered to the opening 6A, it is possible to inhibit the hemostatic agent S from entering into the blood vessel 6 though a gap between the first engagement section 82 and the opening 6A.

After the restricting member 2A has been switched from the restricting state to the enabling state, the restricting member 2A is maintained in the enabling state, irrespective of the relative movement of the positioning member 8A. In other words, the restricting member 2A does not return to the original restricting state after once being switched to the enabling state. Thus, after the operation to move the housing 1 to the proximal end side with respect to the positioning member 8A in order to engage the first engagement section 82 in the opening 6A is released, the user can perform the operation to relatively move the push-out member 8B to the distal end side. As a result, the user can easily perform the operation to relatively move the push-out member 8B to the distal end side.

The first moving member 3A can move relatively inside the first movement region. In the restricting state, the limiting sections 23A and 23B of the restricting member 2A are disposed in the first movement region. In this case, the restricting member 2A in the restricting state can inhibit the movement of the first moving member 3A in the first movement region, using the limiting sections 23A and 23B. Thus, with a simple configuration, the restricting member 2A can appropriately inhibit the push-out member 8B from moving relatively to the distal end side and pushing out the hemostatic agent S. On the other hand, in accordance with the positioning member 8A having moved relatively to the distal end side, the switching member 2B switches from the restricting state in which the limiting sections 23A and 23B of the restricting member 2A are disposed in the first movement region to the enabling state in which the limiting sections 23A and 23B are not disposed in the first movement region. Thus, using the movement of the limiting sections 23A and 23B of the restricting member 2A, the switching member 2B can easily perform the operation of switching from the state in which the first moving member 3A can move through the first movement region to the state in which the first moving member 3A cannot move through the first movement region.

The first moving member 3A is provided with the second engagement sections 311 and 312. In the state of being disposed in the first movement region, the limiting sections 23A and 23B of the restricting member 2A engage with the second engagement sections 311 and 312, and the restricting state is obtained. The switching member 2B switches from the state in which the limiting sections 23A and 23B are engaged with the second engagement sections 311 and 312 to the state in which the limiting sections 23A and 23B are not engaged with the second engagement sections 311 and 312. When the engagement of the limiting sections 23A and 23B with respect to the second engagement sections 311 and 312 has been released, the urging force of the urging section 24 of the restricting member 2A causes the limiting sections 23A and 23B to move, and the restricting member 2A enters into the enabling state. In this way, using the urging force of the urging section 24, the hemostatic device 20 can switch the restricting member 2A from the restricting state to the enabling state. Further, using the urging section 24, the hemostatic device 20 can easily realize the configuration in which, after the restricting member 2A switches from the restricting state to the enabling state, the restricting member 2A does not return to the original restricting state.

In accordance with the positioning member 8A moving relatively to the distal end side, the switching member 2B moves relatively to the distal end side with respect to the first moving member 3A. In this way, the switching member 2B switches from the state in which the limiting sections 23A and 23B of the restricting member 2A are engaged with the second engagement sections 311 and 312 of the first moving member 3A to the state in which the limiting sections 23A and 23B are not engaged with the second engagement sections 311 and 312. In this case, the switching member 2B can perform the switching of the engagement state of the limiting sections 23A and 23B with respect to the second engagement sections 311 and 312 in accordance with the relative movement of the positioning member 8A. Further, by causing the urging section 24 of the restricting member 2A to be the spring, the imparting of the force to urge the restricting member 2A from the restricting state to the enabling state can be easily realized.

In accordance with the relative position of the switching member 2B with respect to the housing 1, the exposed section 43 of the second moving member 4A can switch to the exposed state in which the exposed section 43 is exposed from the notification section 15. Thus, the hemostatic device 20 can notify the user, via the notification section 15, of the strength of the force acting on the positioning member 8A connected to the switching member 2B.

When the switching member 2B is disposed in the second switching position, the exposed section 43 is disposed below the notification section 15 of the housing 1. In this case, the user can visually observe the exposed section 43 via the notification section 15. On the other hand, when the switching member 2B is disposed in the first switching position, the exposed section 43 is disposed further to the distal end side than the notification section 15 of the housing 1. In this case, the user cannot visually observe the exposed section 43 via the notification section 15. In other words, in accordance with the strength of the force acting on the positioning member 8A when the user moves the housing 1 to the proximal end side, the hemostatic device 20 switches between the state in which the exposed section 43 can be visually observed via the notification section 15, and the state in which the exposed section 43 cannot be visually observed via the notification section 15. Thus, via the notification section 15, the hemostatic device 20 can easily perform notification about information indicating the strength of the force acting on the positioning member 8A.

The switching member 2B is provided with the magnet 25A. In the housing 1, the magnet 142 is provided that faces the magnet 25A when the switching member 2B is disposed in the second switching position. In this case, on the basis of the magnetic force acting between the magnets 25A and 142, it is possible to stabilize the state of the switching member 2B disposed in the second switching position. Thus, when the switching member 2B has moved relatively to the distal end side in accordance with the force acting on the positioning member 8A, the hemostatic device 20 can appropriately switch the restricting member 2A from the restricting state to the enabling state. Further, using the magnetic force acting between the magnets 25A and 142, the hemostatic device 20 can inhibit the switching member 2B from moving from the initial switching position to the first switching position via the second switching position.

The magnetic force between the magnets 25A and 142 when the switching member 2B is disposed in the second switching position is greater than the magnetic force between the magnets 25A and 141 when the switching member 2B is disposed in the first switching position. As a result, using the magnetic force acting between the magnets 25A and 142, the hemostatic device 20 can effectively inhibit the switching member 2B from moving from the initial switching position to the first switching position via the second switching position.

The housing 1 is further provided with the magnet 141 that is disposed to the distal end side of the magnet 142. When the switching member 2B is disposed in the first switching position, the magnets 25A and 141 face each other. In this case, after the switching member 2B has switched the restricting member 2A from the restricting state to the enabling state, the hemostatic device 20 can inhibit the switching member 2B from moving excessively to the distal end side, using the magnetic force acting between the magnets 25A and 141. It is thus possible to inhibit a situation in which the force acting on the opening 6A of the blood vessel 6 from the positioning member 8A becomes excessive as a result of the switching member 2B moving excessively to the distal end side, and the first engagement section 82 becomes disengaged from the opening 6A of the blood vessel 6.

Modified Examples

The present disclosure is not limited to the above-described embodiments, and various modifications are possible. In the hemostatic device 10, the configuration to restrict the second distal end operation until the first distal end operation is complete, and to release the restriction of the second distal end operation once the first distal end operation is complete need not necessarily be realized by the moving members 51B and 73B, and may be realized by another configuration. The hemostatic device 10 may perform the first distal end operation and the second distal end operation by operating the first operation unit 510 so as to move to the distal end side. Further, the hemostatic device 10 may perform the first distal end operation by operating the first operation unit 510 so as to move to the distal end side, and perform the second distal end operation by operation the first operation unit 510 so as to move to the proximal end side.

In the hemostatic device 20, the configuration to restrict the tube proximal end operation until the first distal end operation is complete and to release the restriction of the tube proximal end operation once the first distal end operation is complete, and the configuration to restrict the second distal end operation until the tube proximal end operation is complete and to release the restriction of the second distal end operation once the tube proximal end operation is complete, need not necessarily be realized by the first moving member 3A and the fourth moving member 3B, and may be realized by another configuration. The hemostatic device 20 may perform the first distal end operation, the tube proximal end operation, and the second distal end operation by operating the first operation unit 12 so as to move to the proximal end side. Further, the hemostatic device 20 may perform the first distal end operation by operating the first operation unit 12 so as to move to the distal end side, perform the tube proximal end operation by operating the first operation unit 12 so as to move to the proximal end side, and perform the second distal end operation by operating the first operation unit 12 so as to move to the distal end side.

The coupling section 71C of the hemostatic device 10 may be able to always move with respect to the housing 71, or, in contrast, may be unable to move with respect to the housing 71. The coupling section 71C may be able to be switched between a state of being able to move in the extending direction and a state of not being able to move in the extending direction in accordance with an operation by the user, independently of the necessity for the first distal end operation and the second distal end operation. The second tubular member 8D need not necessarily be coupled to the second tubular member 8D via the coupling section 71C, and may be directly connected to the housing 71. The same applies to the hemostatic device 20.

The coupling section 1C of the hemostatic device 10 may be able to be switched from a state of being unable to move in the extending direction to a state of being able to move in the extending direction, by the first distal end operation. The coupling section 1C of the hemostatic device 20 may be able to be switched between the state of being unable to move in the extending direction and the state of being able to move in the extending direction, by the tube proximal end operation.

The first operation units 510 and 12, and the third operation units 530 and 13 are not limited to being the slide levers. For example, the first operation units 510 and 12, and the third operation units 530 and 13 may be configured by a button, and may perform various operations as a result of being pressed. Further, for example, the first operation units 510 and 12, and the third operation units 530 and 13 may be configured by a dial, and may perform various operations as a result of the dial being rotated. Respective operation units (a slide lever, a button, a dial, and the like) that execute each of the first distal end operation and the second distal end operation may be separately provided.

In the hemostatic device 10, the movement of the coupling section 71C from the sixth distal end position to the sixth proximal end position may be restricted by a mechanism different from the restricting mechanism 74C. Similarly, in the hemostatic device 20, the movement of the coupling section 1C from the coupling distal end position to the coupling proximal end position may be restricted by a mechanism different from the restricting mechanism 4C. For example, the hemostatic devices 10 and 20 may include an operation unit (a button, for example) that becomes operable in accordance with the second distal end operation. The coupling section 71C may be enabled to move from the sixth distal end position to the sixth proximal end position in accordance with an operation of that operation unit. The coupling section 1C may be enabled to move from the coupling distal end position to the coupling proximal end position in accordance with an operation of that operation unit.

The hemostatic device 10 need not necessarily include the second operation unit 520. Similarly, the hemostatic device 20 need not necessarily include the second operation unit 14. For example, in the positioning proximal end operation, the hemostatic devices 10 and 20 may cause the positioning member 8A to move relatively to the proximal end side in accordance with an operation of the first operation units 510 and 12.

The pinion gears 51C and 12A may be configured by a plurality of gears. Respective ratios of teeth numbers of the plurality of gears may be different from each other. In this case, the moving member 51B can be caused to move significantly in the extending direction by a slight operation of the first operation unit 510. Further, the fourth moving member 3B can be caused to move significantly in the extending direction by a slight operation of the first operation unit 12. The first operation unit 510 and the moving member 51B may be directly coupled to each other. The first operation unit 12 and the fourth moving member 3B may be directly coupled to each other. In this case, a movement direction of the first operation units 510 and 12 can be aligned with a movement direction of the moving member 51B and the fourth moving member 3B. Thus, the user can easily recognize the operation on the hemostatic devices 10 and 20, from the operation of the first operation units 510 and 12.

The first engagement section 82 is not limited to being the balloon, and may be another member that is capable of engaging with the opening 6A of the blood vessel 6.

The switching member 2B of the hemostatic device 20 switches the restricting member 2A from the restricting state to the enabling state by switching from the state in which the limiting sections 23A and 23B of the restricting member 2A are disposed in the first movement region of the first moving member 3A to the state in which the limiting sections 23A and 23B are not disposed in the first movement region. For example, the restricting member 2A may restrict the movement of the first moving member 3A by engaging, from the proximal end side, with the first moving member 3A. The switching member 2B may enable the movement of the push-out member 8B connected to the first moving member 3A by releasing the engaged state of the restricting member 2A with respect to the first moving member 3A. In this case, in the restricting state, the restricting member 2A need not necessarily be disposed in the first movement region of the first moving member 3A. The restricting member 2A may be configured to directly restrict the movement of the push-out member 8B. In this case, the hemostatic device 20 need not necessarily include the first moving member 3A.

The urging section 24 of the hemostatic device 20 may be a compression coil that urges the limiting sections 23A and 23B downward. The switching member 2B may include an end cam. The end cam may switch the restricting member 2A from the restricting state to the enabling state by moving the restricting member 2A upward in resistance to the urging force of the urging section 24, in accordance with the movement the switching member 2B. The urging section 24 is not limited to being the spring, and may be another member (elastic rubber or the like) that is able to apply the urging force to the limiting sections 23A and 23B.

The exposed section 43 may be disposed below the notification section 15 of the housing 1 when the switching member 2B of the hemostatic device 20 is disposed in the initial switching position. The exposed section 43 may be disposed further to the distal end side than the notification section 15 when the switching member 2B is disposed in the first switching position and the second switching position. In this case, when the switching member 2B is disposed in the initial switching position, the exposed section 43 can be visually observed via the notification section 15, and it is thus possible to recognize that the switching member 2B is in the initial switching position. The exposed section 43 may be disposed below the notification section 15 when the switching member 2B is disposed in the third switching position. The exposed section 43 may be disposed further to the distal end side than the notification section 15 when the switching member 2B is disposed in the first switching position, the second switching position, and the initial switching position. In this case, the exposed section 43 can be visually observed via the notification section 15 when the switching member 2B is in the third switching position. In this way, the hemostatic device 20 can perform notification that the positioning member 8A has moved excessively to the proximal end side, by causing the exposed section 43 to be exposed from the notification section 15.

The notification section 15 of the hemostatic device 20 may be provided above the switching member 2B. In this way, the switching member 2B may be directly visually observed via the notification section 15. In this case, the second moving member 4A need not necessarily be provided on the switching member 2B.

The switching member 2B of the hemostatic device 20 need not necessarily include the magnet 25A. The housing 1 need not necessarily include the magnets 141 to 143. The housing 1 may include a first restricting section that restricts the switching member 2B from moving from the second switching position to the first switching position. In this way, the switching member 2B may be inhibited from moving excessively to the first switching position. Further, the housing 1 may include a second restricting section that restricts the switching member 2B from moving further to the proximal end side than the third switching position. In this way, the switching member 2B may be inhibited from moving excessively further to the proximal end side than the third switching position. Further, the housing 1 may include only the magnet 142, and need not include the magnets 141 and 143.

The thickness of the partition wall on the upper side of the housing section 14C of the hemostatic device 20 may be greater than the thickness of the partition wall on the upper side of the housing section 14B. The thickness of the partition walls on the upper side of each of the housing sections 14A and 14C may be substantially the same thickness. The thickness of the partition walls on the upper side of the housing sections 14A and 14C may be greater than the thickness of the partition wall on the upper side of the housing section 14B. Further, the thickness of the partition walls on the upper side of the housing sections 14A and 14C may be less than the thickness of the partition wall on the upper side of the housing section 14B of the hemostatic device 20. The thickness of the partition wall on the upper side of the housing section 14B may be less than the thickness of the partition wall on the upper side of the housing section 14A of the hemostatic device 20, and the thickness of the partition wall on the upper side of the housing section 14C may be less than the thickness of the partition wall on the upper side of the housing section 14B of the hemostatic device 20. In other words, the thicknesses of the respective partition walls on the upper side of the housing sections 14A, 14B, and 14C of the hemostatic device 20 may decrease in that order.

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

What is claimed is:

1. A hemostatic device that closes a puncture hole extending to skin from an opening formed in a blood vessel, the hemostatic device comprising:
   a first tubular member extending in an extending direction;
   a positioning member, a part of which is provided inside the first tubular member, the positioning member including
      an extending section extending in the extending direction, and
      an engagement section provided at a distal end section of the extending section and engageable with the opening;
   a hemostatic agent disposed further to a proximal end side than the engagement section of the positioning member;
   a push-out member including a push-out distal end positioned further to the proximal end side than the hemostatic agent, and able to push out the hemostatic agent from a distal end section of the first tubular member, using the push-out distal end, when the push-out member moves relatively to a distal end side with respect to the first tubular member;

a housing configured to house at least a part of each of the first tubular member, the positioning member, and the push-out member;
a first operation unit configured to be operated by a user in order to perform each of
a first distal end operation that relatively moves the first tubular member and the push-out member to the distal end side with respect to the housing and the positioning member, and
a second distal end operation that relatively moves the push-out member to the distal end side with respect to the housing and the positioning member;
a switching mechanism configured to restrict the second distal end operation at least until the first distal end operation is complete, and to release the restriction of the second distal end operation and cause the second distal end operation to be executable once the first distal end operation is complete;
a coupling section coupled to a second tubular member through an interior of which at least a part of each of the first tubular member, the positioning member, and the push-out member is inserted; and
a second operation unit that is operated in order to perform a coupling proximal end operation that moves the coupling section to the proximal end side with respect to the housing, the first tubular member, the positioning member, and the push-out member,
wherein the switching mechanism further restricts the coupling proximal end operation until the second distal end operation is complete, and releases the restriction of the coupling proximal end operation and causes the coupling proximal end operation to be executable once the second distal end operation is complete.

2. The hemostatic device according to claim 1, wherein the switching mechanism includes a first switching section coupled to the first tubular member and a second switching section coupled to the push-out member,
in the first distal end operation, the first tubular member and the push-out member move relatively to the distal end side as a result of the first switching section and the second switching section moving relatively, in accordance with operation of the first operation unit, in a state of being in contact with each other, and
in the second distal end operation, the push-out member moves relatively to the distal end side as a result of the second switching section moving relatively, in accordance with operation of the first operation unit, in a state in which the second switching section is separated from the first switching section.

3. The hemostatic device according to claim 2, wherein the first operation unit is able to move relatively in the extending direction with respect to the housing,
the first distal end operation is performed in accordance with the first operation unit moving relatively with respect to the housing to one side in the extending direction, and
the second distal end operation is performed in accordance with the first operation unit moving relatively with respect to the housing further to the one side in the extending direction.

4. The hemostatic device according to claim 3, wherein the one side in the extending direction is the proximal end side, and another side in the extending direction is the distal end side.

5. The hemostatic device according to claim 1, wherein the first operation unit is further operated in order to perform a tube proximal end operation that relatively moves the first tubular member to the proximal end side with respect to the housing, the positioning member, and the push-out member,
in the second distal end operation, in addition to the push-out member, the first tubular member is further relatively moved to the distal end side,
the switching mechanism restricts the tube proximal end operation until the first distal end operation is complete, and releases the restriction of the tube proximal end operation and causes the tube proximal end operation to be executable once the first distal end operation is complete, and
the switching mechanism restricts the second distal end operation until the tube proximal end operation is complete, and releases the restriction of the second distal end operation and causes the second distal end operation to be executable once the tube proximal end operation is complete.

6. The hemostatic device according to claim 5, wherein the switching mechanism includes a first switching section coupled to the first tubular member and a second switching section coupled to the push-out member,
in the first distal end operation and the second distal end operation, the first tubular member and the push-out member move relatively to the distal end side as a result of the first switching section and the second switching section moving relatively, in accordance with operation of the first operation unit, in a state of being in contact with each other, and
in the tube proximal end operation, the first tubular member moves relatively to the proximal end side as a result of the first switching section moving relatively, in accordance with operation of the first operation unit, in a state in which the first switching section is separated from the second switching section.

7. The hemostatic device according to claim 5, wherein the first operation unit is able to move relatively in the extending direction with respect to the housing,
the first distal end operation is performed in accordance with the first operation unit moving relatively with respect to the housing by a predetermined amount, to one side in the extending direction,
the tube proximal end operation is performed in accordance with the first operation unit moving relatively with respect to the housing by the predetermined amount, to another side in the extending direction, and
the second distal end operation is performed in accordance with the first operation unit moving relatively with respect to the housing by the predetermined amount, to the one side in the extending direction.

8. The hemostatic device according to claim 1, wherein the coupling section includes a limiting section, the limiting section not being disposed in a movement region of the coupling section when the coupling section is able to move, and being disposed in the movement region when the coupling section is not able to move,
in the second distal end operation, in accordance with the push-out member relatively moving to the distal end side, the switching mechanism switches the limiting section from a state of being disposed in the movement region to a state of not being disposed in the movement region, and
the restriction of the coupling proximal end operation is released and the execution of the coupling proximal end operation is allowed by causing the coupling section to be in a state of being able to move to the proximal end side from a state of not being able to move.

9. The hemostatic device according to claim 1, further comprising:
a further operation unit that is operated in order to further perform a positioning proximal end operation that relatively moves the positioning member to the proximal end side with respect to the housing, the first tubular member, and the push-out member.

10. The hemostatic device according to claim 1, wherein the engagement section is a balloon capable of switching between an inflated state and a contracted state, and
the balloon engages with the opening when in the inflated state.

* * * * *